US012421626B2

(12) United States Patent
Bloom et al.

(10) Patent No.: US 12,421,626 B2
(45) Date of Patent: Sep. 23, 2025

(54) CELL-STORED BARCODED DEEP MUTATIONAL SCANNING LIBRARIES AND USES OF THE SAME

(71) Applicants: Fred Hutchinson Cancer Center, Seattle, WA (US); University of Washington, Seattle, WA (US)

(72) Inventors: Jesse Bloom, Seattle, WA (US); Adam S. Dingens, Seattle, WA (US); Katharine H. D. Crawford, Seattle, WA (US); Caelan Radford, Seattle, WA (US)

(73) Assignees: Fred Hutchinson Cancer Center, Seattle, WA (US); University of Washington, Seattle, WA (US)

( * ) Notice: Subject to any disclaimer, the term of this patent is extended or adjusted under 35 U.S.C. 154(b) by 1273 days.

(21) Appl. No.: 17/281,540

(22) PCT Filed: Jun. 28, 2019

(86) PCT No.: PCT/US2019/039952
§ 371 (c)(1),
(2) Date: Mar. 30, 2021

(87) PCT Pub. No.: WO2020/006494
PCT Pub. Date: Jan. 2, 2020

(65) Prior Publication Data
US 2021/0363661 A1 Nov. 25, 2021

Related U.S. Application Data

(60) Provisional application No. 62/692,398, filed on Jun. 29, 2018.

(51) Int. Cl.
*C40B 40/08* (2006.01)

(52) U.S. Cl.
CPC .................................. *C40B 40/08* (2013.01)

(58) Field of Classification Search
None
See application file for complete search history.

(56) References Cited

U.S. PATENT DOCUMENTS 5,994,515 A    11/1999  Hoxie
6,790,611 B2   9/2004   Lassen et al.
(Continued)

FOREIGN PATENT DOCUMENTS

EP    2423316 A1      2/2012
WO    WO9845259 A2   10/1998
(Continued)

OTHER PUBLICATIONS

Behera, et al., "Exploiting genetic variation to uncover rules of transcription factor binding and chromatin accessibility," Nat. Comm., vol. 9, No. 1, 2018, 15 pages.
(Continued)

*Primary Examiner* — Christian C Boesen
(74) *Attorney, Agent, or Firm* — C. Rachal Winger; Chrystal Quisenberry; Lee & Hayes PC

(57) ABSTRACT

Cell-stored barcoded viral protein deep mutational scanning libraries are described. The libraries can be used to map resistance mutations to therapeutic treatments. The libraries can be used to predict viruses that become resistant to therapeutic compounds and/or may more easily evolve to infect new species. The libraries can also be used to more safely study dangerous viruses that normally require high safety biocontainment facilities. The libraries include features that allow efficient collection and assessment of informative data, obviating many bottlenecks of previous approaches.

20 Claims, 19 Drawing Sheets

Specification includes a Sequence Listing.

(56) References Cited

U.S. PATENT DOCUMENTS

| | | | |
|---|---|---|---|
| 7,745,592 | B2 | 6/2010 | Massie et al. |
| 8,383,345 | B2 | 2/2013 | Shendure et al. |
| 8,476,225 | B2 | 7/2013 | Casarez et al. |
| 9,139,642 | B2 | 9/2015 | Williamson et al. |
| 9,259,433 | B2 | 2/2016 | Huang et al. |
| 2009/0214510 | A1 | 8/2009 | Nabel et al. |
| 2015/0203838 | A1 | 7/2015 | Mikkelsen et al. |
| 2016/0145603 | A1 | 5/2016 | Bloom |
| 2017/0157190 | A1 | 6/2017 | Lamb et al. |

FOREIGN PATENT DOCUMENTS

| | | | |
|---|---|---|---|
| WO | WO2006138118 | A2 | 12/2006 |
| WO | WO2008147427 | A2 | 12/2008 |
| WO | WO2009027057 | A1 | 3/2009 |
| WO | WO2009151313 | A1 | 12/2009 |
| WO | WO2012006596 | A2 | 1/2012 |
| WO | WO2013006795 | A2 | 1/2013 |
| WO | WO2013072917 | A2 | 5/2013 |
| WO | WO2013147584 | A1 | 10/2013 |
| WO | WO2014062892 | A1 | 4/2014 |
| WO | WO2014201416 | | 12/2014 |
| WO | WO2015011483 | A1 | 1/2015 |
| WO | WO2017143155 | A2 | 8/2017 |

OTHER PUBLICATIONS

Dingens, et al., "Comprehensive Mapping of HIV-1 Escape from a Broadly Neutralizing Antibody," Cell Host Microbe., vol. 21, No. 6, 2017, pp. 777-787.

Doud, et al., "Accurate Measurement of the Effects of All Amino-Acid Mutations on Influenza Hemagglutinin," Viruses, vol. 8, No. 6, 2016, 17 pages.

Doud, et al., "Complete mapping of viral escape from neutralizing antibodies," PLOS Pathogens, vol. 13, No. 3, 2017, 20 pages.

Haddox, et al., "Mapping mutational effects along the evolutionary landscape of HIV envelope," Elife, 7. pii:, 2018, e34420, 29 pages.

Invitation to Pay Fees Dated Oct. 7, 2019 in International Application No. PCT/US2019/039952, 5 pages.

Search Report and Written Opinion Dated Dec. 6, 2019 for International Application No. PCT/US19/39952, 28 pages.

Thyagarajan, et al., "The inherent mutational tolerance and antigenic evolvability of influenza hemagglutinin," eLife, 2014, 26 pages.

"Illumina Adapter Sequences," retrieved Jun. 1, 2021, at <<https://support-docs.illumina.com/SHARE/AdapterSeq/illumina-adapter-sequences.pdf>>, Illumina, 2018, 45 pages.

Anderson, et al., "Identification of epitopes on respiratory syncytial virus proteins by competitive binding immunoassay," Journal of Clinical Microbiology, vol. 23, No. 3, 1986, pp. 475-480.

Baron, et al., "Tetracycline-controlled transcription in eukaryotes: novel transactivators with graded transactivation potential," Nucleic Acids Research, vol. 25, No. 14, 1997, pp. 2723-2729.

Bersuker, et al., "Protein misfolding specifies recruitment to cytoplasmic inclusion bodies," Journal of Cell Biology, vol. 213, No. 2, 2016, pp. 229-241.

Blau & Rossi, "Tet B or not tet B: advances in tetracycline-inducible gene expression," PNAS USA, vol. 96, No. 3, 1999, pp. 797-799.

Bloom, "An experimentally determined evolutionary model dramatically improves phylogenetic fit," Molecular Biology and Evolution, vol. 31, No. 8, 2014, pp. 1956-1978.

Bloom, "Software for the analysis and visualization of deep mutational scanning data," BMC Bioinformatics, vol. 16, No. 168, 2015, 13 pages.

Bonger, et al., "General method for regulating protein stability with light," ACS Chemical Biology, vol. 9, No. 1, 2014, pp. 111-115.

Bossart, et al., "A neutralizing human monoclonal antibody protects african green monkeys from hendra virus challenge," Science Translational Medicine, vol. 3, No. 105, 2011, 17 pages.

Boyoglu-Barnum, et al., "Prophylaxis with a respiratory syncytial virus (RSV) anti-G protein monoclonal antibody shifts the adaptive immune response to RSV rA2-line19F infection from Th2 to Th1 in BALB/c mice," Journal of Virology, vol. 88, No. 18, 2014, pp. 10569-10583.

Brown, et al., "lac repressor can regulate expression from a hybrid SV40 early promoter containing a lac operator in animal cells," Cell, vol. 49, No. 5, 1987, pp. 603-612.

Buchen-Osmond, "The Universal Virus Database ICTVdB," Computing in Science & Engineering, vol. 5, 2003, pp. 16-25.

Burcin, et al., "Adenovirus-mediated regulable target gene expression in vivo," PNAS USA, vol. 96, No. 2, 1999, pp. 355-360.

Burton, et al., "Efficient neutralization of primary isolates of HIV-1 by a recombinant human monoclonal antibody," Science, vol. 266, No. 5187, 1994, pp. 1024-1027.

Chin, et al., "Nonhybrid, finished microbial genome assemblies from long-read SMRT sequencing data," Nature Methods, vol. 10, No. 6, 2013, pp. 563-569.

Coleman, et al., "Efficient large-scale production and concentration of HIV-1-based lentiviral vectors for use in vivo," Physiological Genomics, vol. 12, No. 3, 2003, pp. 221-228.

Corti, et al., "Prophylactic and postexposure efficacy of a potent human monoclonal antibody against MERS coronavirus," PNAS USA, vol. 112, No. 33, 2015, pp. 10473-10478.

Cronin, et al., "Altering the tropism of lentiviral vectors through pseudotyping," Current Gene Therapy, vol. 5, No. 4, 2005, pp. 387-398.

Dalba, et al., "Replication-competent vectors and empty virus-like particles: new retroviral vector designs for cancer gene therapy or vaccines," Molecular Therapy, vol. 15, No. 3, 2007, pp. 457-466.

De Wit, et al., "Middle East respiratory syndrome coronavirus (MERS-CoV) causes transient lower respiratory tract infection in rhesus macaques," PNAS USA, vol. 110, No. 41, 2013, pp. 16593-16603.

DeBuysscher, et al., "Comparison of the pathogenicity of Nipah virus isolates from Bangladesh and Malaysia in the Syrian hamster," PLoS Neglected Tropical Diseases, vol. 7, No. 1, 2013, 11 pages.

DePristo, et al., "A framework for variation discovery and genotyping using next-generation DNA sequencing data," Nature Genetics, vol. 43, No. 5, 2011, pp. 491-498.

Diskin, et al., "Restricting HIV-1 pathways for escape using rationally designed anti-HIV-1 antibodies," Journal of Experimental Medicine, vol. 210, No. 6, 2013, pp. 1235-1249.

Doud, et al., "Quantifying the effects of single mutations on viral escape from broad and narrow antibodies to an H1 Influenza hemagglutinin," BioRxiv, 2018, 39 pages.

Drugbank, "AMD-070," retrieved on Jun. 1, 2021 at <<https://go.drugbank.com/drugs/DB05501>>, Drugbank Accession No. DB05501, 2007, 5 pages.

Drugbank, "PRO-542," retrieved on Jun. 1, 2021 at <<https://go.drugbank.com/drugs/DB05793>>, Drugbank Accession No. DB05793, 2007, 4 pages.

Egeler, et al., "Ligand-switchable substrates for a ubiquitin-proteasome system," Journal of Biological Chemistry, vol. 286, No. 36, 2011, pp. 31328-31336.

Faden, et al., "Phenotypes on demand via switchable target protein degradation in multicellular organisms," Nature Communications, vol. 7, No. 12202, 2016, 15 pages.

Falkowska, et al., "Broadly neutralizing HIV antibodies define a glycan-dependent epitope on the prefusion conformation of gp41 on cleaved envelope trimers," Immunity, vol. 40, No. 5, 2014, pp. 657-668.

Findlay, et al., "Saturation editing of genomic regions by multiplex homology-directed repair," Nature, vol. 513, No. 7516, 2014, pp. 120-123.

Firnberg & Ostermeier, "PFunkel: efficient, expansive, user-defined mutagenesis," PLoS One, vol. 7, No. 12, 2012, 10 pages.

Fogle, et al., "Fozivudine tidoxil as single-agent therapy decreases plasma and cell-associated viremia during acute feline immunodeficiency virus infection," Journal of Veterinary Internal Medicine, vol. 25, No. 3, 2011, pp. 413-418.

(56) References Cited

OTHER PUBLICATIONS

Fowler, et al., "Measuring the activity of protein variants on a large scale using deep mutational scanning," Nature Protocol, vol. 9, No. 9, 2014, pp. 2267-2284.

Francica, et al., "Steric shielding of surface epitopes and impaired immune recognition induced by the ebola virus glycoprotein," PLoS Pathogens, vol. 6, No. 9, 2010, 13 pages.

Galimi, et al., "A role for bone marrow-derived cells in the vasculature of noninjured CNS," Blood, vol. 105, No. 6, 2005, pp. 2400-2402.

Geisbert, et al., "Development of a new vaccine for the prevention of Lassa fever," PLoS Medicine, vol. 2, No. 6, 2005, 9 pages.

Geisbert, et al., "Therapeutic treatment of Nipah virus infection in nonhuman primates with a neutralizing human monoclonal antibody," Science Translational Medicine, vol. 6, No. 242, 2014, 16 pages.

Gong, et al., "Stability-mediated epistasis constrains the evolution of an influenza protein," Elife, vol. 2, 2013, 19 pages.

Gossen, et al., "Transcriptional activation by tetracyclines in mammalian cells," Science, vol. 268, No. 5218, 1995, pp. 1766-1769.

Gunther, et al., "Imported lassa fever in Germany: molecular characterization of a new lassa virus strain," Emerging Infectious Diseases, vol. 6, No. 5, 2000, pp. 466-476.

Haddox, et al., "Experimental Estimation of the Effects of All Amino-Acid Mutations to HIV's Envelope Protein on Viral Replication in Cell Culture," PLoS Pathogens, vol. 12, 2016, 32 pages.

Hanna, et al., "Antiviral activity, pharmacokinetics, and safety of BMS-488043, a novel oral small-molecule HIV-1 attachment inhibitor, in HIV-1-infected subjects," Antimicrobial Agents and Chemotherapy, vol. 55, No. 2, 2011, pp. 722-728.

Hartenbach & Fussenegger, "Autoregulated, bidirectional and multicistronic gas-inducible mammalian as well as lentiviral expression vectors," Journal of Biotechnology, vol. 120, No. 1, 2005, pp. 83-98.

Hiatt, et al., "Parallel, tag-directed assembly of locally derived short sequence reads," Nature Methods, vol. 7, No. 2, 2010, pp. 119-122.

Hilton, et al., "phydms: software for phylogenetic analyses informed by deep mutational scanning," PeerJ, vol. 5, 2017, 20 pages.

Hoffmann, et al., "A Dna transfection system for generation of influenza A virus from eight plasmids," PNAS USA, vol. 97, No. 11, 2000, pp. 6108-6113.

Hopf, et al., "Mutation effects predicted from sequence co-variation," Nature Biotechnology, vol. 35, No. 2, 2017, pp. 128-135.

Hu & Davidson, "The inducible lac operator-repressor system is functional in mammalian cells," Cell, vol. 48, No. 4, 1987, pp. 555-566.

Hussain & Lenard, "Characterization of PDR4, a *Saccharomyces cerevisiae* gene that confers pleiotropic drug resistance in high-copy number: identity with YAP1, encoding a transcriptional activator" Gene, vol. 101, No. 1, 1991, pp. 149-152.

Inokoshi, et al., "Cerulenin-resistant mutants of *Saccharomyces cerevisiae* with an altered fatty acid synthase gene," Molecular and General Genetics MGG, vol. 244, 1994, pp. 90-96.

Iwamoto, "A general chemical method to regulate protein stability in the mammalian central nervous system," Chemistry & Biology, vol. 17, No. 9, 2010, pp. 981-988.

Jacobson, "Safety, pharmacokinetics, and antiretroviral activity of multiple doses of ibalizumab (formerly TNX-355), an anti-CD4 monoclonal antibody, in human immunodeficiency virus type 1-infected adults," Antimicrobial Agents and Chemotherapy, vol. 53, No. 2, 2009, pp. 450-457.

Jahrling, et al., "Endemic Lassa fever in Liberia. IV. Selection of optimally effective plasma for treatment by passive immunization," Transactions of The Royal Society of Tropical Medicine and Hygiene, vol. 79, No. 3, 1985, pp. 380-384.

Jain & Varadarajan, "A rapid, efficient, and economical inverse polymerase chain reaction-based method for generating a site saturation mutant library," Analytical Biochemistry, vol. 449, 2014, pp. 90-98.

Jones, et al., "Live attenuated recombinant vaccine protects non-human primates against Ebola and Marburg viruses," Nature Medicine, vol. 11, No. 786, 2005, pp. 786-790.

Julien, et al., "Broadly neutralizing antibody PGT121 allosterically modulates CD4 binding via recognition of the HIV-1 gp120 V3 base and multiple surrounding glycans," PLoS Pathogens, vol. 9, No. 5, 2013, 15 pages.

Karin, et al., "Primary structure and transcription of an amplified genetic locus: the CUP1 locus of yeast," PNAS USA, vol. 81, No. 2, 1984, pp. 337-341.

Kepler, "Unconventional Interrogation Yields HIV's Escape Plan," Cell Host & Microbe, vol. 21, No. 6, 2017, pp. 659-660.

Khetawat & Broder, "A functional henipavirus envelope glycoprotein pseudotyped lentivirus assay system," Virology Journal, vol. 7, 2010, 14 pages.

Kitzman, et al., "Massively parallel single-amino-acid mutagenesis," Nature Methods, vol. 12, No. 3, 2015, pp. 203-206.

Kutner, et al., "Production, concentration and titration of pseudotyped HIV-1-based lentiviral vectors," Nature Protocols, vol. 4, No. 4, 2009, pp. 495-505.

Laird Smith, et al., "Rapid Sequencing of Complete env Genes from Primary HIV-1 Samples," Virus Evolution, vol. 2, No. 2, 2016, 8 pages.

Larsen, et al., "The utility of PacBio circular consensus sequencing for characterizing complex gene families in non-model organisms," BMC Genomics, vol. 15, No. 720, 2014, 15 pages.

Laursen & Wilson, "Broadly neutralizing antibodies against influenza viruses," Antiviral Research, vol. 98, No. 3, 2013, pp. 476-483.

Lee & Saphire, "Ebolavirus glycoprotein structure and mechanism of entry," Future Virology, vol. 4, No. 6, 2009, pp. 621-635.

Lee, et al., "Deep mutational scanning of hemagglutinin helps predict evolutionary fates of human H3N2 influenza variants," PNAS USA, vol. 115, No. 35, 2018, pp. E8276-E8285.

Liu, et al., "Systematic comparison of 2A peptides for cloning multi-genes in a polycistronic vector," Scientific Reports, vol. 7, No. 1, 2017, 9 pages.

Louie, et al., "Fitness landscape of the human immunodeficiency virus envelope protein that is targeted by antibodies," PNAS USA, vol. 115, No. 4, 2018, pp. E564-E573.

Luke, et al., "Occurrence, function and evolutionary origins of '2A-like' sequences in virus genomes," Journal of General Virology, vol. 89, 2008, pp. 1036-1042.

Marzi, et al., "Ebola Vaccine. VSV-EBOV rapidly protects macaques against infection with the 2014/15 Ebola virus outbreak strain," Science, vol. 349, 2015, pp. 739-742.

Matheson, et al., "Antibody-free magnetic cell sorting of genetically modified primary human CD4+ T cells by one-step streptavidin affinity purification," PloS One, vol. 9, No. 10, 2014, 8 pages.

Matreyek, et al., "A platform for functional assessment of large variant libraries in mammalian cells," Nucleic Acids Research, vol. 45, No. 11, 2017, 12 pages.

Matsuzawa, et al., "Method for targeting protein destruction by using a ubiquitin-independent, proteasome-mediated degradation pathway," PNAS USA, vol. 102, No. 42, 2005, pp. 14982-14987.

McKnight, et al., "Inhibition of human immunodeficiency virus fusion by a monoclonal antibody to a coreceptor (CXCR4) is both cell type and virus strain dependent," Journal of Virology, vol. 71, No. 2, 1997, pp. 1692-2696.

Mire, et al., "Human-monoclonal-antibody therapy protects nonhuman primates against advanced Lassa fever," Nature Medicine, vol. 23, No. 10, 2017, pp. 1146-1149.

Mitta, et al., "Design and in vivo characterization of self-inactivating human and non-human lentiviral expression vectors engineered for streptogramin-adjustable transgene expression," Nucleic Acids Research, vol. 32, No. 12, 2004, 14 pages.

Miyoshi, et al., "Development of a self-inactivating lentivirus vector," Journal of Virology, vol. 72, No. 10, 1998, pp. 8150-8157.

Moncla, et al., "Influenza Evolution: New Insights into an Old Foe," Trends in Microbiology, vol. 25, No. 6, 2017, pp. 432-434.

Mullick, et al., "The cumate gene-switch: a system for regulated expression in mammalian cells," BMC Biotechnology, vol. 6, No. 43, 2006, 18 pages.

(56) References Cited

OTHER PUBLICATIONS

Munster, et al., "Protective efficacy of a novel simian adenovirus vaccine against lethal MERS-CoV challenge in a transgenic human DPP4 mouse model," NPJ Vaccines, vol. 2, No. 28, 2017, 4 pages.
Murin, et al., "Structures of protective antibodies reveal sites of vulnerability on Ebola virus," PNAS USA, vol. 111, No. 48, 2014, pp. 17182-17187.
Nakata, et al., "Potent Anti-R5 Human Immunodeficiency Virus Type 1 Effects of a CCR5 Antagonist, AK602/ONO4128/GW873140, in a Novel Human Peripheral Blood Mononuclear Cell Nonobese Diabetic-SCID, Interleukin-2 Receptor GAMMA-Chain-Knocked-Out AIDS Mouse Model," Journal of Virology, vol. 79, No. 4, 2005, pp. 2087-2096.
Pascal, et al., "Pre- and postexposure efficacy of fully human antibodies against Spike protein in a novel humanized mouse model of MERS-CoV infection," PNAS USA, vol. 112, No. 28, 2015, pp. 8738-8743.
Pelegrin, et al., "Antiviral Monoclonal Antibodies: Can They Be More Than Simple Neutralizing Agents?," Trends in Microbiology, vol. 23, No. 10, 2015, pp. 653-665.
Pert, et al., "Octapeptides deduced from the neuropeptide receptor-like pattern of antigen T4 in brain potently inhibit human immunodeficiency virus receptor binding and T-cell infectivity," PNAS USA, vol. 83, No. 23, 1986, pp. 9254-9258.
Poelwijk, et al., "Learning the pattern of epistasis linking genotype and phenotype in a protein," Nature Communications, vol. 10, No. 4213, 2019, 11 pages.
Pond, et al., "HyPhy: hypothesis testing using phylogenies," Bioinformatics, vol. 21, No. 5, 2005, pp. 676-679.
Qiu, et al., "Reversion of advanced Ebola virus disease in nonhuman primates with Zmapp," Nature, vol. 514, No. 7520, 2014, pp. 47-53.
Qiu, et al., "Two-mAb cocktail protects macaques against the Makona variant of Ebola virus," Science Translational Medicine, vol. 8, No. 329, 2016, 11 pages.
Renicke, et al., "A LOV2 domain-based optogenetic tool to control protein degradation and cellular function," Chemistry & Biology, vol. 20, No. 4, 2013, pp. 619-626.
Roberts, et al., "The advantages of SMRT sequencing," Genome Biology, vol. 14, No. 7, 2013, 4 pages.
Robinson, et al., "Most neutralizing human monoclonal antibodies target novel epitopes requiring both Lassa virus glycoprotein subunits," Nature Communications, vol. 7, No. 11544, 2016, 14 pages.
Russell, et al., "Improving pandemic influenza risk assessment," Elife, vol. 3, 2014, 12 pages.
Sailer & Harms, "Detecting High-Order Epistasis in Nonlinear Genotype-Phenotype Maps," Genetics, vol. 205, No. 3, 2017, pp. 1079-1088.
Sailer & Harms, "High-order epistasis shapes evolutionary trajectories," PLOS Computational Biology, vol. 13, No. 5, 2017, 16 pages.
Scheid, et al., "HIV-1 antibody 3BNC117 suppresses viral rebound in humans during treatment interruption," Nature, vol. 535, No. 7613, 2016, pp. 556-560.
Schutze, et al., "A streamlined protocol for emulsion polymerase chain reaction and subsequent purification," Analytical Biochemistry, vol. 410, No. 1, 2011, pp. 155-157.
Sommerstein, et al., "Arenavirus Glycan Shield Promotes Neutralizing Antibody Evasion and Protracted Infection," PLoS Pathogens, vol. 11, No. 11, 2015, 25 pages.
Tran, et al., "Mapping of Ebolavirus Neutralization by Monoclonal Antibodies in the ZMapp Cocktail Using Cryo-Electron Tomography and Studies of Cellular Entry," Journal of Virology, vol. 90, No. 17, 2016, pp. 7618-7627.
Travers, et al., "A flexible and efficient template format for circular consensus sequencing and SNP detection," Nucleic Acids Research, vol. 38, No. 15, 2010, pp. 8 pages.
Verity, et al., "Broad neutralization and complement-mediated lysis of HIV-1 by PEHRG214, a novel caprine anti-HIV-1 polyclonal antibody," AIDS, vol. 20, No. 4, 2006, pp. 505-515.
Wang, et al., "A regulatory system for use in gene transfer," PNAS USA, vol. 91, No. 71, 1994, pp. 8180-8184.
Whitehead, et al., "Nicking Mutagenesis: comprehensive single-site saturation mutagenesis," Protocol Exchange, 2016, 9 pages.
Witting, et al., "Characterization of a third generation lentiviral vector pseudotyped with Nipah virus envelope proteins for endothelial cell transduction," Gene Therapy, vol. 20, 2013, pp. 997-1005.
Wrenbeck, et al., "Plasmid-based one-pot saturation mutagenesis," Nature Methods, vol. 13, No. 11, 2016, pp. 928-930.
Extended European Search Report Dated Jun. 10, 2022 for European Patent Application No. 19824586.2, 9 pages.

FIG. 1

(prior art)

FIG. 2

(prior art)

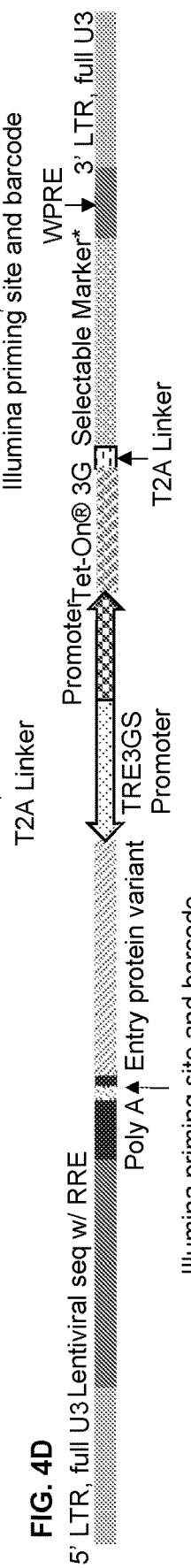
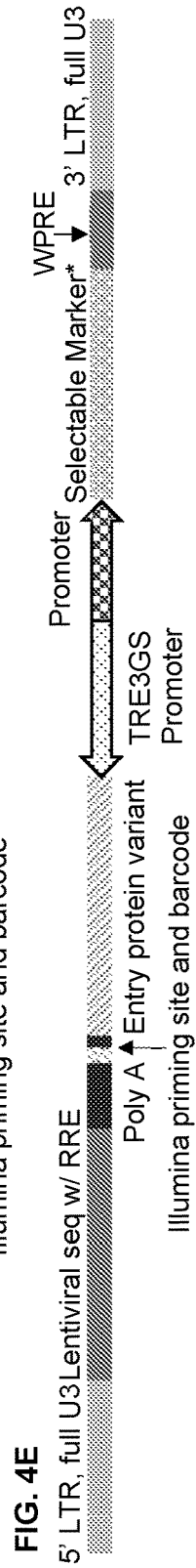
FIG. 4A
FIG. 4B
FIG. 4C
FIG. 4D
FIG. 4E
FIG. 4F

(prior art)

Let $f_{r,x}^{start}$ be the true frequency of character $x$ at site $r$ in the starting library, and let $f_{r,x}^{s1}$ and $f_{r,x}^{s2}$ be the frequencies after selections $s1$ and $s2$, respectively. The differential preference $\Delta\pi_{r,x}$ for $x$ at $r$ in by $s2$ versus $s1$ is defined by:

$$f_{r,x}^{s1} = \left(\pi_{r,x}^{s1} \times f_{r,x}^{start}\right) \div \left(\pi_{r,y}^{s1} \times \sum_{y} f_{r,y}^{start}\right)$$

$$f_{r,x}^{s2} = \left[\left(\pi_{r,x}^{s1} + \Delta\pi_{r,x}\right) \times f_{r,x}^{start}\right] \div \left[\left(\pi_{r,y}^{s1} + \Delta\pi_{r,y}\right) \times \sum_{y} f_{r,y}^{start}\right]$$

where $\pi_{r,x}^{s1}$ is the "control preference" and is treated as a nuisance parameter, and constraints include $$\sum_{x} \Delta\pi_{r,x} = 0$$

$$1 \geq \Delta\pi_{r,x} + \pi_{r,x}^{s1} \geq 0$$

If there is no difference in the effect of $x$ at $r$ between selections $s1$ and $s2$, then $\Delta\pi_{r,x} = 0$. If $x$ at $r$ is more preferred by $s2$ than $s1$, then $\Delta\pi_{r,x} > 0$; conversely if $x$ at $r$ is more preferred by $s1$ than $s2$, then $\Delta\pi_{r,x} < 0$.

FIG. 12
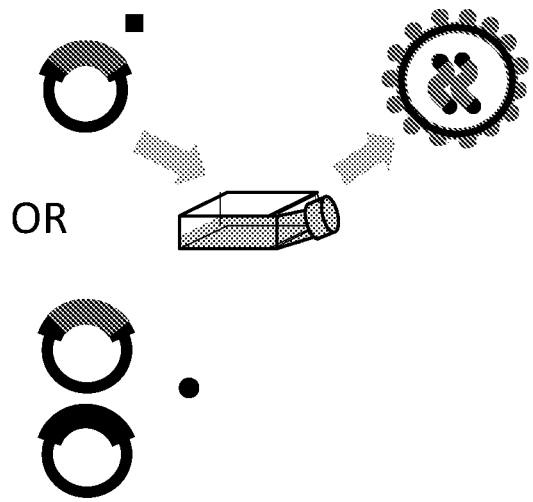
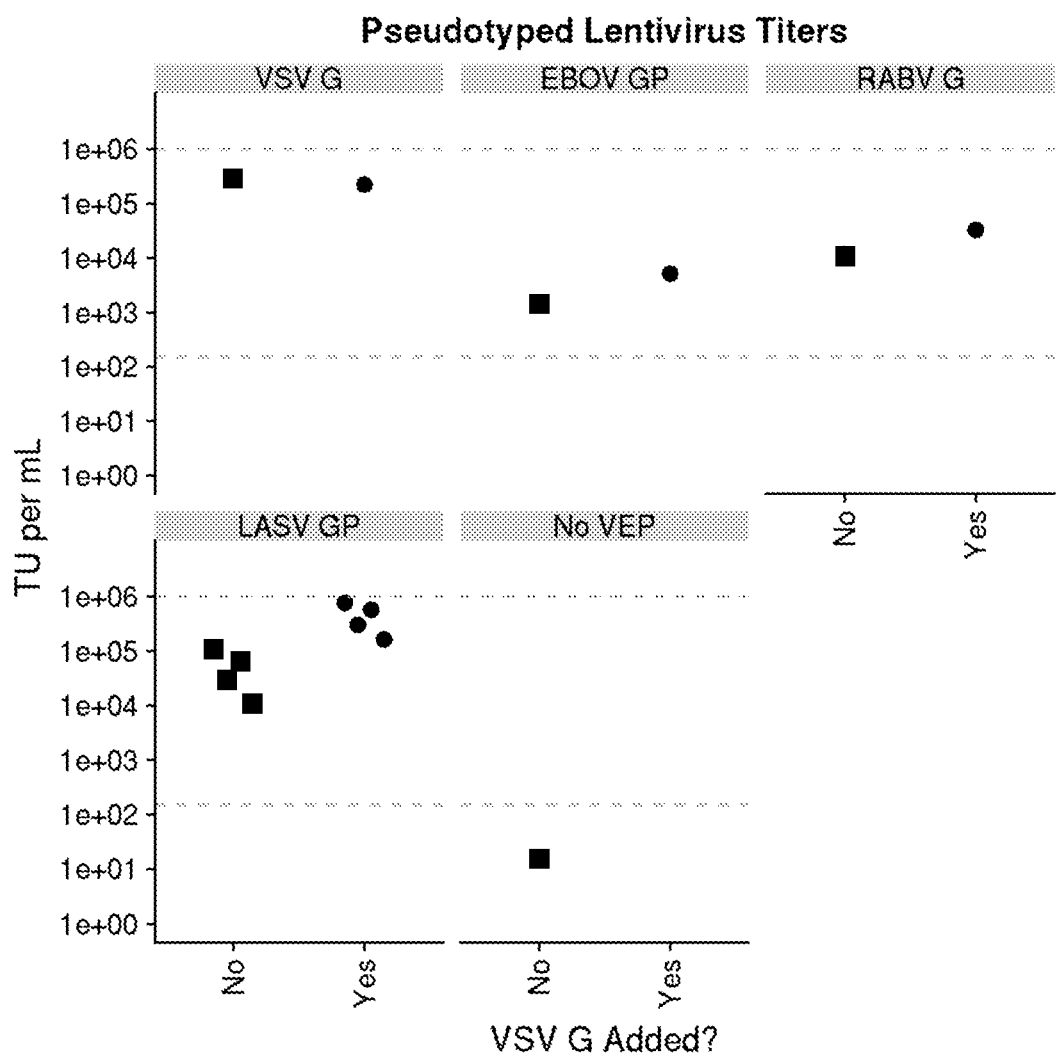

ZsG qPCR Data

| Sample | Ct Value |
|---|---|
| VSV G | 20.1 |
| LASV G1959 codon optimized | 23.6 |
| LASV Josiah codon optimized | 24.0 |
| LASV Josiah wildtype | 24.9 |
| RABV wildtype | 24.0 |
| LASV G1959 wildtype | 25.9 |
| LASV G1959 codon opt - Heat inactivated | 30.9 |

FIG. 15

>Rous sarcoma virus U3 (Cullen BR et al. (1985) Mol Cell Biol 5(3): 438-447)
AGTCCCCTCAGGATATAGTAGTTTCGCTTTTGCATAGGGAGGGGGAAATGTAGCCTTATGC
AATACTCTTGTAGTCTTGCAACATGCTTATGTAACGATGAGTTAGCAACATGCCTTACAAGG
AGAGAAAAAGCACCGTGCATGCCGATTGGTGGAAGTAAGGTGGTACGATCGTGCCTTATT
AGGAAGGCAACAGACGGGTCTGACATGGATTGGACGAACCACCGAATTCGCATTGCAGAG
AGTATTGTATTTAAGTGCCTAGCTCGATACAATAAAC (SEQ ID NO: 42)

>HIV-1 gag nucleotide sequence from plasmid psPAX2
ATGGGTGCGAGAGCGTCAGTATTAAGCGGGGGAGAATTAGATCGATGGGAAAAAATTCGG
TTAAGGCCAGGGGGAAAGAAAAAATATAAATTAAAACATATAGTATGGGCAAGCAGGGAGC
TAGAACGATTCGCAGTTAATCCTGGCCTGTTAGAAACATCAGAAGGCTGTAGACAAATACT
GGGACAGCTACAACCATCCCTTCAGACAGGATCAGAAGAACTTAGATCATTATATAATACA
GTAGCAACCCTCTATTGTGTGCATCAAAGGATAGAGATAAAAGACACCAAGGAAGCTTTAG
ACAAGATAGAGGAAGAGCAAAACAAAAGTAAGAAAAAAGCACAGCAAGCAGCAGCTGACA
CAGGACACAGCAATCAGGTCAGCCAAAATTACCCTATAGTGCAGAACATCCAGGGGCAAAT
GGTACATCAGGCCATATCACCTAGAACTTTAAATGCATGGGTAAAAGTAGTAGAAGAGAAG
GCTTTCAGCCCAGAAGTGATACCCATGTTTTCAGCATTATCAGAAGGAGCCACCCCACAAG
ATTTAAACACCATGCTAAACACAGTGGGGGGACATCAAGCAGCCATGCAAATGTTAAAAGA
GACCATCAATGAGGAAGCTGCAGAATGGGATAGAGTGCATCCAGTGCATGCAGGGCCTAT
TGCACCAGGCCAGATGAGAGAACCAAGGGGAAGTGACATAGCAGGAACTACTAGTACCCT
TCAGGAACAAATAGGATGGATGACACATAATCCACCTATCCCAGTAGGAGAAATCTATAAA
AGATGGATAATCCTGGGATTAAATAAAATAGTAAGAATGTATAGCCCTACCAGCATTCTGGA
CATAAGACAAGGACCAAAGGAACCCTTTAGAGACTATGTAGACCGATTCTATAAAACTCTAA
GAGCCGAGCAAGCTTCACAAGAGGTAAAAAATTGGATGACAGAAACCTTGTTGGTCCAAAA
TGCGAACCCAGATTGTAAGACTATTTTAAAAGCATTGGGACCAGGAGCGACACTAGAAGAA
ATGATGACAGCATGTCAGGGAGTGGGGGGACCCGGCCATAAAGCAAGAGTTTTGGCTGAA
GCAATGAGCCAAGTAACAAATCCAGCTACCATAATGATACAGAAAGGCAATTTTAGGAACC
AAAGAAAGACTGTTAAGTGTTTCAATTGTGGCAAAGAAGGGCACATAGCCAAAAATTGCAG
GGCCCCTAGGAAAAAGGGCTGTTGGAAATGTGGAAAGGAAGGACACCAAATGAAAGATTG
TACTGAGAGACAGGCTAATTTTTTAGGGAAGATCTGGCCTTCCCACAAGGGAAGGCCAGG
GAATTTTCTTCAGAGCAGACCAGAGCCAACAGCCCCACCAGAAGAGAGCTTCAGGTTTGG
GGAAGAGACAACAACTCCCTCTCAGAAGCAGGAGCCGATAGACAAGGAACTGTATCCTTTA
GCTTCCCTCAGATCACTCTTTGGCAGCGACCCCTCGTCACAATAA (SEQ ID NO: 43)

>HIV-1 gag protein sequence from plasmid psPAX2
MGARASVLSGGELDRWEKIRLRPGGKKKYKLKHIVWASRELERFAVNPGLLETSEGCRQILGQ
LQPSLQTGSEELRSLYNTVATLYCVHQRIEIKDTKEALDKIEEEQNKSKKKAQQAAADTGHSNQ
VSQNYPIVQNIQGQMVHQAISPRTLNAWVKVVEEKAFSPEVIPMFSALSEGATPQDLNTMLNTV
GGHQAAMQMLKETINEEAAEWDRVHPVHAGPIAPGQMREPRGSDIAGTTSTLQEQIGWMTHN
PPIPVGEIYKRWIILGLNKIVRMYSPTSILDIRQGPKEPFRDYVDRFYKTLRAEQASQEVKNWMT
ETLLVQNANPDCKTILKALGPGATLEEMMTACQGVGGPGHKARVLAEAMSQVTNPATIMIQKG
NFRNQRKTVKCFNCGKEGHIAKNCRAPRKKGCWKCGKEGHQMKDCTERQANFLGKIWPSHK
GRPGNFLQSRPEPTAPPEESFRFGEETTTPSQKQEPIDKELYPLASLRSLFGSDPSSQ (SEQ ID NO: 44)

FIG. 15 cont'd

>HIV-1 gag nucleotide sequence from plasmid pNL4-3 (GenBank accession no. AF324493.2)
ATGGGTGCGAGAGCGTCGGTATTAAGCGGGGGAGAATTAGATAAATGGGAAAAAATTCGG
TTAAGGCCAGGGGGAAAGAAACAATATAAACTAAAACATATAGTATGGGCAAGCAGGGAGC
TAGAACGATTCGCAGTTAATCCTGGCCTTTTAGAGACATCAGAAGGCTGTAGACAAATACT
GGGACAGCTACAACCATCCCTTCAGACAGGATCAGAAGAACTTAGATCATTATATAATACAA
TAGCAGTCCTCTATTGTGTGCATCAAAGGATAGATGTAAAAGACACCAAGGAAGCCTTAGA
TAAGATAGAGGAAGAGCAAAACAAAAGTAAGAAAAAGGCACAGCAAGCAGCAGCTGACAC
AGGAAACAACAGCCAGGTCAGCCAAAATTACCCTATAGTGCAGAACCTCCAGGGGCAAAT
GGTACATCAGGCCATATCACCTAGAACTTTAAATGCATGGGTAAAAGTAGTAGAAGAGAAG
GCTTTCAGCCCAGAAGTAATACCCATGTTTTCAGCATTATCAGAAGGAGCCACCCCACAAG
ATTTAAATACCATGCTAAACACAGTGGGGGGACATCAAGCAGCCATGCAAATGTTAAAAGA
GACCATCAATGAGGAAGCTGCAGAATGGGATAGATTGCATCCAGTGCATGCAGGGCCTAT
TGCACCAGGCCAGATGAGAGAACCAAGGGGAAGTGACATAGCAGGAACTACTAGTACCCT
TCAGGAACAAATAGGATGGATGACACATAATCCACCTATCCCAGTAGGAGAAATCTATAAA
AGATGGATAATCCTGGGATTAAATAAAATAGTAAGAATGTATAGCCCTACCAGCATTCTGGA
CATAAGACAAGGACCAAAGGAACCCTTTAGAGACTATGTAGACCGATTCTATAAAACTCTAA
GAGCCGAGCAAGCTTCACAAGAGGTAAAAAATTGGATGACAGAAACCTTGTTGGTCCAAAA
TGCGAACCCAGATTGTAAGACTATTTTAAAAGCATTGGGACCAGGAGCGACACTAGAAGAA
ATGATGACAGCATGTCAGGGAGTGGGGGGACCCGGCCATAAAGCAAGAGTTTTGGCTGAA
GCAATGAGCCAAGTAACAAATCCAGCTACCATAATGATACAGAAAGGCAATTTTAGGAACC
AAAGAAAGACTGTTAAGTGTTTCAATTGTGGCAAAGAAGGGCACATAGCCAAAAATTGCAG
GGCCCCTAGGAAAAAGGGCTGTTGGAAATGTGGAAAGGAAGGACACCAAATGAAAGATTG
TACTGAGAGACAGGCTAATTTTTTAGGGAAGATCTGGCCTTCCCACAAGGGAAGGCCAGG
GAATTTTCTTCAGAGCAGACCAGAGCCAACAGCCCCACCAGAAGAGAGCTTCAGGTTTGG
GGAAGAGACAACAACTCCCTCTCAGAAGCAGGAGCCGATAGACAAGGAACTGTATCCTTTA
GCTTCCCTCAGATCACTCTTTGGCAGCGACCCCTCGTCACAATAA (SEQ ID NO: 45)

>HIV-1 gag protein sequence from plasmid pNL4-3 (GenBank accession no. AAK08483.1)
MGARASVLSGGELDKWEKIRLRPGGKKQYKLKHIVWASRELERFAVNPGLLETSEGCRQILGQ
LQPSLQTGSEELRSLYNTIAVLYCVHQRIDVKDTKEALDKIEEEQNKSKKKAQQAAADTGNNSQ
VSQNYPIVQNLQGQMVHQAISPRTLNAWVKVVEEKAFSPEVIPMFSALSEGATPQDLNTMLNT
VGGHQAAMQMLKETINEEAAEWDRLHPVHAGPIAPGQMREPRGSDIAGTTSTLQEQIGWMTH
NPPIPVGEIYKRWIILGLNKIVRMYSPTSILDIRQGPKEPFRDYVDRFYKTLRAEQASQEVKNWM
TETLLVQNANPDCKTILKALGPGATLEEMMTACQGVGGPGHKARVLAEAMSQVTNPATIMIQK
GNFRNQRKTVKCFNCGKEGHIAKNCRAPRKKGCWKCGKEGHQMKDCTERQANFLGKIWPSH
KGRPGNFLQSRPEPTAPPEESFRFGEETTTPSQKQEPIDKELYPLASLRSLFGSDPSSQ (SEQ
ID NO: 46)

FIG. 15 cont'd

\>HIV-1 pol nucleotide sequence from plasmid psPAX2
TTTTTTAGGGAAGATCTGGCCTTCCCACAAGGGAAGGCCAGGGAATTTTCTTCAGAGCAGA
CCAGAGCCAACAGCCCCACCAGAAGAGAGCTTCAGGTTTGGGGAAGAGACAACAACTCCC
TCTCAGAAGCAGGAGCCGATAGACAAGGAACTGTATCCTTTAGCTTCCCTCAGATCACTCT
TTGGCAGCGACCCCTCGTCACAATAAAGATAGGGGGGCAATTAAAGGAAGCTCTATTAGAT
ACAGGAGCAGATGATACAGTATTAGAAGAAATGAATTTGCCAGGAAGATGGAAACCAAAAA
TGATAGGGGGAATTGGAGGTTTTATCAAAGTAAGACAGTATGATCAGATACTCATAGAAATC
TGCGGACATAAAGCTATAGGTACAGTATTAGTAGGACCTACACCTGTCAACATAATTGGAA
GAAATCTGTTGACTCAGATTGGCTGCACTTTAAATTTTCCCATTAGTCCTATTGAGACTGTA
CCAGTAAAATTAAAGCCAGGAATGGATGGCCCAAAAGTTAAACAATGGCCATTGACAGAAG
AAAAAATAAAAGCATTAGTAGAAATTTGTACAGAAATGGAAAAGGAAGGAAAAATTTCAAAA
ATTGGGCCTGAAAATCCATACAATACTCCAGTATTTGCCATAAAGAAAAAGACAGTACTAA
ATGGAGAAAATTAGTAGATTTCAGAGAACTTAATAAGAGAACTCAAGATTTCTGGGAAGTTC
AATTAGGAATACCACATCCTGCAGGGTTAAAACAGAAAAAATCAGTAACAGTACTGGATGT
GGGCGATGCATATTTTTCAGTTCCCTTAGATAAAGACTTCAGGAAGTATACTGCATTTACCA
TACCTAGTATAAACAATGAGACACCAGGGATTAGATATCAGTACAATGTGCTTCCACAGGG
ATGGAAAGGATCACCAGCAATATTCCAGTGTAGCATGACAAAAATCTTAGAGCCTTTTAGAA
AACAAAATCCAGACATAGTCATCTATCAATACATGGATGATTTGTATGTAGGATCTGACTTA
GAAATAGGGCAGCATAGAACAAAAATAGAGGAACTGAGACAACATCTGTTGAGGTGGGGA
TTTACCACACCAGACAAAAAACATCAGAAAGAACCTCCATTCCTTTGGATGGGTTATGAACT
CCATCCTGATAAATGGACAGTACAGCCTATAGTGCTGCCAGAAAAGGACAGCTGGACTGTC
AATGACATACAGAAATTAGTGGGAAAATTGAATTGGGCAAGTCAGATTTATGCAGGGATTAA
AGTAAGGCAATTATGTAAACTTCTTAGGGGAACCAAAGCACTAACAGAAGTAGTACCACTA
ACAGAAGAAGCAGAGCTAGAACTGGCAGAAAACAGGGAGATTCTAAAAGAACCGGTACAT
GGAGTGTATTATGACCCATCAAAAGACTTAATAGCAGAAATACAGAAGCAGGGGCAAGGCC
AATGGACATATCAAATTTATCAAGAGCCATTTAAAAATCTGAAAACAGGAAAGTATGCAAGA
ATGAAGGGTGCCCACACTAATGATGTAAACAATTAACAGAGGCAGTACAAAAAATAGCCA
CAGAAAGCATAGTAATATGGGGAAAGACTCCTAAATTTAAATTACCCATACAAAAGGAAACA
TGGGAAGCATGGTGGACAGAGTATTGGCAAGCCACCTGGATTCCTGAGTGGGAGTTTGTC
AATACCCCTCCCTTAGTGAAGTTATGGTACCAGTTAGAGAAAGAACCCATAATAGGAGCAG
AAACTTTCTATGTAGATGGGGCAGCCAATAGGGAAACTAAATTAGGAAAAGCAGGATATGT
AACTGACAGAGGAAGACAAAAAGTTGTCCCCCTAACGGACACAACAAATCAGAAGACTGAG
TTACAAGCAATTCATCTAGCTTTGCAGGATTCGGGATTAGAAGTAAACATAGTGACAGACTC
ACAATATGCATTGGGAATCATTCAAGCACAACCAGATAAGAGTGAATCAGAGTTAGTCAGT
CAAATAATAGAGCAGTTAATAAAAAGGAAAAAGTCTACCTGGCATGGGTACCAGCACACA
AAGGAATTGGAGGAAATGAACAAGTAGATAAATTGGTCAGTGCTGGAATCAGGAAAGTACT
ATTTTTAGATGGAATAGATAAGGCCCAAGAAGAACATGAGAAATATCACAGTAATTGGAGA
GCAATGGCTAGTGATTTTAACCTACCACCTGTAGTAGCAAAAGAAATAGTAGCCAGCTGTG
ATAAATGTCAGCTAAAAGGGGAAGCCATGCATGGACAAGTAGACTGTAGCCCAGGAATATG
GCAGCTAGATTGTACACATTTAGAAGGAAAAGTTATCTTGGTAGCAGTTCATGTAGCCAGT
GGATATATAGAAGCAGAAGTAATTCCAGCAGAGACAGGGCAAGAAACAGCATACTTCCTCT
TAAAATTAGCAGGAAGATGGCCAGTAAAAACAGTACATACAGACAATGGCAGCAATTTCAC
CAGTACTACAGTTAAGGCCGCCTGTTGGTGGCGGGGATCAAGCAGGAATTTGGCATTCC
CTACAATCCCCAAAGTCAAGGAGTAATAGAATCTATGAATAAAGAATTAAAGAAAATTATAG
GACAGGTAAGAGATCAGGCTGAACATCTTAAGACAGCAGTACAAATGGCAGTATTCATCCA
CAATTTTAAAAGAAAAGGGGGGATTGGGGGGTACAGTGCAGGGGAAAGAATAGTAGACAT
AATAGCAACAGACATACAAACTAAAGAATTACAAAAACAAATTACAAAAATTCAAAATTTTCG
GGTTTATTACAGGGACAGCAGAGATCCAGTTTGGAAAGGACCAGCAAAGCTCCTCTGGAA
AGGTGAAGGGGCAGTAGTAATACAAGATAATAGTGACATAAAAGTAGTGCCAAGAAGAAAA

FIG. 15 cont'd

GCAAAGATCATCAGGGATTATGGAAAACAGATGGCAGGTGATGATTGTGTGGCAAGTAGA
CAGGATGAGGATTAA (SEQ ID NO: 47)

>HIV-1 pol protein sequence from psPAX2
FFREDLAFPQGKAREFSSEQTRANSPTRRELQVWGRDNNSLSEAGADRQGTVSFSFPQITLW
QRPLVTIKIGGQLKEALLDTGADDTVLEEMNLPGRWKPKMIGGIGGFIKVRQYDQILIEICGHKAI
GTVLVGPTPVNIIGRNLLTQIGCTLNFPISPIETVPVKLPGMDGPKVKQWPLTEEKIKALVEICTE
MEKEGKISKIGPENPYNTPVFAIKKKDSTKWRKLVDFRELNKRTQDFWEVQLGIPHPAGLKQKK
SVTVLDVGDAYFSVPLDKDFRKYTAFTIPSINNETPGIRYQYNVLPQGWKGSPAIFQCSMTKILE
PFRKQNPDIVIYQYMDDLYVGSDLEIGQHRTKIEELRQHLLRWGFTTPDKKHQKEPPFLWMGY
ELHPDKWTVQPIVLPEKDSWTVNDIQKLVGKLNWASQIYAGIKVRQLCKLLRGTKALTEVVPLT
EEAELELAENREILKEPVHGVYYDPSKDLIAEIQKQGQGQWTYQIYQEPFKNLKTGKYARMKGA
HTNDVKQLTEAVQKIATESIVIWGKTPKFKLPIQKETWEAWWTEYWQATWIPEWEFVNTPPLV
KLWYQLEKEPIIGAETFYVDGAANRETKLGKAGYVTDRGRQKVVPLTDTTNQKTELQAIHLALQ
DSGLEVNIVTDSQYALGIIQAQPDKSESELVSQIIEQLIKKEKVYLAWVPAHKGIGGNEQVDKLVS
AGIRKVLFLDGIDKAQEEHEKYHSNWRAMASDFNLPPVVAKEIVASCDKCQLKGEAMHGQVDC
SPGIWQLDCTHLEGKVILVAVHVASGYIEAEVIPAETGQETAYFLLKLAGRWPVKTVHTDNGSN
FTSTTVKAACWWAGIKQEFGIPYNPQSQGVIESMNKELKKIIGQVRDQAEHLKTAVQMAVFIHN
FKRKGGIGGYSAGERIVDIIATDIQTKELQKQITKIQNFRVYYRDSRDPVWKGPAKLLWKGEGAV
VIQDNSDIKVVPRRKAKIIRDYGKQMAGDDCVASRQDED (SEQ ID NO: 48)

FIG. 15 cont'd

\>HIV-1 pol nucleotide sequence from plasmid pNL4-3 (GenBank accession no. AF324493.2)
TTTTTTAGGGAAGATCTGGCCTTCCCACAAGGGAAGGCCAGGGAATTTTCTTCAGAGCAGA
CCAGAGCCAACAGCCCCACCAGAAGAGAGCTTCAGGTTTGGGGAAGAGACAACAACTCCC
TCTCAGAAGCAGGAGCCGATAGACAAGGAACTGTATCCTTTAGCTTCCCTCAGATCACTCT
TTGGCAGCGACCCCTCGTCACAATAAAGATAGGGGGGCAATTAAAGGAAGCTCTATTAGAT
ACAGGAGCAGATGATACAGTATTAGAAGAAATGAATTTGCCAGGAAGATGGAAACCAAAAA
TGATAGGGGGAATTGGAGGTTTTATCAAAGTAAGACAGTATGATCAGATACTCATAGAAATC
TGCGGACATAAAGCTATAGGTACAGTATTAGTAGGACCTACACCTGTCAACATAATTGGAA
GAAATCTGTTGACTCAGATTGGCTGCACTTTAAATTTTCCCATTAGTCCTATTGAGACTGTA
CCAGTAAAATTAAAGCCAGGAATGGATGGCCCAAAAGTTAAACAATGGCCATTGACAGAAG
AAAAAATAAAAGCATTAGTAGAAATTTGTACAGAAATGGAAAAGGAAGGAAAAATTTCAAAA
ATTGGGCCTGAAAATCCATACAATACTCCAGTATTTGCCATAAAGAAAAAAGACAGTACTAA
ATGGAGAAAATTAGTAGATTTCAGAGAACTTAATAAGAGAACTCAAGATTTCTGGGAAGTTC
AATTAGGAATACCACATCCTGCAGGGTTAAAACAGAAAAAATCAGTAACAGTACTGGATGT
GGGCGATGCATATTTTTCAGTTCCCTTAGATAAAGACTTCAGGAAGTATACTGCATTTACCA
TACCTAGTATAAACAATGAGACACCAGGGATTAGATATCAGTACAATGTGCTTCCACAGGG
ATGGAAAGGATCACCAGCAATATTCCAGTGTAGCATGACAAAAATCTTAGAGCCTTTTAGAA
AACAAAATCCAGACATAGTCATCTATCAATACATGGATGATTTGTATGTAGGATCTGACTTA
GAAATAGGGCAGCATAGAACAAAAATAGAGGAACTGAGACAACATCTGTTGAGGTGGGGA
TTTACCACACCAGACAAAAAACATCAGAAAGAACCTCCATTCCTTTGGATGGGTTATGAACT
CCATCCTGATAAATGGACAGTACAGCCTATAGTGCTGCCAGAAAAGGACAGCTGGACTGTC
AATGACATACAGAAATTAGTGGGAAAATTGAATTGGGCAAGTCAGATTTATGCAGGGATTAA
AGTAAGGCAATTATGTAAACTTCTTAGGGGAACCAAAGCACTAACAGAAGTAGTACCACTA
ACAGAAGAAGCAGAGCTAGAACTGGCAGAAAACAGGGAGATTCTAAAAGAACCGGTACAT
GGAGTGTATTATGACCCATCAAAAGACTTAATAGCAGAAATACAGAAGCAGGGGCAAGGCC
AATGGACATATCAAATTTATCAAGAGCCATTTAAAAATCTGAAAACAGGAAAGTATGCAAGA
ATGAAGGGTGCCCACACTAATGATGTAAACAATTAACAGAGGCAGTACAAAAAATAGCCA
CAGAAAGCATAGTAATATGGGGAAAGACTCCTAAATTTAAATTACCCATACAAAAGGAAACA
TGGGAAGCATGGTGGACAGAGTATTGGCAAGCCACCTGGATTCCTGAGTGGGAGTTTGTC
AATACCCCTCCCTTAGTGAAGTTATGGTACCAGTTAGAGAAAGAACCCATAATAGGAGCAG
AAACTTTCTATGTAGATGGGGCAGCCAATAGGGAAACTAAATTAGGAAAAGCAGGATATGT
AACTGACAGAGGAAGACAAAAAGTTGTCCCCCTAACGGACACAACAAATCAGAAGACTGAG
TTACAAGCAATTCATCTAGCTTTGCAGGATTCGGGATTAGAAGTAAACATAGTGACAGACTC
ACAATATGCATTGGGAATCATTCAAGCACAACCAGATAAGAGTGAATCAGAGTTAGTCAGT
CAAATAATAGAGCAGTTAATAAAAAGGAAAAAGTCTACCTGGCATGGGTACCAGCACACA
AAGGAATTGGAGGAAATGAACAAGTAGATAAATTGGTCAGTGCTGGAATCAGGAAAGTACT
ATTTTTAGATGGAATAGATAAGGCCCAAGAAGAACATGAGAAATATCACAGTAATTGGAGA
GCAATGGCTAGTGATTTTAACCTACCACCTGTAGTAGCAAAAGAAATAGTAGCCAGCTGTG
ATAAATGTCAGCTAAAAGGGGAAGCCATGCATGGACAAGTAGACTGTAGCCCAGGAATATG
GCAGCTAGATTGTACACATTTAGAAGGAAAAGTTATCTTGGTAGCAGTTCATGTAGCCAGT
GGATATATAGAAGCAGAAGTAATTCCAGCAGAGACAGGGCAAGAAACAGCATACTTCCTCT
TAAAATTAGCAGGAAGATGGCCAGTAAAAACAGTACATACAGACAATGGCAGCAATTTCAC
CAGTACTACAGTTAAGGCCGCCTGTTGGTGGGCGGGATCAAGCAGGAATTTGGCATTCC
CTACAATCCCCAAAGTCAAGGAGTAATAGAATCTATGAATAAAGAATTAAAGAAAATTATAG
GACAGGTAAGAGATCAGGCTGAACATCTTAAGACAGCAGTACAAATGGCAGTATTCATCCA
CAATTTTAAAAGAAAAGGGGGGATTGGGGGGTACAGTGCAGGGGAAAGAATAGTAGACAT
AATAGCAACAGACATACAAACTAAAGAATTACAAAAACAAATTACAAAAATTCAAAATTTTCG
GGTTTATTACAGGGACAGCAGAGATCCAGTTTGGAAAGGACCAGCAAAGCTCCTCTGGAA
AGGTGAAGGGGCAGTAGTAATACAAGATAATAGTGACATAAAAGTAGTGCCAAGAAGAAAA

FIG. 15 cont'd

GCAAAGATCATCAGGGATTATGGAAAACAGATGGCAGGTGATGATTGTGTGGCAAGTAGA
CAGGATGAGGATTAA (SEQ ID NO: 49)

>HIV-1 pol protein sequence from plasmid pNL4-3 (GenBank accession no. AAK08484.2)
FFREDLAFPQGKAREFSSEQTRANSPTRRELQVWGRDNNSLSEAGADRQGTVSFSFPQITLW
QRPLVTIKIGGQLKEALLDTGADDTVLEEMNLPGRWKPKMIGGIGGFIKVRQYDQILIEICGHKAI
GTVLVGPTPVNIIGRNLLTQIGCTLNFPISPIETVPVKLKPGMDGPKVKQWPLTEEKIKALVEICTE
MEKEGKISKIGPENPYNTPVFAIKKKDSTKWRKLVDFRELNKRTQDFWEVQLGIPHPAGLKQKK
SVTVLDVGDAYFSVPLDKDFRKYTAFTIPSINNETPGIRYQYNVLPQGWKGSPAIFQCSMTKILE
PFRKQNPDIVIYQYMDDLYVGSDLEIGQHRTKIEELRQHLLRWGFTTPDKKHQKEPPFLWMGY
ELHPDKWTVQPIVLPEKDSWTVNDIQKLVGKLNWASQIYAGIKVRQLCKLLRGTKALTEVVPLT
EEAELELAENREILKEPVHGVYYDPSKDLIAEIQKQGQGQWTYQIYQEPFKNLKTGKYARMKGA
HTNDVKQLTEAVQKIATESIVIWGKTPKFKLPIQKETWEAWWTEYWQATWIPEWEFVNTPPLV
KLWYQLEKEPIIGAETFYVDGAANRETKLGKAGYVTDRGRQKVVPLTDTTNQKTELQAIHLALQ
DSGLEVNIVTDSQYALGIIQAQPDKSESELVSQIIEQLIKKEKVYLAWVPAHKGIGGNEQVDKLVS
AGIRKVLFLDGIDKAQEEHEKYHSNWRAMASDFNLPPVVAKEIVASCDKCQLKGEAMHGQVDC
SPGIWQLDCTHLEGKVILVAVHVASGYIEAEVIPAETGQETAYFLLKLAGRWPVKTVHTDNGSN
FTSTTVKAACWWAGIKQEFGIPYNPQSQGVIESMNKELKKIIGQVRDQAEHLKTAVQMAVFIHN
FKRKGGIGGYSAGERIVDIIATDIQTKELQKQITKIQNFRVYYRDSRDPVWKGPAKLLWKGEGAV
VIQDNSDIKVVPRRKAKIIRDYGKQMAGDDCVASRQDED (SEQ ID NO: 50)

>HIV-1 Tat coding sequence from plasmid pNL4-3 (GenBank accession no. AF324493.2)
ATGGAGCCAGTAGATCCTAGACTAGAGCCCTGGAAGCATCCAGGAAGTCAGCCTAAAACT
GCTTGTACCAATTGCTATTGTAAAAAGTGTTGCTTTCATTGCCAAGTTTGTTTCATGACAAAA
GCCTTAGGCATCTCCTATGGCAGGAAGAAGCGGAGACAGCGACGAAGAGCTCATCAGAAC
AGTCAGACTCATCAAGCTTCTCTATCAAAGCAACCCACCTCCCAATCCCGAGGGGACCCGA
CAGGCCCGAAGGAATAG (SEQ ID NO: 51)

>HIV-1 Tat protein sequence from plasmid pNL4-3 (GenBank accession no. AAK08486.1)
MEPVDPRLEPWKHGSQPKTACTNCYCKKCCFHCQVCFMTKALGISYGRKKRRQRRRAHQN
SQTHQASLSKQPTSQSRGDPTGPKE (SEQ ID NO: 52)

>HIV-1 Rev coding sequence from plasmid pNL4-3 (GenBank accession no. AF324493.2)
ATGGCAGGAAGAAGCGGAGACAGCGACGAAGAGCTCATCAGAACAGTCAGACTCATCAAG
CTTCTCTATCAAAGCAACCCACCTCCCAATCCCGAGGGGACCCGACAGGCCCGAAGGAAT
AGAAGAAGAAGGTGGAGAGAGAGACAGAGACAGATCCATTCGATTAGTGAACGGATCCTT
AGCACTTATCTGGGACGATCTGCGGAGCCTGTGCCTCTTCAGCTACCACCGCTTGAGAGA
CTTACTCTTGATTGTAACGAGGATTGTGGAACTTCTGGGACGCAGGGGGTGGGAAGCCCT
CAAATATTGGTGGAATCTCCTACAGTATTGGAGTCAGGAACTAAAGAATAG (SEQ ID NO: 53)

>HIV-1 Rev protein sequence from plasmid pNL4-3 (GenBank accession no. AAK08487.1)
MAGRSGDSDEELIRTVRLIKLLYQSNPPPNPEGTRQARRNRRRRWRERQRQIHSISERILSTYL
GRSAEPVPLQLPPLERLTLDCNEDCGTSGTQGVGSPQILVESPTVLESGTKE (SEQ ID NO: 54)

CELL-STORED BARCODED DEEP MUTATIONAL SCANNING LIBRARIES AND USES OF THE SAME

CROSS-REFERENCE TO RELATED APPLICATIONS

This application is a U.S. National Phase Application based on International Patent Application No. PCT/US2019/039952, filed on Jun. 28, 2019, which claims priority to U.S. Provisional Patent Application No. 62/692,398 filed Jun. 29, 2018, the entire contents each of which are incorporated by reference herein.

STATEMENT REGARDING FEDERALLY SPONSORED RESEARCH OR DEVELOPMENT

This invention was made with government support under Grant Nos. AI140891 and AI141707, awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 2GR7465_ST25.txt. The text file is 55.6 KB, was created on Mar. 29, 2021, and is being submitted electronically via EFS-Web.

FIELD OF THE DISCLOSURE

Cell-stored barcoded deep mutational scanning libraries are disclosed. The libraries can be used to map resistance mutations to therapeutic treatments. The libraries can also be used to predict viruses that may become resistant to therapeutic treatments and/or more easily evolve to infect new species. The libraries can also be used to more safely study dangerous viruses that normally require high safety biocontainment facilities. The libraries include features that allow efficient collection and assessment of informative data, obviating many bottlenecks of previous approaches.

BACKGROUND OF THE DISCLOSURE

Proteins are made of strings of amino acids with different proteins having different numbers and orders of amino acids. Proteins are essential to the functioning of cells and organisms. A powerful way to study proteins is through mutagenesis. Mutagenesis refers to altering the amino acid that naturally occurs at a position along the string of amino acids that create a given protein. Systematically altering amino acids at different positions through mutagenesis can identify those amino acids that are essential to the function of the protein. Deep mutational scanning refers to methods of generating and characterizing hundreds of thousands of mutants or more of a given protein. More particularly, deep mutational scanning can refer to altering each amino acid position with all possible alternative amino acids.

One scenario where the study of proteins is extremely beneficial is in relation to viruses. Many viruses can be effectively managed or treated. For example, vaccination has all but ameliorated smallpox and measles, once among mankind's greatest scourges. Unfortunately, however, numerous viruses continue to pose significant health threats. Examples include influenza, human immunodeficiency virus (HIV), Ebola virus, and Middle Eastern respiratory syndrome coronavirus (MERS-CoV).

To combat the spread of viruses, scientists and doctors need tools to know when drugs, vaccines, or antibodies are working against viral proteins, or conversely, when these viral proteins have developed resistance to therapeutics and pose a greater risk.

Replication of retroviruses, a type of virus that has an RNA genome, has been well studied. Once a retrovirus gains entry into a host cell, the viral RNA genome is copied by specialized enzymes into a DNA form that then goes to the nucleus of the host cell, where the host cell genome resides. The viral DNA integrates itself into the host cell genome. The ends of the viral RNA genome are flanked by regions of sequences called long terminal repeats (LTRs), which facilitate this integration. A region of the LTR called the U3 is important for transcription and packaging of the viral RNA genome (vRNA). After synthesis of viral gRNA, it is exported out of the nucleus into the host cell cytoplasm where this vRNA is packaged into new virions. The new virions bud off from the cell to start a new cycle of infection.

In the context of viral infection, years of research has led to an understanding of many of the proteins important in the virus life cycle. A virion is a complete infective form of a virus outside of a host's cell. The first step in viral infection is binding of the virion's viral entry protein to a host cell. This binding is followed by fusion of the virion with the host cell. For many human pathogenic viruses, the binding and fusion steps are performed by a single viral entry protein. For example, influenza virus, HIV, Ebola virus, and Lassa virus, all use a single entry protein for binding and fusion with a host cell. For other viruses, multiple proteins are involved. For example, Nipah virus has separate binding and fusion proteins.

Viral entry proteins are a primary target of immune system responses against infection. Most vaccines elicit neutralizing antibodies to the viral entry protein. Therapeutic antibodies can also be used to impair the activity of viral entry proteins, with the potential to both protect against infection as well as therapeutically treat active infection. However, viral entry proteins are able to mutate and evolve over time, and mutations can allow these proteins to escape recognition by immune system responses and therapeutic antibodies. Evasion or susceptibility to antibodies can be examined using mutant viral entry proteins in antibody neutralization assays.

A virus' viral entry protein is also a key determinant of the species that the particular virus can infect, and adaptive evolution of these entry proteins has been retrospectively characterized in most molecularly documented examples of non-human viruses jumping into humans. For example, the influenza pandemics of 1918, 1957, and 1968 all involved mutations that turned viral entry proteins from avian viral strains to strains that could better infect humans. The severe acute respiratory syndrome (SARS) coronavirus outbreak in 2003 was associated with mutations in the virus's entry protein that enabled it to better bind human receptors. The MERS-CoV viral entry protein has mutations that increase binding to human cells. Recent evidence also suggests that during the 2014-2016 Ebola outbreak, this virus's entry protein acquired mutations that promoted infection of human cells. Comparing the growth of viral mutants in different cell types can serve to identify mutations that contribute to host adaptation.

Therefore, it would be incredibly useful to identify particular amino acids within a viral entry protein that are important for binding and fusion to host cells and/or antibody evasion. The entry proteins of a few viruses (e.g., influenza, HIV) are well-characterized, but surprisingly little is known about the entry proteins of many less-studied viruses in part because these proteins are challenging to study. They form large metastable oligomers that are often heavily modified with sugar molecules which render them difficult targets for biochemistry and structural biology.

Deep mutational scanning has been used to completely map functional and antigenic effects of all mutations to the entry proteins of influenza virus and HIV. For example, FIG. 1 outlines an approach that was used to characterize mutations to the influenza entry protein, hemagglutinin (HA) and the HIV entry protein, Env. Briefly, all codon mutants of the genes encoding HA or Env were created and all associated replication-competent viruses were generated. These viruses were passaged in cell culture (e.g., transferred from a previous culture to fresh growth medium) and deep sequencing was used to quantify the frequency of every mutation in the passaged viruses versus the original pool to estimate the preference of each site for each amino acid (FIG. 1). The results of these experiments were informative for understanding the evolution of influenza and HIV in nature. The approach was also used to completely map how single amino acid mutations affect antibody neutralization. As shown in FIG. 1, the virus libraries were subjected to antibody or mock neutralization before infection into cells, and deep sequencing was used to identify mutations enriched by antibody selection. The results precisely pinpointed antibody epitopes and which specific mutations escape from antibody neutralization (FIG. 1).

The work described in relation to FIG. 1 garnered substantial notice. Kepler (2017) Cell Host & Microbe 21: 659-660; Moncla, et al. (2017) Trends in Microbiology 25: 432-434. For instance, Kepler stated: "Let's pause here to appreciate the advance in experimental power ushered in with this method. The investigators measured the effect of 12,559 distinct mutations . . . . The raw increase in numbers is crucial because it matches the extraordinary connectivity of the genotype space". And indeed, the scale of measurements vastly outstripped what was previously possible as shown in FIG. 2. Unfortunately, however, the applicability and utility of this described approach remained severely limited. While informative, these mutagenesis experiments were too low-throughput to keep up with the many relevant questions when studying rapidly evolving viruses that sample all possible mutations within a single human infection.

The approach depicted in FIG. 1 was advantageous because it directly measured viral infection or antibody neutralization. This contrasts with many high-throughput approaches that are currently available that measure surrogate viral activities like protein abundance or binding. Directly measuring infection or antibody neutralization is important because the functions of entry proteins are far more complex than can be inferred based on surrogate activities. However, performing functional experiments with replication-competent viruses has downsides. First, generating the virus libraries is complicated, with different challenges for every virus. FIG. 3 shows one process to generate diverse libraries of influenza viruses and processes for generating libraries of HIV is similarly complex. To create a library containing mutated DNA sequences encoding mutant influenza viral entry proteins with all possible amino acid mutations at each amino acid residue position, a molecular technique called polymerase chain reaction (PCR) using tiling mutagenic oligonucleotides, or short nucleic acid molecules containing all possible mutations, can be performed to generate the mutated DNA sequences. Each mutated DNA sequence that is created by this PCR then has to be inserted into plasmids, small circular, double-stranded DNA molecules that allow propagation of the mutated DNA sequences in an organism that serves as a factory to make more copies of the mutated DNA sequences. A typical organism used for this purpose is bacteria. The plasmid library thus made contains a large number of mutated DNA sequences encoding mutant viral entry proteins and can be stored and used in steps described below. Multiple plasmid libraries are typically generated, and each library has to be carried through subsequent steps independently to ensure statistical rigorousness. To determine mutations that are present in each mutated DNA sequence in a plasmid library and to be able to associate the mutations with viral entry protein functionality, further steps need to be performed with each plasmid library. First, virus particles (virions) having these mutated viral entry proteins on their surface need to be produced. Virions typically have two or three main parts: (i) a genome of DNA or RNA, which has genetic instructions for making new virions; (ii) a protein coat, called the capsid, which surrounds and protects the genome; and in some cases, (iii) an envelope of lipids, or fatty molecules, that surrounds the protein coat. The production of virions is achieved by bringing together viral components in cells capable of forming the virions. Cells that are typically used are eukaryotic cells such as mammalian cells. A process called transfection introduces into these cells the library plasmids, along with plasmids that allow expression of other viral proteins (such as proteins PA, PB1, PB2, and NP in FIG. 3). The transfection step allows the formation of complexes of viral proteins and nucleotide segments derived from the plasmid library encoding mutant viral entry proteins inside the mammalian cells. Then the cells that have these complexes are infected with a helper virus that is deficient for the viral entry protein being studied but containing any other necessary viral genome segments to produce fully competent virions. These virions, making up a mutant viral entry protein library, are then used to perform a second infection of appropriate cells, such as mammalian cells, at a low multiplicity of infection (MOI). The MOI refers to the ratio of agents (virions) to infection targets (cells). A low MOI allows better selection of functional mutants and a link between a mutant viral entry protein found on the surface of a virion (phenotype) and the gene segment encoding the mutant viral entry protein (genotype) in the virion. Then sequencing is performed on library plasmids to assess initial mutation frequencies and on viral DNA from infected cells to assess mutation frequencies after virions have been passaged through the mammalian cells. Moreover, each mutant library is paired with a control in which cells are transfected with a plasmid having a non-mutagenized (wild type) viral entry DNA sequence to generate initially wild type virions that are passaged in parallel with the mutant virions. Sequencing of the control allows for estimation of and statistical correction due to rates of apparent mutations arising from sources other than the original PCR mutagenesis, such as during sequencing and/or viral replication.

To achieve the results for influenza described in FIG. 3 and similar experiments for HIV, years of prior work were leveraged. For example, these experiments took advantage of the development of robust reverse genetics systems (approaches to generate virus from plasmid DNA), the ability to carefully control growth kinetics of these viruses in cell culture, the ability to grow these viruses to high titer and in large volumes, and various molecular tools to characterize the resulting virus. However, comparable molecular virology tools do not exist for most viruses. Moreover, virus libraries generated by plasmid transfection lack a genotype-phenotype link, and so must be passaged at a low MOI to create such a link (FIG. 3). Acceptable results can be obtained with a MOI ≤0.01 which requires >$10^8$ cells to maintain a diversity of $10^6$. Handling this many cells is problematic because viruses require biosafety containment. This is difficult but manageable for influenza and HIV, which can be worked with at biosafety level (BSL)-2/2+ conditions—but becomes almost unthinkable for BSL-3/4 viruses such as Ebola or MERS-CoV.

Another challenge is the deep sequencing required for this type of work. There is now substantial literature on sequencing methods for deep mutational scanning. The key point is that sequencing methods that are currently used (e.g., Illumina sequencing) can have an error rate that is too high to produce informative and reliable results. Alternative methods (such as PacBio) lack the throughput and/or accuracy to efficiently (and affordably) characterize diverse libraries at multiple conditions. One solution is to associate each variant in a library with a unique nucleotide barcode [Hiatt, et al. (2010) Nat Methods 7: 119-122]. The barcodes can then be sequenced using standard sequencing (e.g., Illumina) to read out the library composition. This approach is efficient and cheap and provides a linkage between barcode and variant. Unfortunately, however, standard barcoding, without more, does not work for many viruses for at least two reasons: First, the compactness of viral genomes means that it is hard to insert nucleotide barcodes without affecting fitness. Second, many viruses have high rates of recombination which often decouple barcodes from their variant sequence. Therefore, approaches to date have attached unique molecular identifiers (UMIs or barcodes) to PCR subamplicons each time the library is sequenced. Each mutated DNA sequence encoding a mutant viral entry protein can be divided into fragments to be sequenced. A barcode can be a random stretch of nucleotides that serves as a unique tag to identify a DNA molecule that is sequenced, and two different barcodes can be incorporated by PCR into a DNA molecule, one barcode at each end of the DNA molecule. In the context of sequencing mutated DNA sequences present in a viral entry protein library, PCR is performed to generate PCR subamplicons, which are many copies of each fragment of a mutated DNA sequence, containing barcodes at the ends of the subamplicons. The barcoded subamplicons are then sequenced. This approach requires a lot of sequencing because each barcoded subamplicon must be sequenced multiple times for error correction. A barcode is useful because repeated identification of a barcode during sequencing reveals resampling of a DNA molecule associated with that barcode. The output of a sequencing is sequence reads, which are strings of nucleotides for every DNA fragment of every mutated DNA sequence. Sequence reads with the same barcode can then be grouped together and differences among the sequence reads in a given barcode family can be readily detected. Differences in sequences at a given nucleotide position can represent true viral entry protein mutations if they occur in the majority of the sequence reads, while non-relevant mutations arising from errors due to experimental processes such as PCR and sequencing can occur in a minority of the reads. This approach also does not provide linkage information among mutations in different subamplicons, as subamplicons making up a given mutated DNA sequence in a library are generated and sequenced separately, thus losing linkage among multiple mutations that may occur along the complete length of a mutated DNA library sequence. Thus, there is significant room for improvement in the ability to create and assess deep mutational scanning libraries of proteins, such as viral entry proteins.

SUMMARY OF THE DISCLOSURE

Described herein is a new approach for performing deep mutational scanning of proteins. The current disclosure provides cell-stored barcoded mutational scanning libraries of proteins. Among many potential uses, the libraries can be used to map quickly and with high resolution amino acid changes in a given protein that are important to escape binding to a ligand. The libraries can be used to predict viruses that may become resistant to therapeutic treatments and/or that may more easily evolve to infect new species. The libraries can also be used to more safely study dangerous viruses that normally require high safety biocontainment facilities. The libraries include features that allow efficient collection and assessment of informative data, obviating many bottlenecks of previous approaches.

For example, systems and methods disclosed herein overcome inefficiencies associated with deep sequencing by providing new methods of associating barcodes with variant protein sequences within a library. The new association methods avoid loss of the original link between barcode and variant sequence due to recombination. This is achieved by creating virions that enter cells only once, thus not allowing a full replication cycle and limiting opportunities for recombination. Additionally, in particular embodiments, each cell of a cell-stored barcoded deep mutational scanning library contains at most one variant sequence integrated, so virions produced from each cell include retroviral genomes where the two copies of a variant sequence are identical. Therefore, even when recombination occurs, the link between barcode and variant sequence is maintained. Because the barcode-variant sequence link is maintained, sequencing can be utilized to sequence only the barcodes, greatly enhancing the throughput of the systems.

The systems and methods overcome biosafety and containment considerations by storing the library of genes encoding variant proteins in a non-infective state within holding cells. More particularly, the library is stored as barcoded non-replicative variants inside cells. In particular embodiments, the variant proteins are viral entry proteins. In particular embodiments, virion production can be induced by transfecting the storing cells with viral helper plasmids that encode the rest of the retroviral particle proteins. This results in expression in each cell of retroviral particles that are packaged with a barcoded gene encoding a given mutant viral entry protein and pseudotyped with that particular mutant viral entry protein. The ability to produce virions that package a barcoded gene encoding a mutant viral entry protein following transfection with helper plasmids is achieved, in part, through use of a vector that is not self-inactivating. In particular embodiments, this is achieved by including a functional U3.

Following generation of virions from the storage cells, functional studies can be conducted to assess variant proteins. For example, and as indicated previously, in particular embodiments, the systems and methods disclosed herein can be used to map quickly and with high resolution amino acid changes in a given protein that are important to escape binding to a ligand. This application is valuable in situations such as immunotherapy that depend upon binding of antibodies, chimeric antigen receptors (CARs), or other ligands to target proteins for killing of diseased cells. In particular embodiments, the systems and methods disclosed herein can be used to map the epitopes of antibodies. In particular embodiments, the systems and methods disclosed herein can be used to inform antibody drug development by characterizing mutations in target proteins that allow development of resistance to antibodies. In particular embodiments, the systems and methods disclosed herein can be used to assess the ability of different viral entry proteins to evade antibody neutralization, overcome drug inhibition, and/or infect new species. If numerous mutations to a viral entry protein allow antibody evasion, drug resistance, or infection of a new host species, the virus may have a higher probability of becoming a health threat. If, however, only few or very specific mutations allow antibody evasion, drug resistance, or infection of a new host species, the virus may pose less of a threat.

Taken together, the disclosed cell-stored barcoded mutational scanning libraries of proteins provide an important advance in the ability to generate, store, and characterize a large number of variant proteins. In particular embodiments, the libraries allow development of antibody therapeutics. In particular embodiments, the libraries allow study and control of viruses and viral outbreaks.

BRIEF DESCRIPTION OF THE SEVERAL VIEWS OF THE DRAWINGS

Many of the drawings submitted herein may be better understood in color. Applicant considers the color versions of the drawings as part of the original submission and reserves the right to present color images of the drawings in later proceedings.

FIG. 1. Prior approach to measure the effects of all amino acid mutations to influenza viral entry protein, hemagglutinin (HA). All codon mutants (II) of wild type HA gene (I) were created and influenza viruses carrying these mutants were generated (III). The viruses were passaged in cell culture to select functional variants (IV), and treated with antibody to select antigenic mutants (top part of V). No treatment with antibody is used as a control (bottom part of V). Deep sequencing passaged viruses (VI) versus the initial mutant pool (VII) quantified the functional effect of each mutation. The letter height in the logo plot of VIII is proportional to preference for that amino acid. A representative structure (IX) is shaded by mutational tolerance from low (lighter gray) to high (darker gray). Data from Doud & Bloom (2016) Viruses 8: 155. Deep sequencing of antibody-selected viruses (X) versus a control (XI) quantified the antigenic effect of each mutation. The letter height in the logo plot of XII is proportional to immune selection for that mutation. A representative structure (XIII) is shaded by immune selection from weak (lighter gray) to strong (darker gray). Data from Doud, et al. (2017) PLoS Pathog. 13(3): e1006271.

FIG. 2. Number of Env sites and total mutations characterized for neutralization by PGT151 using mutational antigenic profiling (left: Dingens et al. (2017) Cell Host & Microbe 21: 777-787) or neutralization assays (right: Falkowska et al. (2014) Immunity 40: 657-668). BF520, JR-CSF, and LAI refer to different HIV Env strains. Adapted from Dingens et al. (2017).

FIGS. 4A-4F. Exemplary lentiviral backbone constructs. (FIG. 4A) Each viral entry protein variant can be barcoded with 18-nucleotides after the stop codon. Integration is marked by a GFP reporter with a T2A linker [Liu, et al. (2017) Scientific Reports 7: 2193] to the entry protein, and LTRs have the full, functional U3, meaning that integrated backbones, which include the barcode, can be transcribed and packaged into virions. (FIG. 4B) A lentiviral construct as in (FIG. 4A), but with the Woodchuck Hepatitis Virus Posttranscriptional Regulatory Element (WPRE) sequence removed to reduce the expression of the viral entry protein variant. (FIG. 4C) A lentiviral construct as in (FIG. 4A), but with a degradation domain linked to the viral entry protein variant to allow for the controlled expression of the viral entry protein. (FIG. 4D) A lentiviral construct as in (FIG. 4A), but with the viral entry protein variant under the control of an inducible promoter (here, the Tet-On® 3G system (Clontech Laboratories, Mountain View, CA) that is different than the promoter of the selectable marker. The Tet-On® 3G transactivator that activates the TRE3GS promoter when bound to an inducer molecule is constitutively expressed from the promoter that also controls the expression of the selectable marker. (FIG. 4E) A lentiviral construct as in (FIG. 4D), but without constitutive expression of the Tet-On® 3G transactivator necessary for induction (the transactivator would need to be supplied in trans). (FIG. 4F) A lentiviral construct as in (FIG. 4A), but with the viral entry protein variant and selectable marker under the control of an inducible promoter. RRE=Rev responsive element.

FIGS. 8A-8C. Measuring antibody neutralization curves using deep sequencing of viral libraries and visualizing the results. (FIG. 8A) At each antibody concentration, a specific fraction of each viral variant survives neutralization. Here all but the V1K variant are mostly neutralized. (FIG. 8B) By measuring the fraction surviving at several concentrations, a neutralization curve can be interpolated. The middle vertical dashed line is the concentration corresponding to the scenario in FIG. 8A. (FIG. 8C) When curves for many mutants have been measured, it is more informative to show the resulting measurements in logo plots [Adapted from Doud et al. (2018) bioRxiv DOI: 210468]. The height of each letter is the fraction of variants with that mutation that survive at the antibody concentrations indicated by vertical lines in FIG. 8B.

FIG. 9. Algorithms to extract functional information from deep mutational scanning counts adapted from Bloom (2015) BMC Bioinformatics 16: 168.

FIG. 10. The functional effects of all mutations can be mapped in cells from relevant host species. For instance, in the case of Nipah virus, the natural animal reservoir is bats and the relevant test species can be humans. Species-specific maps of mutational effects can be used to inform sequence-based methods to identify viral host adaptation. For example, in the logo plots (I), at the $4^{th}$ site, amino acid E is favored in bat cells but K is favored in human cells. New viral sequences can be scored for their adaptation to each host (II).

FIGS. 11A, 11B. Scoring host adaptation. (FIG. 11A) Viruses are adapted to their long-standing animal reservoirs. When they jump to humans, they initially may be poorly adapted. (FIG. 11B) Host adaptation can be scored based on sequence, and adaptation after a jump can be charted.

FIG. 12. Producing lentiviruses pseudotyped with diverse viral entry proteins. The plot shows the viral titer of lentiviruses created from transfected constructs in which the different viral entry proteins were cloned into the repaired U3 lentiviral backbone plasmid. Squares show the lentivirus titer when each backbone was transfected into 293T cells alongside lentiviral helper plasmids (expressing Gag/Pol, Tat, and Rev). Circles show lentiviral titer when VSV-G was also transfected into the 293T cells, such that the lentivirus is pseudotyped with both the viral entry protein of interest and VSV-G. Titer in transduction units (TU) was determined using flow cytometry to measure GFP expression in 293T cells, which express the relevant receptors for these viruses (VSV G: LDL receptor; EBOV GP: NPC1; RABV G: Endocytosis mediated cell entry; LASV: alpha-dystroglycan). The lower grey dotted line is the limit of detection. VSV G=vesicular stomatitis virus G glycoprotein. EBOV GP=Ebola virus glycoprotein. RABV G=rabies virus glycoprotein. LASV GP=Lassa virus glycoprotein. VEP=viral entry protein.

FIG. 13. Recovery of lentiviruses bearing diverse viral entry proteins from transduced cells. This plot shows the titers of pseudotyped lentiviruses, in which the viral entry protein comes from an integrated viral entry protein gene. In the "Integrant" condition, lentiviral helper plasmids (expressing Gag/Pol, Tat, and Rev, without VSV G or other viral entry protein) were transfected into the integrated cell lines to produce the lentivirus. The "+lentiviral BB" condition involves additionally transfecting in the lentiviral backbone. The "+VSV G" condition involves additionally transfecting in VSV G protein expression plasmid, serving as an additional positive control. The "no HPs" condition involves no transfection of the lentiviral helper plasmids into an integrated cell line. The lower grey dotted line is the limit of detection. VSV G=vesicular stomatitis virus G glycoprotein. EBOV GP=Ebola virus glycoprotein. RABV G=rabies virus glycoprotein. LASV GP=Lassa virus glycoprotein. VEP=viral entry protein.

FIGS. 14A, 14B. The lentiviral backbones encoding viral entry proteins can be sequenced from infected cells. (FIG. 14A) Non-integrated viral DNA was harvested from cells infected with lentiviruses packaging a backbone encoding LASV GP at 9 hours post-infection (hpi) and 12 hpi. The full-length LASV GP gene was amplified from these samples, from a plasmid control, from cells infected with heat-inactivated virus (HI), or from cells infected with a negative control supernatant (NoHPs—no helper plasmids). (FIG. 14B) Lentiviral construct DNA was quantified using qPCR against the ZsGreen marker gene present in all of the constructs. Cells infected with lentiviruses made with the constructs have $2^{10}$ to $2^5$ more copies of DNA than the negative control background heat inactivated sample. Lower Ct values indicate more DNA is present.

FIG. 15. Sequences supporting the disclosure (SEQ ID NOs: 42-54).

DETAILED DESCRIPTION

Figure 3:
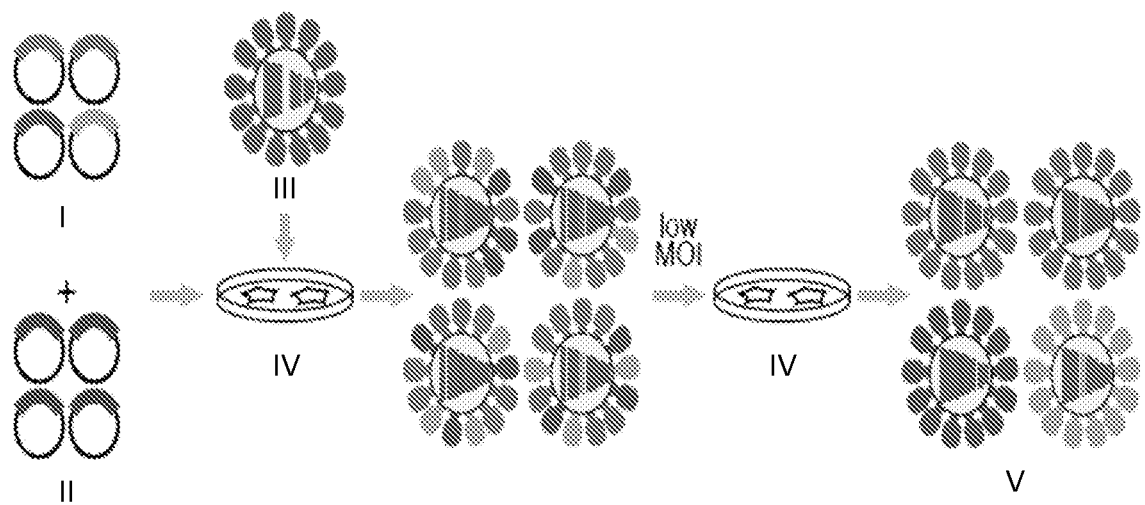
FIG. 3. Intricacies of creating mutant libraries of influenza virions. Cells were transfected with a mix of plasmids including an HA mutant plasmid library (I) and PB2/PB1/PA/NP protein expression plasmids (II), infected with a specially engineered helper virus (III) into MDCK-SIAT1-TMPRSS2 cells (IV), and large amounts of replication-competent influenza virus were passaged at low multiplicity of infection (MOI) in the same cells (IV) to generate a passaged mutant virus library (V) that linked genotype and phenotype [Adapted from Doud & Bloom, supra]. This approach is complicated and does not generalize to other viruses.

Proteins are made of strings of amino acids with different proteins having different numbers and orders of amino acids.

Proteins are essential to the functioning of cells and organisms. A powerful way to study proteins is through mutagenesis. Mutagenesis refers to altering the amino acid that naturally occurs at a position along the string of amino acids that create a given protein. Systematically altering amino acids at different positions through mutagenesis can identify those amino acids that are essential to the function of the protein. Deep mutational scanning refers to methods of generating and characterizing hundreds of thousands of mutants or more of a given protein. More particularly, deep mutational scanning can refer to altering each amino acid position with all possible alternative amino acids. More particularly, deep mutational scanning can refer to altering each amino acid position with all possible alternative amino acids.

One scenario where the study of proteins is extremely beneficial is in relation to viruses. Many viruses can be effectively managed or treated. For example, vaccination has all but ameliorated smallpox and measles, once among mankind's greatest scourges. Unfortunately, however, numerous viruses continue to pose significant health threats. Examples include influenza, human immunodeficiency virus (HIV), Ebola virus, and Middle Eastern respiratory syndrome coronavirus (MERS-CoV).

To combat the spread of viruses, scientists and doctors need tools to know when therapeutic treatments (e.g., drugs, vaccines, or antibodies) are working against viral proteins, or conversely, when these viral proteins have developed resistance to therapeutics and pose a greater risk.

Replication of retroviruses, a type of virus that has an RNA genome, has been well studied. Once a retrovirus gains entry into a host cell, the viral RNA genome is copied by specialized enzymes into a DNA form that then goes to the nucleus of the host cell, where the host cell genome resides. The viral DNA integrates itself into the host cell genome. The ends of the viral RNA genome are flanked by regions of sequences called long terminal repeats (LTRs), which facilitate this integration, along with the virion integrase. The number of possible sites of integration into the cellular genome is very large and widely distributed. Cellular enzymes are used for replication of the integrated viral DNA in concert with cellular chromosomal DNA, and cellular RNA polymerase II is used for expression of the integrated viral DNA. A region of the LTR called the U3 is important for a process called transcription, where the integrated DNA form of the retrovirus is converted back to a messenger RNA (mRNA) form. After synthesis of viral mRNA, the mRNA is exported out of the nucleus into the host cell cytoplasm where this mRNA can be used in a process called translation to produce more of the viral proteins that then are assembled along with the retroviral genome into new virions. The new virions bud off from the cell to start a new cycle of infection.

In the context of viral infection, years of research has led to an understanding of many of the proteins important in the virus life cycle. A virion is a complete infective form of a virus outside of a host's cell. The first step in viral infection is binding of the virion's viral entry protein to a host cell. This binding is followed by fusion of the virion with the host cell. For many human pathogenic viruses, the binding and fusion steps are performed by a single viral entry protein. For example, influenza virus, HIV, Ebola virus, and Lassa virus, all use a single entry protein for binding and fusion with a host cell. For other viruses, multiple proteins are involved. For example, Nipah virus has separate binding and fusion proteins.

Viral entry proteins are a primary target of immune system responses against infection. Most vaccines elicit neutralizing antibodies to the viral entry protein. Therapeutic antibodies can also be used to impair the activity of viral entry proteins, with the potential to both protect against infection as well as therapeutically treat active infection. However, viral entry proteins are able to mutate and evolve over time, and mutations can allow these proteins to escape recognition by immune system responses and therapeutic antibodies. Evasion or susceptibility to antibodies can be examined using mutant viral entry proteins in antibody neutralization assays.

A virus' viral entry protein is also a key determinant of the species that the particular virus can infect, and adaptive evolution of these entry proteins has been retrospectively characterized in most molecularly documented examples of non-human viruses jumping into humans. For example, the influenza pandemics of 1918, 1957, and 1968 all involved mutations that turned viral entry proteins from avian viral strains to strains that could better infect humans. The severe acute respiratory syndrome (SARS) coronavirus outbreak in 2003 was associated with mutations in the virus's entry protein that enabled it to better bind human receptors. The MERS-CoV viral entry protein has mutations that increase binding to human cells. Recent evidence also suggests that during the 2014-2016 Ebola outbreak, this virus's entry protein acquired mutations that promoted infection of human cells. Comparing the growth of viral mutants in different cell types can serve to identify mutations that contribute to host adaptation.

Therefore, it would be incredibly useful to identify particular amino acids within a viral entry protein that are important for binding and fusion to host cells and/or antibody evasion. The entry proteins of a few viruses (e.g., influenza, HIV) are well-characterized, but surprisingly little is known about the entry proteins of many less-studied viruses in part because these proteins are challenging to study. They form large metastable oligomers that are often heavily modified with sugar molecules which render them difficult targets for biochemistry and structural biology.

Figures 1, 2:
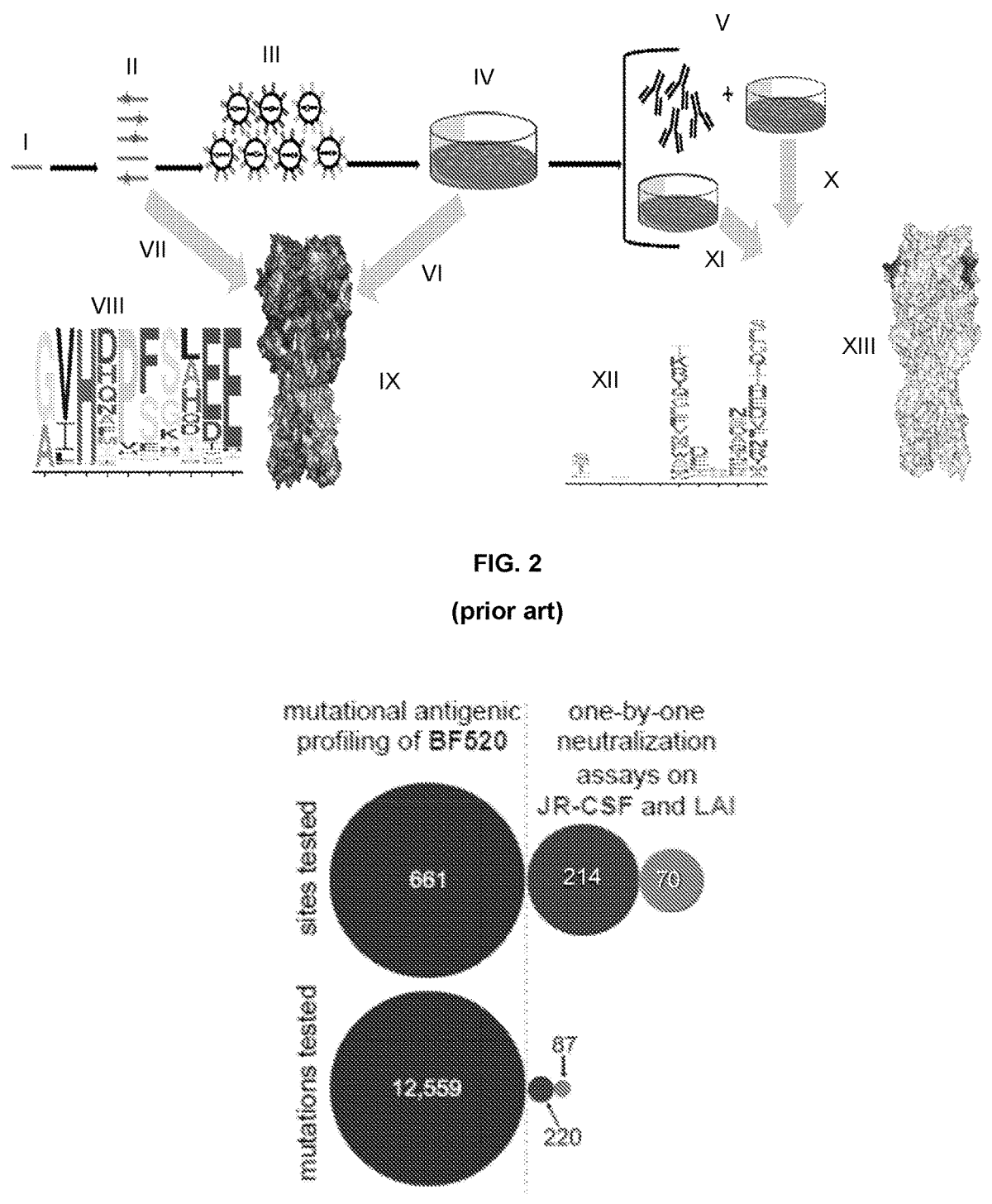

Deep mutational scanning has been used to completely map functional and antigenic effects of all mutations to the entry proteins of influenza virus and HIV. For example, FIG. 1 outlines an approach that was used to characterize mutations to the influenza entry protein, hemagglutinin (HA) and the HIV entry protein, Env. Briefly, all codon mutants of the genes encoding HA or Env were created and all associated replication-competent viruses were generated. These viruses were passaged in cell culture and deep sequencing was used to quantify the frequency of every mutation in the passaged viruses versus the original pool to estimate the preference of each site for each amino acid (FIG. 1). The results of these experiments were informative for understanding the evolution of influenza and HIV in nature. The approach was also used to completely map how single amino acid mutations affect antibody neutralization. As shown in FIG. 1, the virus libraries were subjected to antibody or mock neutralization before infection into cells, and deep sequencing was used to identify mutations enriched by antibody selection. The results precisely pinpointed antibody epitopes and which specific mutations escape from antibody neutralization (FIG. 1).

The work described in relation to FIG. 1 garnered substantial notice. Kepler (2017) Cell Host & Microbe 21: 659-660; Moncla, et al. (2017) Trends in Microbiology 25: 432-434. For instance, Kepler stated: "Let's pause here to appreciate the advance in experimental power ushered in with this method. The investigators measured the effect of 12,559 distinct mutations . . . . The raw increase in numbers is crucial because it matches the extraordinary connectivity of the genotype space". And indeed, the scale of measurements vastly outstripped what was previously possible as shown in FIG. 2. Unfortunately, however, the applicability and utility of this described approach remained severely limited. While informative, these mutagenesis experiments were too low-throughput to keep up with the many relevant questions when studying rapidly evolving viruses that sample all possible mutations within a single human infection.

The approach depicted in FIG. 1 was advantageous because it directly measured viral infection or antibody neutralization. This contrasts with many high-throughput approaches that are currently available that measure surrogate viral activities like protein abundance or binding. Directly measuring infection or antibody neutralization is important because the functions of entry proteins are far more complex than can be inferred based on surrogate activities. However, performing functional experiments with replication-competent viruses has downsides. First, generating the virus libraries is complicated, with different challenges for every virus. FIG. 3 shows one process to generate diverse libraries of influenza viruses and processes for generating libraries of HIV is similarly complex. To create a library containing mutated DNA sequences encoding mutant influenza viral entry proteins with all possible amino acid mutations at each amino acid residue position, a molecular technique called polymerase chain reaction (PCR) using tiling mutagenic oligonucleotides, or short nucleic acid molecules containing all possible mutations, can be performed to generate the mutated DNA sequences. Each mutated DNA sequence that is created by this PCR then has to be inserted into plasmids, small circular, double-stranded DNA molecules that allow propagation of the mutated DNA sequences in an organism that serves as a factory to make more copies of the mutated DNA sequences. A typical organism used for this purpose is bacteria. The plasmid library thus made contains a large number of mutated DNA sequences encoding mutant viral entry proteins and can be stored and used in steps described below. Multiple plasmid libraries are typically generated, and each library has to be carried through subsequent steps independently to ensure statistical rigorousness. To determine mutations that are present in each mutated DNA sequence in a plasmid library and to be able to associate the mutations with viral entry protein functionality, further steps need to be performed with each plasmid library. First, virus particles (virions) having these mutated viral entry proteins on their surface need to be produced. Virions typically have two or three main parts: (i) a genome of DNA or RNA, which has genetic instructions for making new virions; (ii) a protein coat, called the capsid, which surrounds and protects the genome; and in some cases, (iii) an envelope of lipids, or fatty molecules, that surrounds the protein coat. The production of virions is achieved by bringing together viral components in cells capable of forming the virions. Cells that are typically used are eukaryotic cells such as mammalian cells. A process called transfection introduces into these cells the library plasmids, along with plasmids that allow expression of other viral proteins (such as proteins PA, PB1, PB2, and NP in FIG. 3). The transfection step allows the formation of complexes of viral proteins and nucleotide segments derived from the plasmid library encoding mutant viral entry proteins inside the mammalian cells. Then the cells that have these complexes are infected with a helper virus that is deficient for the viral entry protein being studied but containing any other necessary viral genome segments to produce fully competent virions. These virions, making up a mutant viral entry protein library, are then used to perform a second infection of appropriate cells, such as mammalian cells, at a low multiplicity of infection (MOI). A low MOI allows better selection of functional mutants and a link between a mutant viral entry protein found on the surface of a virion (phenotype) and the gene segment encoding the mutant viral entry protein (genotype) in the virion. Then sequencing is performed on library plasmids to assess initial mutation frequencies and on viral DNA from infected cells to assess mutation frequencies after virions have been passaged through the mammalian cells. Moreover, each mutant library is paired with a control in which cells are transfected with a plasmid having a non-mutagenized (wild type) viral entry DNA sequence to generate initially wild type virions that are passaged in parallel with the mutant virions. Sequencing of the control allows for estimation of and statistical correction due to rates of apparent mutations arising from sources other than the original PCR mutagenesis, such as during sequencing and/or viral replication.

To achieve the results for influenza described in FIG. 3 and similar experiments for HIV, years of prior work were leveraged. For example, these experiments took advantage of the development of robust reverse genetics systems (approaches to generate virus from plasmid DNA), the ability to carefully control growth kinetics of these viruses in cell culture, the ability to grow these viruses to high titer and in large volumes, and various molecular tools to characterize the resulting virus. However, comparable molecular virology tools do not exist for most viruses. Moreover, virus libraries generated by plasmid transfection lack a genotype-phenotype link, and so must be passaged at a low MOI to create such a link (FIG. 3). Acceptable results can be obtained with a MOI ≤0.01 which requires >$10^8$ cells to maintain a diversity of $10^6$. Handling this many cells is problematic because viruses require biosafety containment. This is difficult but manageable for influenza and HIV, which can be worked with at biosafety level (BSL)-2/2+ conditions—but becomes almost unthinkable for BSL-3/4 viruses such as Ebola or MERS-CoV.

At BSL-2, all precautions used at BSL-1 are followed, which include laboratory personnel washing their hands upon entering and exiting the lab, prohibition of eating and drinking in laboratory areas, decontamination of potentially infectious material by adding an appropriate disinfectant or by packaging for decontamination elsewhere before disposal, and having a door which can be locked to limit access to the lab. Some additional precautions taken at BSL-2 include: training laboratory personnel to handle pathogenic agents; supervision of laboratory personnel by scientists with advanced training; limiting access to the laboratory when work is being conducted; taking extreme precautions with contaminated sharp items; and conducting procedures in which infectious aerosols or splashes may be created in biological safety cabinets or other physical containment equipment. BSL-2 can be suitable for work involving agents of moderate potential hazard to personnel and the environment. This includes various microbes that cause mild disease to humans or are difficult to contract via aerosol in a lab setting. Examples include Hepatitis A, B, and C viruses, human immunodeficiency virus (HIV), pathogenic *Escherichia coli*, *Staphylococcus aureus*, *Salmonella*, *Plasmodium falciparum*, and *Toxoplasma gondii*.

BSL-3 can be appropriate for work involving microbes which can cause serious and potentially lethal disease via the inhalation route. This type of work can be done in clinical, diagnostic, teaching, research, or production facilities. Here, the precautions undertaken in BSL-1 and BSL-2 labs are followed, as well as additional measures including: providing medical surveillance and relevant immunizations to all laboratory personnel to reduce the risk of an accidental or unnoticed infection; performing all procedures involving infectious material within a biological safety cabinet; the use of solid-front protective clothing (i.e. gowns that tie in the back) by laboratory personnel that must be discarded or decontaminated after each use; and drafting a laboratory-specific biosafety manual which details how the laboratory will operate in compliance with all safety requirements. In addition, the facility which houses the BSL-3 laboratory must have certain features to ensure appropriate containment. The entrance to the laboratory must be separated from areas of the building with unrestricted traffic flow. Additionally, the laboratory must be behind two sets of self-closing doors to reduce the risk of aerosols escaping. The construction of the laboratory is such that it can be easily cleaned. Carpets are not permitted, and any seams in the floors, walls, and ceilings are sealed to allow for easy cleaning and decontamination. Additionally, windows must be sealed, and a ventilation system installed which forces air to flow from the "clean" areas of the lab to the areas where infectious agents are handled. Air from the laboratory must be filtered before it can be recirculated. BSL-3 is commonly used for research and diagnostic work involving various microbes which can be transmitted by aerosols and/or cause severe disease. These include *Francisella tularensis, Mycobacterium tuberculosis, Chlamydia psittaci*, Venezuelan equine encephalitis virus, Eastern equine encephalitis virus, SARS coronavirus, *Coxiella burnetii*, Rift Valley fever virus, *Rickettsia rickettsii*, several species of *Brucella*, chikungunya, yellow fever virus, and West Nile virus. BSL-4 is the highest level of biosafety precautions and can be appropriate for work with agents that could easily be aerosol-transmitted within the laboratory and cause severe to fatal disease in humans for which there are no available vaccines or treatments.

BSL-4 laboratories are generally set up to be either cabinet laboratories or protective-suit laboratories. In cabinet laboratories, all work must be done within a class III biosafety cabinet. Materials leaving the cabinet must be decontaminated by passing through an autoclave or a tank of disinfectant. The cabinets themselves are required to have seamless edges to allow for easy cleaning. Additionally, the cabinet and all materials within must be free of sharp edges to reduce the risk of damage to the gloves. In a protective-suit laboratory, all work must be done in a class II biosafety cabinet by personnel wearing a positive pressure suit. To exit the BSL-4 laboratory, personnel must generally pass through a chemical shower for decontamination, then a room for removing the positive-pressure suit, followed by a personal shower. Entry into the BSL-4 laboratory is restricted to trained and authorized individuals, and all persons entering and exiting the laboratory must be recorded. As with BSL-3 laboratories, BSL-4 laboratories must be separated from areas that receive unrestricted traffic. Additionally, airflow is tightly controlled to ensure that air always flows from "clean" areas of the lab to areas where work with infectious agents are being performed. The entrance to the BSL-4 lab must also employ airlocks to minimize the possibility that aerosols from the lab could be removed from the lab. All laboratory waste, including filtered air, water, and trash must also be decontaminated before it can leave the facility. BSL-4 laboratories are used for diagnostic work and research on easily transmitted pathogens which can cause fatal disease. These include a number of viruses known to cause viral hemorrhagic fever such as Marburg virus, Ebola virus, Lassa virus, Crimean-Congo hemorrhagic fever. Other pathogens handled at BSL-4 include Hendra virus, Nipah virus, and some Flaviviruses. Additionally, poorly characterized pathogens which appear closely related to dangerous pathogens are often handled at this level until sufficient data are obtained either to confirm continued work at this level, or to work with them at a lower level. This level is also used for work with Variola virus, the causative agent of smallpox, though this work can only be done at World Health Organization approved facilities.

Another challenge is the deep sequencing required for this type of work. There is now substantial literature on sequencing methods for deep mutational scanning. The key point is that sequencing methods that are currently used (e.g., Illumina sequencing) can sequence nucleotide sequences with average read lengths of 30-1000 bases but have an error rate that is too high to produce informative and reliable results. Alternative methods (such as PacBio) can sequence nucleotide sequences with average read lengths of 10,000 to 15,000 bases but lack the throughput and/or accuracy to efficiently (and affordably) characterize diverse libraries at multiple conditions. One solution is to associate each variant in a library with a unique nucleotide barcode [Hiatt, et al. (2010) Nat Methods 7: 119-122] by using a sequencing method that can yield long, accurate read lengths (e.g. PacBio sequencing). The barcodes can then be sequenced using a sequencing method that is more high-throughput and sufficiently accurate for barcode-length reads (e.g., Illumina). The combination of sequencing to associate a unique barcode with each variant in a library and sequencing of barcodes can yield the library composition. This approach is efficient and cheap and provides a linkage between barcode and variant. Unfortunately, however, standard barcoding, without more, does not work for many viruses for at least two reasons: First, the compactness of viral genomes means that it is hard to insert nucleotide barcodes without affecting fitness. Second, many viruses have high rates of recombination which often decouple barcodes from their variant sequence. Therefore, approaches to date have attached unique molecular identifiers (UMIs or barcodes) to PCR subamplicons each time the library is sequenced. Each mutated DNA sequence encoding a mutant viral entry protein can be divided into fragments to be sequenced. A barcode can be a random stretch of nucleotides that serves as a unique tag to identify a DNA molecule that is sequenced, and two different barcodes can be incorporated by PCR into a DNA molecule, one barcode at each end of the DNA molecule. In the context of sequencing mutated DNA sequences present in a viral entry protein library, PCR is performed to generate PCR subamplicons, which are many copies of each fragment of a mutated DNA sequence, containing barcodes at the ends of the subamplicons. The barcoded subamplicons are then sequenced. This approach requires a lot of sequencing because each barcoded subamplicon must be sequenced multiple times for error correction. A barcode is useful because repeated identification of a barcode during sequencing reveals resampling of a DNA molecule associated with that barcode. The output of a sequencing is sequence reads, which are strings of nucleotides for every DNA fragment of every mutated DNA sequence. Sequence reads with the same barcode can then be grouped together and differences among the sequence reads in a given barcode family can be readily detected. Differences in sequences at a given nucleotide position can represent true viral entry protein mutations if they occur in the majority of the sequence reads, while non-relevant mutations arising from errors due to experimental processes such as PCR and sequencing can occur in a minority of the reads. This approach also does not provide linkage information among mutations in different subamplicons, as subamplicons making up a given mutated DNA sequence in a library are generated and sequenced separately, thus losing linkage among multiple mutations that may occur along the complete length of a mutated DNA library sequence. Thus, there is significant room for improvement in the ability to create and assess deep mutational scanning libraries of viral entry proteins.

Described herein is a new approach for performing deep mutational scanning of proteins. The current disclosure provides cell-stored barcoded mutational scanning libraries of proteins. The libraries can be used to predict viruses that may become resistant to antibody neutralization or drug inhibition, and/or that may more easily evolve to infect new species. The libraries can also be used to more safely study dangerous viruses that normally require high safety biocontainment facilities. The libraries include features that allow efficient collection and assessment of informative data, obviating many bottlenecks of previous approaches.

For example, systems and methods disclosed herein overcome inefficiencies associated with deep sequencing by providing new methods of associating barcodes with variant protein sequences within a library. The new association methods avoid loss of the original link between barcode and variant sequence due to recombination. This is achieved by creating virions that enter cells only once, thus not allowing a full replication cycle and limiting opportunities for recombination. Additionally, each cell of a cell-stored barcoded deep mutational scanning library contains at most one variant sequence integrated, so virions produced from each cell include retroviral genomes where the two copies of a variant sequence are identical. Therefore, even when recombination occurs, the link between barcode and variant sequence is maintained. Because the barcode-variant sequence link is maintained, standard sequencing can be utilized to sequence only the barcodes, greatly enhancing the throughput of the systems.

The systems and methods overcome biosafety and containment considerations by storing the library of genes encoding variant proteins in a non-infective state within holding cells. More particularly, the library is stored as barcoded non-replicative variants inside cells. A storage cell includes a non-self-inactivating viral vector integrated into the storage cell's genome, where the non-self-inactivating viral vector includes a single homozygous barcoded variant nucleotide sequence from a set of barcoded variant nucleotide sequences that encode viral protein variants forming a deep mutational scanning library of a viral protein. In particular embodiments, integrated viral protein variants in cells are considered non-replicative because expression of viral genes (e.g., gag, pol, env, tat, rev) provided by the transfection of the cells with helper plasmids is needed for production of virions. In particular embodiments, virions produced from transfection of cells storing a barcoded deep mutational scanning library of protein variants are non-replicative because the genome of each virion does not contain the full complement of viral genes needed for replication. In particular embodiments, the variant proteins are viral entry proteins. In particular embodiments, virion production can be induced by transfecting the storing cells with viral helper plasmids that encode the rest of the retroviral particle proteins. This results in expression in each cell of retroviral particles that are packaged with a barcoded gene encoding a given mutant viral entry protein and pseudotyped with that particular mutant viral entry protein. The ability to produce virions that package a barcoded gene encoding a mutant viral entry protein following transfection with helper plasmids is achieved, in part, through use of a vector that is not self-inactivating. In particular embodiments, this is achieved by including a functional U3.

Following generation of virions from the storage cells, functional studies can be conducted to assess variant proteins. In particular embodiments, the systems and methods disclosed herein can be used to map quickly and with high resolution amino acid changes in a given protein that are important to escape binding to a ligand. This application is valuable in situations such as immunotherapy that depend upon binding of antibodies, chimeric antigen receptors (CARs), or other ligands to target proteins for killing of diseased cells. In particular embodiments, the systems and methods disclosed herein can be used to map the epitopes of antibodies. In particular embodiments, the systems and methods disclosed herein can be used to inform antibody drug development by characterizing mutations in target proteins that allow development of resistance to antibodies. In particular embodiments, the systems and methods disclosed herein can be used to assess the ability of different viral entry proteins to evade antibody neutralization, overcome drug inhibition, and/or infect new species. If numerous mutations to a viral entry protein allow antibody evasion, drug resistance, or infection of a new host species, the virus may have a higher probability of becoming a health threat. If, however, only few or very specific mutations allow antibody evasion, drug resistance, or infection of a new host species, the virus may pose less of a threat.

Taken together, the disclosed cell-stored barcoded mutational scanning libraries of proteins provide an important advance in the ability to generate, store, and characterize a large number of variant proteins. In particular embodiments, the libraries allow development of antibody therapeutics. In particular embodiments, the libraries allow study and control of viruses and viral outbreaks.

Schematics of the described approach are depicted in FIGS. 4A-4D and 5. FIGS. 4A-4D depict exemplary lentiviral backbone constructs that can be used. However, one of ordinary skill in the art will know that any retroviral backbone may be used in the systems and methods of the present disclosure and additional description and detail regarding these options are provided below. In particular embodiments, each genetic construct includes a codon-variant that encodes a viral entry protein. Exemplary methods to create a library of codon-variants expressing viral entry proteins are described below.

In particular embodiments, deep mutational scanning combines functional selection with high throughput sequencing to measure the effects of mutations on protein function. In particular embodiments, a library of $10^4$ to $10^5$ variants of a given protein is constructed and selection for function is imposed. Under modest selection pressure, variant frequencies are perturbed according to the function of each variant. Variants harboring beneficial mutations increase in frequency, whereas variants harboring deleterious mutations decrease in frequency. In particular embodiments, high throughput sequencing can measure the frequency of each variant during the selection experiment, and a functional score can be calculated from the change in frequency over the course of the experiment. In particular embodiments, the result is a largescale mutagenesis data set containing a functional score for each variant in the library. Fowler et al. (2014) Nature Protocols 9: 2267-2284.

In particular embodiments, the selection pressure is heat. Heat can include temperatures above 25° C., above 26° C., above 27° C., above 28° C., above 29° C., above 30° C., above 31° C., above 32° C., above 33° C., above 34° C., above 35° C., above 36° C., above 37° C., above 38° C., above 39° C., above 40° C., above 41° C., above 42° C., above 43° C., above 44° C., above 45° C., above 46° C., above 48° C., above 49° C., above 49° C., above 50° C., or more. In particular embodiments, heat can include temperatures from 28° C. to 70° C. In particular embodiments, heat can include temperatures from 30° C. to 65° C. In particular embodiments, heat can include temperatures above 30° C. In particular embodiments, the selection pressure is cold. Cold can include temperatures below 25° C., below 24° C., below 23° C., below 22° C., below 21° C., below 20° C., below 19° C., below 18° C., below 17° C., below 16° C., below 15° C., below 14° C., below 13° C., below 12° C., below 11° C., below 10° C., below 9° C., below 8° C., below 7° C., below 6° C., below 5° C., below 4° C., below 3° C., below 2° C., below 1° C., below 0° C., or lower. In particular embodiments, cold can include temperatures from 22° C. to 0° C. In particular embodiments, cold can include temperatures from 20° C. to 4° C. In particular embodiments, cold can include temperatures below 20° C. In particular embodiments, the selection pressure is low pH. Low pH can include pH of 6.9, 6.5, 6.0, 5.5, 5.0, 4.5, 4.0, 3.5, 3.0, 2.5, 2.0, or lower. In particular embodiments, low pH can be from pH of 6.8 to 2.0. In particular embodiments, low pH can be from pH of 6.5 to 3.0. In particular embodiments, low pH can include a pH below 6.5. In particular embodiments, the selection pressure is high pH. High pH can include pH of 7.5, 7.6, 7.7, 7.8, 7.9, 8.0, 8.5, 9.0, 9.5, 10.0, 10.5, 11.0, 11.5, 12.0, or higher. In particular embodiments, high pH can include pH of 8.0 to 14.0. In particular embodiments, high pH can include pH of 8.5 to 12.0. In particular embodiments, high pH can include a pH above 8.0. In particular embodiments, the selection pressure is a toxic agent. Toxic agents can include polar organic solvents (e.g., dimethylformamide), herbicides (e.g., glyphosate), pesticides (e.g., malathion, dichlorodiphenyltrichloroethane), salinity, ionizing radiation, and hormonally active phytochemicals (e.g., flavonoids, lignins and lignans, coumestans, or saponins).

In particular embodiments, a deep mutational scanning library includes variants with 19 possible amino acid substitutions at each amino acid position and all possible codons of the associated 63 codons at each amino acid position. In particular embodiments, a deep mutational scanning library includes variants with every possible codon substitution at every amino acid position in a gene of interest with one codon substitution per library member. In particular embodiments, a deep mutational scanning library includes variants with one, two, or three nucleotide changes for each codon at every amino acid position in a gene of interest with one codon substitution per library member. In particular embodiments, a deep mutational scanning library includes variants with one, two, or three nucleotide changes for each codon at two amino acid positions, at three amino acid positions, at four amino acid positions, at five amino acid positions, at six amino acid positions, at seven amino acid positions, at eight amino acid positions, at nine amino acid positions, at ten amino acid positions, etc., up to at all amino acid positions, in a gene of interest with one codon substitution per library member. In particular embodiments, the start codon is not mutagenized. In particular embodiments, the start codon is Met.

In particular embodiments, a deep mutational scanning library includes variants with one, two, or three nucleotide changes for each codon at every amino acid position in a gene of interest with more than one codon substitution, more than two codon substitutions, more than three codon substitutions, more than four codon substitutions, or more than five codon substitutions, per library member. In particular embodiments, a deep mutational scanning library includes variants with one, two, or three nucleotide changes for each codon at every amino acid position in a gene of interest with up to all codon substitutions per library member. In particular embodiments, 20% of library members can be wildtype, 35% can be single mutants, and 45% can be multiple mutants. Multiple mutants can be advantageous, and the sequencing required by the systems and methods disclosed herein is so efficient that using 20% of reads on wildtype is not a problem. Additionally, there are alternative (more complex) mutagenesis methods that give a larger proportion of single amino acid mutants [see, e.g., Kitzman, et al. (2015) Nature Methods 12: 203-206; Firnberg & Ostermeier (2012) PLoS One 7: e52031; Jain & Varadarajan (2014) Analytical Biochemistry 449: 90-98; and Wrenbeck, et al. (2016) Nature Methods 13: 928].

In particular embodiments, a deep mutational scanning library includes or encodes all possible amino acids at all positions of a protein, and each variant protein is encoded by more than one variant nucleotide sequence. In particular embodiments, a deep mutational scanning library includes or encodes all possible amino acids at all positions of a protein, and each variant protein is encoded by one nucleotide sequence. In particular embodiments, a deep mutational scanning library includes or encodes all possible amino acids at less than all positions of a protein, for example at 10%, 20%, 30%, 40%, 50%, 60%, 70%, 80%, 90%, 95%, 96%, 97%, 98% or 99% of positions. In particular embodiments, a deep mutational scanning library includes or encodes less than all possible amino acids (for example 10%, 20%, 30%, 40%, 50%, 60%, 70%, 80%, 90%, 95%, 96%, 97%, 98% or 99% of potential amino acids) at all positions of a protein. In particular embodiments, a deep mutational scanning library includes or encodes less than all possible amino acids (for example 10%, 20%, 30%, 40%, 50%, 60%, 70%, 80%, 90%, 95%, 96%, 97%, 98% or 99% of potential amino acids) at less than all positions of a protein, for example at 10%, 20%, 30%, 40%, 50%, 60%, 70%, 80%, 90%, 95%, 96%, 97%, 98% or 99% of positions. In particular embodiments, a deep mutational scanning library including a set of variant nucleotide sequences can collectively encode protein variants including at least a particular number of amino acid substitutions at at least a particular percentage of amino acid positions. "Collectively encode" takes into account all amino acid substitutions at all amino acid positions encoded by all the variant nucleotide sequences in total in a deep mutational scanning library.

In particular embodiments, a codon-mutant library can be generated by PCR, primer-based mutagenesis, as described in Example 1 and in US2016/0145603. In particular embodiments, a codon-mutant library can be synthetically constructed by and obtained from a synthetic DNA company such as Twist Bioscience (San Francisco, CA). In particular embodiments, methods to generate a codon-mutant library include: nicking mutagenesis as described in Wrenbeck et al. (2016) Nature Methods 13: 928-930 and Wrenbeck et al. (2016) Protocol Exchange doi:10.1038/protex.2016.061; PFunkel (Firnberg & Ostermeier (2012) PLoS ONE 7(12): e52031); massively parallel single-amino-acid mutagenesis using microarray-programmed oligonucleotides (Kitzman et al. (2015) Nature Methods 12: 203-206); and saturation editing of genomic regions with CRISPR-Cas9 (Findlay et al. (2014) Nature 513(7516): 120-123).

Supporting the description of creating codon-mutant libraries, the following information is provided for viral entry proteins for influenza, Ebola, MERS-CoV, Lassa virus, and Nipah virus. These examples are provided so that one of ordinary skill in the art can apply the teachings of the current disclosure to additional viral entry proteins.

Influenza. Hemagluttinin (HA) is 566 codons long, so there are 566×63=35,658 codon mutations corresponding to 566×19=10,754 amino acid mutations. The number of mutations per clone from the mutagenesis method follows a Poisson distribution, and an average of 1.5 mutations can be introduced per clone and libraries of $5 \times 10^5$ clones can be created. Therefore, $1.7 \times 10^5$ of the clones will be single mutants, and $2.2 \times 10^5$ will be multiple mutants. The typical single-codon mutant will thus be represented by 5 clones, and with Poisson statistics 99% of single-codon mutants should be captured in at least one clone. The typical single amino acid mutant will be represented by 15 clones, although this will vary among amino acids with different codon degeneracies. In particular embodiments, HA from A/Perth/16/2009 (H3N2), a recent component of the influenza vaccine can be used to generate a codon-mutant library with barcodes for HA.

Ebola Virus. The Ebola virus entry protein GP is 676 residues, so the libraries can be created with diversity $6 \times 10^5$ to maintain the mutation statistics. In particular embodiments, it can be desirable to study virion-associated GP, and so mutations can be introduced at the gene's adenosine repeat to eliminate polymerase stuttering to produce full pre-GP but not secreted forms [Lee & Saphire (2009) Future Virology 4: 621-635]. In particular embodiments, GPs from the Makona and Kitwit viral strains can be used. The GP of the Kitwit strain is in the VSV-EBOV vaccine [Jones, et al. (2005) Nature Medicine 11: 786]. The Makona strain is from the 2014-2016 outbreak in Guinea [Marzi, et al. (2015) Science 349: 739-742].

MERS-CoV. The MERS-CoV entry protein, Spike, is 1,353 residues, necessitating library diversity of $1.2 \times 10^6$. In particular embodiments, Spike from strains HCoV-EMC/2012 and camel/Qatar/2/2014 can be used. The first strain has been used in animal studies [De Wt, et al. (2013) Proceedings of the National Academy of Sciences 110: 16598-16603], and the second strain is the source of the Spike in the adenovirus vaccine described in Munster, et al. (2017) NPJ vaccines 2: 28.

Lassa Virus. The Lassa virus entry protein, GPC, is 490 residues, so a library diversity of $5 \times 10^5$ is sufficient. GPC from the AV and Josiah strains can be used; the former is a low-passage human isolate [Gunther, et al. (2000) Emerging Infectious Diseases 6: 466-476] while the latter is the source of the GPC in a VSV-based vaccine [Geisbert, et al. (2005) PLoS Medicine 2: e183].

Nipah virus. Nipah virus has separate attachment and fusion proteins (G and F), which can simultaneously be used to enable lentiviral infection [Khetawat & Broder (2010) Virology Journal 7: 312; Witting, et al. (2013) Gene Therapy 20: 997]. In particular embodiments G can be the focus of study because it determines receptor specificity and will co-transfect F when generating the virions from the cells that store the G library. In particular embodiments, G from the Malaysia and Bangladesh strains can be used [DeBuysscher, et al. (2013) PLoS Neglected Tropical Diseases 7: e2024].

As shown in FIGS. 4A-4F, each variant sequence can be associated with a barcode. In particular embodiments, the barcode is 18-nucleotides in length. In particular embodiments, because there are $4^{18}$-$7^{10}$ different 18-nucleotide sequences, virtually every variant can have a unique barcode. The barcode can be any appropriate length and composition that does not negatively affect fitness of the encoded variant protein. In particular embodiments, the length of the barcode is based upon the size of the deep mutation scanning library. If more distinct barcodes are needed, then barcodes of greater length can be used. If less distinct barcodes are needed, then barcodes of lesser length can be used. In particular embodiments, the barcode can be 5-100 nucleotides in length. In particular embodiments, the barcode can be 10-80 nucleotides in length. In particular embodiments, the barcode can be 10-50 nucleotides in length. In particular embodiments, the barcode can be 8-30 nucleotides in length. In particular embodiments, the barcode can be 12-24 nucleotides in length. In particular embodiments, the barcode can be 16-20 nucleotides in length. In particular embodiments, the barcode can be 3 nucleotides in length, 4 nucleotides in length, 5 nucleotides in length, 6 nucleotides in length, 7 nucleotides in length, 8 nucleotides in length, 9 nucleotides in length, 10 nucleotides in length, 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, 30 nucleotides in length, 31 nucleotides in length, 32 nucleotides in length, 33 nucleotides in length, 34 nucleotides in length, 35 nucleotides in length, 36 nucleotides in length, 37 nucleotides in length, 38 nucleotides in length, 39 nucleotides in length, 40 nucleotides in length, or more.

In particular embodiments, the barcode can be positioned anywhere within the retroviral genetic construct that is integrated into a cell's genome. In particular embodiments, the barcode can be positioned upstream (5') of the gene encoding a variant protein. In particular embodiments, the barcode can be positioned within the gene encoding a variant protein. In particular embodiments, the barcode can be positioned downstream (3') of the gene encoding a variant protein. In particular embodiments, the barcode can be positioned after the stop codon. In particular embodiments, the barcode can include random nucleotides flanked by priming sequences (e.g., Illumina priming sequences). In the systems and methods of the present disclosure, a barcode is transcribed, packaged into retroviral particles, and enters a cell once. In particular embodiments, this process is mostly separate from the rest of the viral genome. In particular embodiments, a barcode is integrated into a cell's genomic DNA, along with the gene encoding a variant protein, and is thus not a part of a replicating virus' genome. In particular embodiments, the barcode does not affect viral fitness because the retroviral particles do not go through a full replication cycle.

As indicated in FIGS. 4A-4F, integration of the construct can be marked with a reporter or selectable marker. In particular embodiments, the reporter is green fluorescent protein (GFP). However, as is understood by those or ordinary skill in the art, any appropriate reporter or selectable marker can be used. Additional examples include blue fluorescent proteins (e.g. eBFP, eBFP2, Azurite, mKalamal, GFPuv, Sapphire, T-sapphire); cyan fluorescent proteins (e.g. eCFP, Cerulean, CyPet, AmCyanl, Midoriishi-Cyan); additional green fluorescent proteins (e.g. GFP-2, tagGFP, turboGFP, eGFP, Emerald, Azami Green, Monomeric Azami Green, CopGFP, AceGFP, ZsGreenl); orange fluorescent proteins (mOrange, mKO, Kusabira-Orange, Monomeric Kusabira-Orange, mTangerine, tdTomato); red fluorescent proteins (mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred); yellow fluorescent proteins (e.g., YFP, eYFP, Citrine, Venus, YPet, PhiYFP, ZsYellowl); and any other suitable fluorescent proteins, including, for example, firefly luciferase. In particular embodiments, the reporter or selectable marker can include any cell surface displayed marker that can be detected with an antibody that binds to that marker and allows sorting of cells that have the marker. In particular embodiments, the reporter or selectable marker can include the magnetic sortable marker streptavidin binding peptide (SBP) displayed at the cell surface by a truncated Low Affinity Nerve Growth Receptor (LNGFRF) and one-step selection with streptavidin-conjugated magnetic beads (Matheson et al. (2014) PloS one 9(10): e111437).

Particular embodiments can also utilize cerulenin resistance genes (e.g., fas2m, PDR4; Inokoshi et al., Biochemistry 64: 660, 1992; Hussain et al., Gene 101: 149, 1991); copper resistance genes (CUP1; Marin et al., Proc. Natl. Acad. Sci. USA. 81: 337, 1984); and geneticin resistance gene (G418r) as markers. However, one of ordinary skill in the art will appreciate that the systems and methods described herein can be made, performed, and used without a reporter or selectable marker. Absence of a reporter or selectable marker, however, decreases the efficiency of the disclosed systems and methods.

Additional useful selectable markers include β-galactosidase (β-gal) and β-glucuronidase (GUS) (see, e.g., European Patent Publication EP2423316). These reporter proteins function by hydrolyzing a secondary marker molecule (e.g., a β-galactoside or a β-glucuronide). Thus it will be understood that methods and systems that employ one of these marker proteins will also involve providing the compound(s) needed to produce a detectable reaction product. Assays for detecting β-gal or GUS activity are well known in the art.

In particular embodiments it may be appropriate to use auxotrophic markers as reporters or selectable markers. Exemplary auxotrophic markers include methionine auxotrophic markers (e.g., met1, met2, met3, met4, met5, met6, met7, met8, met10, met13, met14 or met20); tyrosine auxotrophic markers (e.g., tyr1 or isoleucine); valine auxotrophic markers (e.g., ilv1, ilv2, ilv3 or ilv5); phenylalanine auxotrophic markers (e.g., pha2); glutamic acid auxotrophic markers (e.g., glu3); threonine auxotrophic markers (e.g., thr1 or thr4); aspartic acid auxotrophic markers (e.g., asp1 or asp5); serine auxotrophic markers (e.g., ser1 or ser2); arginine auxotrophic markers (e.g., arg1, arg3, arg4, arg5, arg8, arg9, arg80, arg81, arg82 or arg84); uracil auxotrophic markers (e.g., ura1, ura2, ura3, ura4, ura5 or ura6); adenine auxotrophic markers (e.g., ade1, ade2, ade3, ade4, ade5, ade6, ade8, ade9, ade12 or ade15); lysine auxotrophic markers (e.g., lys1, lys2, lys4, lys5, lys7, lys9, lys11, lys13 or lys14); tryptophan auxotrophic markers (e.g., trp1, trp2, trp3, trp4 or trp5); leucine auxotrophic markers (e.g., leu1, leu2, leu3, leu4 or leu5); and histidine auxotrophic markers (e.g., his1, his2, his3, his4, his5, his6, his7 or his8).

Genetic constructs used within the libraries disclosed herein can also include a linker. In particular embodiments, the following linkers can be used:

| Linker | Exemplary Encoding Sequence | Associated Protein Sequence |
| --- | --- | --- |
| thosea asigna virus T2A | (GGCAGCGGC)GAAGGCCGCGGCAGCCTGCT GACCTGCGGCGATGTGGAAGAAAACCCGGGC CCG (SEQ ID NO: 1) | (GSG)EGRGSLLTC GDVEENPGP (SEQ ID NO: 21) |
| porcine teschovirus-1 P2A | (GGCAGCGGC)GCGACCAACTTTAGCCTGCTG AAACAGGCGGGCGATGTGGAAGAAACCCGG GCCCG (SEQ ID NO: 2) | (GSG)ATNFSLLKQA GDVEENPGP (SEQ ID NO: 22) |
| equine rhinitis A virus E2A | (GGCAGCGGC)CAGTGCACCAACTATGCGCTG CTGAAACTGGCGGGCGATGTGGAAAGCAACC CGGGCCCG (SEQ ID NO: 3) | (GSG)QCTNYALLKL AGDVESNPGP (SEQ ID NO: 23) |
| foot-and-mouth disease virus F2A | (GGCAGCGGC)GTGAAACAGACCCTGAACTTT GATCTGCTGAAACTGGCGGGCGATGTGGAAA GCAACCCGGGCCCG (SEQ ID NO: 4) | (GSG)VKQTLNFDLL KLAGDVESNPGP (SEQ ID NO: 24) |
| equine rhinitis B virus 12A | GAAGCAACTTTGTCTACCATTCTGTCTGAGGG TGCCACA AATTTTTCTTTGTTGAAGTTAGCAGGGGATGTT GAACTTAACCCCGGCCCA (SEQ ID NO: 5) | EATLSTILSEGATNF SLLKLAGDVELNPG P (SEQ ID NO: 25) |
| Saffold virus 2A | TTCACTGATTTTTTCAAAGCCGTTAGAGACTAT CATGCTTCTTATTACAAACAGAGACTTCAACAT GACGTTGAAACAAACCCTGGCCCT (SEQ ID NO: 6) | FTDFFKAVRDYHAS YYKQRLQHDVETN PGP (SEQ ID NO: 26) |
| Ljungan virus 2A | TACTTTAATATAATGCACAGTGATGAAATGGAT TTTGCCGGGGGGAAATTTTTGAATCAATGTGG TGATGTGGAAACTAACCCAGGCCCT (SEQ ID NO: 7) | YFNIMHSDEMDFAG GKFLNQCGDVETN PGP (SEQ ID NO: 27) |
| infectious flacherie virus 2A | CCCTCAATTGGTAATGTCGCGCGGACTCTGAC GAGGGCGGAGATTGAGGATGAATTGATTCGT GCAGGAATTGAATCAAATCCTGGACCT (SEQ ID NO: 8) | PSIGNVARTLTRAEI EDELIRAGIESNPGP (SEQ ID NO: 28) |
| Perina nuda picorna-like virus | GGACAAAGGACGACTGAACAGATAGTTACGG CCCAGGGGTGGGTTCCGGATTTGACTGTGGA | GQRTTEQIVTAQG WVPDLTVDGDVES |

-continued

| Linker | Exemplary Encoding Sequence | Associated Protein Sequence |
| --- | --- | --- |
| 2A$_1$ | TGGAGATGTTGAGTCAAATCCCGGACCC (SEQ ID NO: 9) | NPGP (SEQ ID NO: 29) |
| Perina nuda picorna-like virus 2A$_2$ | ACGCGTGGTGGTTTACGACGGCAAAATATTAT TGGTGGTGGGCAGAAGGATTTGACACAAGAT GGTGACATCGAGTCGAATCCTGGGCCC (SEQ ID NO: 10) | TRGGLRRQNIIGGG QKDLTQDGDIESNP GP (SEQ ID NO: 30) |
| Ectropis obliqua picorna-like virus 2A$_1$ | GGACAACGGACAACTGAGCAGATCGTGACTG CACAAGGTTGGGCCCCGGATTTGACACAGGA TGGAGATGTAGAGTCAAACCCCGGCCCC (SEQ ID NO: 11) | GQRTTEQIVTAQG WAPDLTQDGDVES NPGP (SEQ ID NO: 31) |
| Ectropis obliqua picorna-like virus 2A$_2$ | ACACGTGGTGGTTTACAGCGTCAAAACATTAT TGGTGGTGGCCAAAGGGATCTGACTCAAGAT GGCGACATCGAGTCGAACCCCGGCCCA (SEQ ID NO: 12) | TRGGLQRQNIIGGG QRDLTQDGDIESNP GP (SEQ ID NO: 32) |
| Drosophila C virus 2A | CAAGGCATCGGTAAGAAGAATCCGAAACAGG AAGCTGCACGTCAGATGTTGCTCTTGTTATCA GGAGATGTTGAGACTAACCCTGGACCC (SEQ ID NO: 13) | QGIGKKNPKQEAAR QMLLLLSGDVETNP GP (SEQ ID NO: 33) |
| acute bee paralysis virus 2A | ACTGGTTTTTTAAACAAGTTATATCATTGTGGC TCATGGACTGACATATTGTTGTTGTTGTCTGG AGATGTAGAAACCAATCCAGGACCT (SEQ ID NO: 14) | TGFLNKLYHCGSW TDILLLLSGDVETNP GP (SEQ ID NO: 34) |
| Euprosterna elaeasa virus 2A | CGACGATTGCCGGAGTCCGCCCAGCTCCCCC AAGGGGCGGGGCGCGGAAGTCTGGTAACAT GTGGCGACGTGGAGGAGAATCCAGGGCCC (SEQ ID NO: 15) | RRLPESAQLPQGA GRGSLVTCGDVEE NPGP (SEQ ID NO: 35) |
| Providence virus 2A$_1$ | TTGGAGATGAAGGAGTCTAATAGTGGTTACGT AGTCGGTGACCGGGGGTCTCTTCTCACTTGT GGGGACGTTGAATCCAACCCTGGACCC (SEQ ID NO: 16) | LEMKESNSGYVVG DRGSLLTCGDVES NPGP (SEQ ID NO: 36) |
| Providence virus 2A$_3$ | ACGCTTATGGGGAACATCATGACACTTGCAGG GTCAGGTGGTCGGGGAAGCTTGCTGACCGCA GGCGATGTTGAAAAGAACCCTGGGCCC (SEQ ID NO: 17) | TLMGNIMTLAGSGG RGSLLTAGDVEKNP GP (SEQ ID NO: 37) |
| Bombyx mor cypovirus-1 2A | AGAACAGCGTTCGATTTCCAGCAGGACGTTTT TCGCTCTAATTATGACCTACTAAAGTTGTGCG GTGATATCGAGTCTAATCCTGGACCTGTTAC (SEQ ID NO: 18) | RTAFDFQQDVFRS NYDLLKLCGDIESN PGP (SEQ ID NO: 38) |
| Operophtera brumata cypovirus-18 2A | ATCCATGCTAATGATTATCAGATGGCTGTGTTT AAATCAAATTATGATTTGCTGAAGTTATGCGG GGACGTGGAATCAAATCCTGGCCCT (SEQ ID NO: 19) | IHANDYQMAVFKSN YDLLKLCGDVESNP GP (SEQ ID NO: 39) |
| new adult diarrhea virus 2A | TTCTTCGATTCGGTTTGGGTGTACCACTTGGC AAACAGCTCTTGGGTTCGAGATTTAACTAGAG AATGCATTGAATCTAACCCTGGACCA (SEQ ID NO: 20) | FFDSVWVYHLANS SWVRDLTRECIESN PGP (SEQ ID NO: 40) |

In particular embodiments, a 2A peptide linker including a consensus motif DXEXNPGP (SEQ ID NO: 41), where X can be any amino acid, may be used. Luke (2008) J Gen Virol 89: 1036-1042. In particular embodiments, combinations of two or more 2A peptide linkers of the same or different sequences may be used (Liu et al. (2017) Scientific Reports 7: 2193).

Genetic constructs used within the libraries disclosed herein can also include an internal ribosome entry site (IRES) that allows for translation initiation in a 5'-cap independent manner. In particular embodiments, an IRES can be used to ensure that viral translation is active when host translation is inhibited. Genetic constructs used within the libraries disclosed herein can also include different promoters regulating expression of the reporter gene and the gene encoding a variant protein.

Genetic constructs used within the libraries disclosed herein can also include sequences to facilitate sequencing. In particular embodiments, sequences to facilitate sequencing can include Illumina P5 and P7 sequences and other adapter sequences included in Illumina Adapter Sequences, Document #1000000002694 v06, February 2018 (Illumina, San Diego, CA).

The term vector refers to a nucleic acid molecule capable of transferring or transporting another nucleic acid molecule. The transferred nucleic acid is generally linked to, e.g., inserted into, the vector nucleic acid molecule. A vector may include sequences that direct autonomous replication in a cell, or may include sequences that permit integration into host cell DNA. Useful vectors include, for example, plasmids (e.g., DNA plasmids or RNA plasmids), transposons, cosmids, bacterial artificial chromosomes, and viral vectors. In particular embodiments, a plasmid is a small, circular nucleic acid molecule that allows expression of a gene carried by the plasmid but that does not integrate into the genome of the cell into which the plasmid is transfected.

Viral vector is widely used to refer to a nucleic acid molecule that includes virus-derived nucleic acid elements that facilitate transfer and expression of non-native nucleic acid molecules within a cell. The term adeno-associated viral vector refers to a viral vector or plasmid containing structural and functional genetic elements, or portions thereof, that are primarily derived from AAV. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, that are primarily derived from a lentivirus, and so on. The term "hybrid vector" refers to a vector including structural and/or functional genetic elements from more than one virus type.

Genetic constructs used within the libraries disclosed herein can use any retroviral vector backbone, as long as the retroviral vector is able to be integrated into the genome of a cell and be non-self-inactivating. A retroviral vector can integrate into a host cell genome with the help of the viral integrase and the long terminal repeats (LTRs) present at the ends of the retroviral vector. Enzymes of the host are used for replication of the integrated retroviral vector. The retroviral vectors can be derived from members of the Retroviridae family. The Retroviridae family includes three groups: the spumaviruses (or foamy viruses) such as the human foamy virus (HFV); the lentiviruses, as well as visna virus of sheep; and the oncoviruses. The term "lentivirus" includes a genus of viruses containing reverse transcriptase. The lentiviruses include the "immunodeficiency viruses" which include human immunodeficiency virus (HIV) type 1 and type 2 (HIV-1 and HIV-2) and simian immunodeficiency virus (SIV). The oncoviruses have historically been further subdivided into groups A, B, C and D on the basis of particle morphology, as seen under the electron microscope during viral maturation. The C-type viruses are the most commonly studied and include many of the avian and murine leukemia viruses (MLV). Bovine leukemia virus (BLV), and the human T-cell leukemia viruses types I and II (HTLV-I/II) are similarly classified as C-type particles.

Retroviruses have been classified in various ways but the nomenclature has been standardized in the last decade (see ICTVdB—The Universal Virus Database, v 4 on the World Wide Web (www) at ncbi.nlm.nih.gov/ICTVdb/ICTVdB/ and the text book "Retroviruses" Eds Coffin, Hughs and Varmus, Cold Spring Harbor Press 1997).

Retroviruses are defined by the way in which they replicate their genetic material. During replication the RNA is converted into DNA. Following infection of the cell a double-stranded molecule of DNA is generated from the two molecules of RNA which are carried in the viral particle by the molecular process known as reverse transcription. The DNA form becomes covalently integrated in the host cell genome as a provirus, from which viral RNAs are expressed with the aid of cellular and/or viral factors. The expressed viral RNAs are packaged into particles and released as infectious virion.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRs. A duplication of cellular sequences is seen at the ends of both LTRs, reminiscent of the integration pattern of transposable genetic elements. Retroviruses can integrate their DNAs at many sites in host DNA, but different retroviruses have different integration site preferences.

Transcription, RNA splicing and translation of the integrated viral DNA is mediated by host cell proteins. Variously spliced transcripts are generated. In the case of the human retroviruses HIV-1/2 and HTLV-I/II, viral proteins are also used to regulate gene expression. The interplay between cellular and viral factors is a factor in the control of virus latency and the temporal sequence in which viral genes are expressed.

Key to the current disclosure is that, whatever retroviral vector system is utilized, the construct should include a long terminal repeat (LTR) with a functional U3. In particular embodiments, a functional U3 can be obtained by repairing a deleted or disrupted 3' LTR from a self-inactivating (SIN) lentiviral system that disrupts genome packaging (Miyoshi et al. (1998) Journal of Virology 72(10): 8150-8157). The repair can include cloning the 5' LTR into the correct location at the 3'. These SIN retroviral systems include pHAGE, pHAGE2, and other pHAGE systems (described in protocols by the Kotton Lab at the Center for Regenerative Medicine, Boston University), and pHIV and other variants such as pHIV-7 (Miyoshi et al. (1998), supra). In particular embodiments, a functional U3 can be obtained from LTRs of other retroviruses, such as murine leukemia virus (MLV). Moloney MLV (MoMLV) retroviral systems include replication competent (functional) LTRs (Dalba et al. (2007) Molecular Therapy 15(3): 457-466). In particular embodiments, a functional U3 can be obtained from an LTR of a retrovirus belonging to the Retroviridae family. In particular embodiments, a functional U3 is a full U3 sequence. In particular embodiments, a functional U3 is a U3 from a retrovirus that has not been modified. In particular embodiments, a functional U3 allows transcription of the integrated variant gene, selectable marker, and barcode, and subsequent packaging into retroviral particles. In particular embodiments, inclusion of a functional U3 means that integrated variant gene, selectable marker, and barcode are transcribed and packaged into retroviral particles when cells storing the library are additionally transfected with Gag, Pol, Tat, and Rev. An exemplary U3 sequence is SEQ ID NO: 42. Examples of Gag, Pol, Tat, and Rev sequences (SEQ ID NOs: 43-54) are shown in FIG. 15. This feature is described in more detail in relation to FIG. 5.

Figure 5:
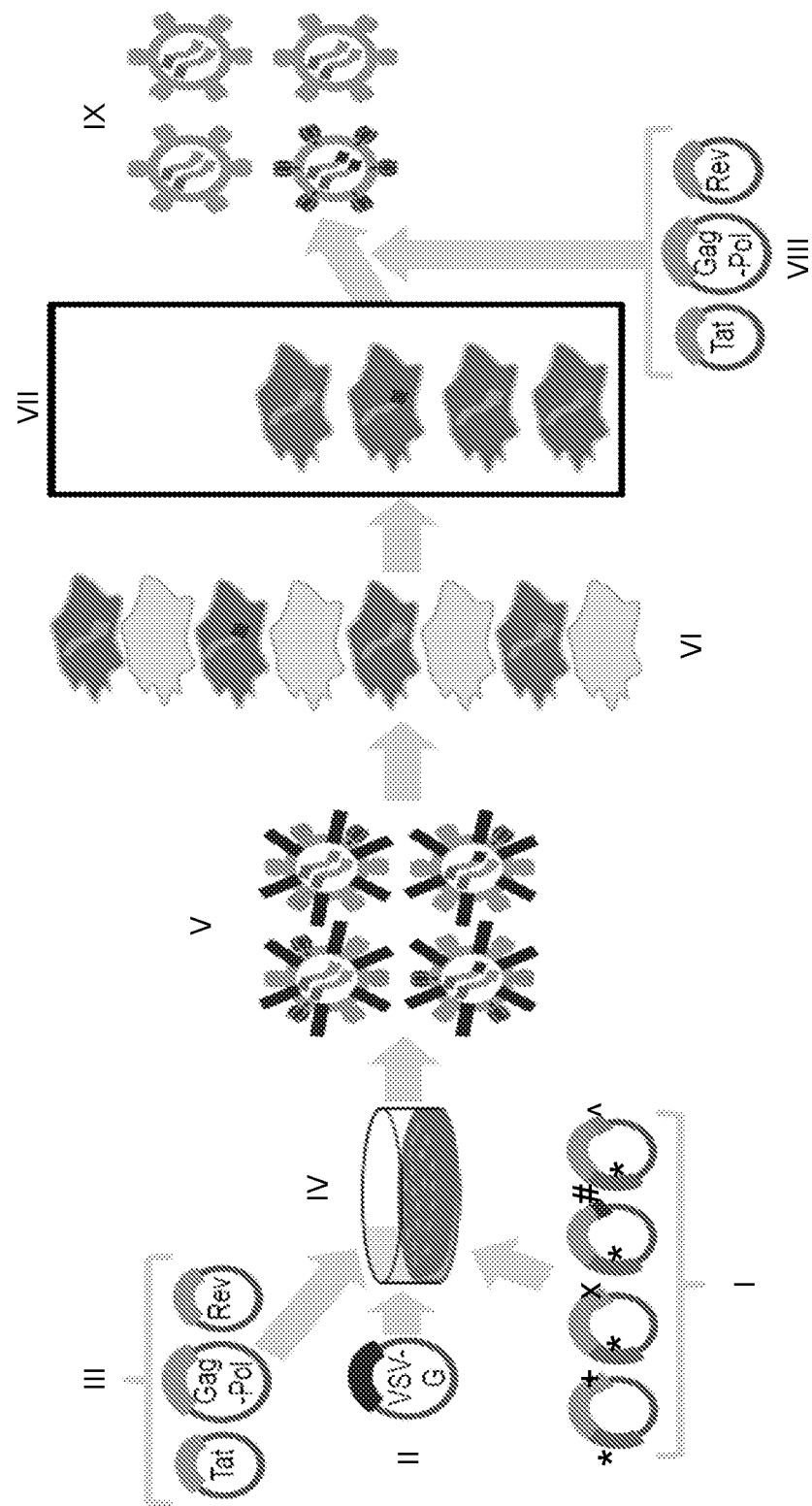
FIG. 5. Process to create cells that store a library of viral entry protein variants (outlined in black box, VII). The viral vectors of I are the constructs depicted in FIG. 4A, lentiviral vectors including full functional U3, CMV promoter, GFP, 2A linker, and barcoded entry protein. The reporter (e.g., GFP) is marked with a *, and +, x, #, and ˆ indicate unique barcodes in I. Transfection of 293T cells (IV) with I, VSV-G entry protein for the next round of infection (II), and plasmids encoding non-surface proteins for lentivirus production (III) produces VSV-G pseudotyped lentiviral vectors carrying entry protein library with scrambled barcodes and no genotype-phenotype link (V). Low MOI infection of 293T cells leads to integration of at most a single copy of the vector encoding one entry protein variant (VI). $5 \times 10^5$ unique GFP+ cells are sorted, and these cells store the library (VII). Transfection of cells in the library (VII) with helper plasmids (VIII) creates lentiviral virion library with entry proteins linked to barcodes (IX).

FIG. 5 depicts a process used to create the cells that store the library (outlined in black box). The viral vectors at the bottom left (I) are the constructs described in relation to FIG. 4A. The reporter (e.g., GFP) is marked with a *, and +, x, #, and A indicate unique barcodes in I. Within the teachings of the current disclosure, a viral library cannot be created simply by transfecting cells with the viral vectors because transfected cells take up many viral vectors and recombination would scramble the barcode-variant link. Therefore, the libraries can be stored in cells by integrating them at one entry protein variant per cell on non-self-inactivating lentiviral vectors as shown in FIG. 5 (black box, VII). In particular embodiments, each cell has at most a single copy of the non-self-inactivating lentiviral vector encoding one entry protein variant.

To achieve the library depicted within the black box (VII) of FIG. 5, in particular embodiments, 293T cells can be transfected with viral vectors including the barcoded codon-mutant entry protein library along with plasmids to express proteins for virion formation (Tat, Gag, Pol, Rev) and the amphotropic entry protein VSV-G (vesicular stomatitis virus glycoprotein). The resulting virions will be heterozygous and lack a genotype-phenotype link (entry proteins on virion surface may not match genes in virion), but they can infect cells using VSV-G. In particular embodiments, alternative envelope glycoproteins (GPs) that can be used instead of VSV-G include MLV GP and feline endogenous retrovirus (RD114) GP, gibbon ape leukemia virus (GALV) Env, and variants of these. Cronin et al. (2005) Curr Gene Ther. 5(4): 387-398. In particular embodiments, GPs that can be used are derived from a family including Rhabdoviridae, Arenaviridae, Togaviridae, Filoviridae, Retroviridae, Coronaviridae, Paramyxoviridae, Flaviviridae, Orthomyxoviridae, and Baculoviridae. In particular embodiments, GPs that can be used are derived from a genus including Vesiculovirus, Lyssavirus, Arenavirus, Alphavirus, Filovirus, Alpharetrovirus, Betaretrovirus, Gammaretrovirus, Deltaretrovirus, Spumavirus, Lentivirus, Coronavirus, Respirovirus, Hepacivirus, Influenzavirus A, and nucleopolyhedrovirus. In particular embodiments, GPs that can be used are derived from a species including vesicular stomatitis virus (Indiana virus), Chandipura virus, rabies virus, Mokola virus, Lymphocytic choriomeningitis virus (LCMV), Ross River virus (RRV), Sindbis virus, Semliki Forest virus (SFV), Venezuelan equine encephalitis virus, Ebola virus Reston, Ebola virus Zaire, Marburg virus, Lassa virus, avian leukosis virus (ALV), Jaagsiekte sheep retrovirus (JSRV), MLV, GALV, RD114, human T-lymphotropic virus 1 (HTLV-1), human foamy virus, Maedi-visna virus (MVV), severe acute respiratory syndrome coronavirus (SARS-CoV), Sendai virus, Respiratory syncytial virus (RSV), human parainfluenza virus type 3, hepatitis C virus (HCV), influenza virus, fowl plague virus (FPV), and *Autographa californica* multiple nucleopolyhedro virus (AcMNPV).

In particular embodiments, a deep mutational scanning library includes viral protein variants of an entry protein, and the cells storing the library are additionally transfected with plasmids to express one or more of Gag Pol, Tat, and/or Rev for virion production. In particular embodiments, a deep mutational scanning library includes viral protein variants of an entry protein, and the cells storing the library are additionally transfected with plasmids to express one or more of Gag Pol, Tat, Rev, and/or a functional unrelated entry protein for virion production. In particular embodiments, a functional unrelated entry protein can include a viral entry protein that causes virions to be infectious but that is derived from a virus distinct from the virus on which the library of protein variants is based. In particular embodiments, a functional unrelated entry protein is unaffected by a therapeutic compound and can serve as an absolute standard in an antibody neutralization assay. In particular embodiments, a deep mutational scanning library includes viral protein variants of a Gag Pol polyprotein, and the cells storing the library are additionally transfected with plasmids to express one or more of an entry protein, Tat, and/or Rev for virion production. In particular embodiments, a deep mutational scanning library includes viral protein variants of a Tat protein, and the cells storing the library are additionally transfected with plasmids to express one or more of an entry protein, Gag Pol polyprotein, and/or Rev for virion production. In particular embodiments, a deep mutational scanning library includes viral protein variants of a Rev protein, and the cells storing the library are additionally transfected with plasmids to express one or more of an entry protein, Gag Pol polyprotein, and/or Tat for virion production.

Cells can be infected with an amount of virions so that at least a percentage of storage cells have at most one copy of the retroviral vector including a single viral protein variant, a barcode, and a functional U3. In particular embodiments, cells can be infected with an amount of virions so that each storage cell of 70% to 100% of storage cells have at most one copy of the retroviral vector including a single viral protein variant, a barcode, and a functional U3. In particular embodiments, cells can be infected with an amount of virions so that each storage cell of 80% to 100% of storage cells have at most one copy of the retroviral vector including a single viral protein variant, a barcode, and a functional U3. In particular embodiments, cells can be infected with an amount of virions so that each storage cell of 90% to 100% of storage cells have at most one copy of the retroviral vector including a single viral protein variant, a barcode, and a functional U3. In particular embodiments, cells can be infected with an amount of virions so that each storage cell of at least 70%, at least 75%, at least 80%, at least 85%, at least 90%, at least 91%, at least 92%, at least 93%, at least 94%, at least 95%, at least 96%, at least 97%, at least 98%, or at least 99% of storage cells have at most one copy of the retroviral vector including a single viral protein variant, a barcode, and a functional U3. In particular embodiments, an amount of virions can include nanogram (ng) amounts of virions, infectious units (IU) of virions, and/or low MOI. In particular embodiments, 293T cells can be infected with VSV-G virions at low MOI, and infected cells can be sorted using the reporter. These cells (black box in FIG. 5) store the library. Because the sum of Poisson random variables is a Poisson variable, recombination of the viral genome will not alter the mutation distribution. In particular embodiments, a low MOI can include an MOI of 0.01 to 0.5. In particular embodiments, a low MOI can include an MOI of 0.05 to 0.3. In particular embodiments, a low MOI can include an MOI of 0.1 to 0.2. In particular embodiments, a low MOI can include an MOI of 0.01. In particular embodiments, a low MOI can include an MOI between 0.001 and 0.01. In particular embodiments, a low MOI can include an MOI of 0.001, 0.002, 0.003, 0.004, 0.005, 0.006, 0.007, 0.008, 0.009, and/or 0.01. In particular embodiments, a low MOI can include an MOI of 0.005. In particular embodiments, a low MOI can include an MOI of 0.0075.

Cells of the disclosure used for storing a deep mutational scanning library are diploid, meaning that they have two sets of chromosomes, one set from each parent cell. Diploid cells have the same loci on each of their two sets of homologous chromosomes except that the sequences at these loci may differ or may be the same between the two chromosomes in a matching pair. When cells of the disclosure are infected with an amount of virions at low MOI, each resulting storage cell contains a single barcoded variant nucleotide sequence in a homozygous state, meaning that the locus on a chromosome at which the viral vector is integrated in the cell's diploid genome will have the same barcoded variant nucleotide sequence on the two sets of homologous chromosomes. In particular embodiments, in the context of non-replicative virions produced from transfection of storage cells containing the library of protein variants with helper plasmids, both copies of the pseudodiploid lentiviral genome are identical in each virion (see FIG. 7).

Different cell lines can be used to generate the initial retroviral virions that are used to generate the library and to store the mutant library in. In particular embodiments, a cell line suitable for these purposes can be transfected (e.g., by chemical methods or by electroporation). In particular embodiments, a cell line suitable for these purposes does not have many inherent immune factors. In particular embodiments, a cell line suitable for these purposes is robust to viral proteins being expressed. In particular embodiments, cell lines can include: HEK293T (293T) and related cell lines (e.g., HEK293T/17 aka HEK293T clone 17, HEK293F, HEK293S, HEK293SGH, EK293FTM, HEK293SGGD, GP2-293); HeLa and related cell lines (e.g., HeLa S3, HeLa B, HeLa T4); Chinese Hamster Ovary (COS) and related cell lines (e.g., COS-1, COS-6, COS-M6A, COS-7); A549; MDCK; HepG2; C2C12; THP-1; HUDEP-2; C8161; CCRF-CEM; MOLT; mIMCD-3; NHDF; Huh1; Huh4; Huh7; HUVEC; HASMC; HEKn; HEKa; MiaPaCell; Panc1; PC-3; TF1; CTLL-2; C1R; Rat6; CV1; RPTE; A10; T24; J82; A375; ARH-77; Calu1; SW480; SW620; SKOV3; SK-UT; CaCo2; P388D1; SEM-K2; WEHI-231; HB56; TIB55; Jurkat; J45.01; LRMB; Bcl-1; BC-3; IC21; DLD2; Raw264.7; NRK; NRK-52E; MRCS; MEF; BS-C-1; monkey kidney epithelial; BALB/3T3 mouse embryo fibroblast; 3T3 Swiss; 3T3-L1; 132-d5 human fetal fibroblasts; 10.1 mouse fibroblasts; 3T3; 721; 9L; A2780; A2780ADR; A2780cis; A172; A20; A253; A431; A-549; ALC; B16; B35; BCP-1; BEAS-2B; bEnd.3; BHK-21; BR 293; BxPC3; C3H-10T1/2; C6/36; Cal-27; CHO; CHO-7; CHO-IR; CHO-K1; CHO-K2; CHO-T; CHO Dhfr −/−; COR-L23; COR-L23/CPR; COR-L23/5010; COR-L23/R23; COV-434; CML T1; CMT; CT26; D17; DH82; DU145; DuCaP; EL4; EM2; EM3; EMT6/AR1; EMT6/AR10.0; FM3; H1299; H69; HB54; HB55; HCA2; Hepa1c1c7; HL-60; HMEC; HT-29; JY; K562; Ku812; KCL22; KG1; KYO1; LNCap; Ma-Mel 1-48; MC-38; MCF-7; MCF-10A; MDA-MB-231; MDA-MB-468; MDA-MB-435; MDCK II; MOR/0.2R; MONO-MAC 6; MTD-1A; MyEnd; NCI-H69/CPR; NCI-H69/LX10; NCI-H69/LX20; NCI-H69/LX4; NIH-3T3; NALM-1; NW-145; OPCN/OPCT cell lines; Peer; PNT-1A/PNT2; RenCa; RIN-5F; RMA/RMAS; Saos-2; Sf-9; SkBr3; T2; T-47D; T84; THP1; U373; U87; U937; VCaP; Vero; WM39; WT-49; X63; YAC-1; and YAR.

A substantial portion of entry protein variants will be non-functional when expressed. Accordingly, in particular embodiments, the virion library can be produced as in the last step of FIG. 5 but it can also be transfected with VSV-G so all virions are infectious regardless of whether they produce a non-functional entry protein. As described above, alternative glycoproteins to VSV-G can be used. In particular embodiments, a functional viral entry protein that can be used includes a viral protein that causes virions to be infectious but that is derived from a virus distinct from the virus on which the library of protein variants is based, so that non-functional protein variants in a cell-stored deep mutation scanning library can be captured and identified.

The approach depicted in FIG. 5 also requires that the entry protein not interfere with production of VSV-G-carrying virions or be toxic to transduced cells. If necessary, the backbone construct (e.g., those depicted in FIGS. 4A-4F) can be amended to use an inducible promoter or to fuse a switchable degradation domain [Iwamoto, et al. (2010) Chemistry & Biology 17: 981-988] to the entry protein.

Examples of inducible promoter systems that can be used in the systems and methods of the present disclosure include: lac operon [Brown et al. (1987) Cell 49: 603-612; Hu and Davidson (1987) Cell 48: 555-566]; tetracycline (Tet) (or derivative doxycycline)-inducible systems (Tet-On and Tet-Off) [Gossen et al. (1995) Science 268: 1766-1769; Baron et al. (1997) Nucleic Acids Res 25: 2723-2739; Blau and Rossi (1999) Proc Natl Acad Sci USA 96: 797-799]; mifepristone-inducible systems (GeneSwitch) [Burcin et al. (1999) Proc. Natl. Acad. Sci. USA 96(2): 355-360; Wang et al. (1994) Proc. Natl. Acad. Sci. USA 91(17): 8180-8184]; ecdysone-regulated system [Galimi et al. (2005) Blood 105(6): 2400-2402]; streptogramin-adjustable expression system derived from *Streptomyces coelicolor* [Mitta et al. (2004) Nucleic Acids Res 32(12): e106]; gaseous acetaldehyde-inducible expression system derived from *Aspergillus nidulans* [Hartenbach S & Fussenegger M (2005) J Biotechnol 120(1): 83-98]; and cumate-inducible systems [U.S. Pat. No. 7,745,592; Mullick et al. (2006) BMC Biotechnology 6:43].

Examples of switchable degradation domains that can be used in the systems and methods of the present disclosure include: low-temperature-controlled N-terminal degradation signal (lt-degron) [Faden et al. (2016) Nat Comm 7:12202]; Blue-Light Inducible Degradation (B-LID) domain [Bonger et al. (2014) ACS Chem Biol 9(1): 111-115]; photosensitive degron (psd) module combining the light-reactive LOV2 domain of *Arabidopsis thaliana* phot1 with the murine ornithine decarboxylase-like degradation sequence cODC1 [Renicke et al. (2013) Chem & Biol 20(4): 619-626]; ligand regulated variant FK506 binding domain and other variants from FKBP12 [Egeler et al. (2011) J Biol Chem 286: 31328-31336; Bersuker et al. (2016) J Cell Biol 213(2): 229-241]; and ornithine decarboxylase (ODC)/antizyme (AZ) [Matsuzawa et al. (2005) PNAS 102(42): 14982-14987].

In particular embodiments, keeping non-functional viral entry protein variants is essential for functional mapping. However, for mapping that is only relevant to functional viral entry protein variants (e.g., antibody selections), efficiency can be improved by removing cells that do not have integrated viral entry protein variants. In particular embodiments, this can be achieved by sorting for cells that express a reporter or selectable marker due to integration of a retroviral vector backbone including the reporter or selectable marker, a gene encoding a protein variant, and a barcode.

After creating library storing cells as outlined in FIG. 5, each gene encoding an entry protein variant can be associated with its barcode. In particular embodiments, this can be conducted using circular consensus PacBio sequencing as described in Travers, et al. (2010) Nucleic Acids Research 38: e159-e159; and Laird Smith, et al. (2016) Virus Evolution 2: vew018. In particular embodiments, a high throughput sequencing method that can sequence long reads with high accuracy can be used to associate each entry protein variant with its barcode. In particular embodiments, long reads can include greater than 100 bp, greater than 200 bp, greater than 300 bp, greater than 400 bp, greater than 500 bp, greater than 600 bp, greater than 700 bp, greater than 800 bp, greater than 900 bp, greater than 1000 bp, greater than 2000 bp, greater than 3000 bp, greater than 4000 bp, greater than 5000 bp, greater than 6000 bp, greater than 7000 bp, greater than 8000 bp, greater than 9000 bp, greater than 10,000 bp, or more. In particular embodiments, accuracy of a sequencing method is related to the sequencing method's error rate. A sequencing error rate can be expressed as a sequencing quality score of a given base, Q, defined by the following equation: $Q=-10 \log_{10}(e)$, where e is the estimated probability of the base call being wrong. Higher Q scores indicate a smaller probability of error. In particular embodiments, a Q score of 10 represents an error rate of 1 in 10 bases, and the inferred base call accuracy is 90%. In particular embodiments, a Q score of 20 represents an error rate of 1 in 100 bases, and the inferred base call accuracy is 99%. In particular embodiments, a Q score of 30 represents an error rate of 1 in 1000 bases, and the inferred base call accuracy is 99.9%. In particular embodiments, high accuracy includes having fewer systematic errors such as errors in base calling or read mapping/alignment and/or errors that are independent of the sequencing context. For example, a high throughput sequencing method that has errors independent of sequencing context would have the same error rate regardless if the sequence was AAAAAAAA (SEQ ID NO: 55) versus AAAAACAG (SEQ ID NO: 56). (DePristo et al. (2011) Nat Genet 43(5): 491-498; Roberts et al. (2013) Genome Biology 14:405. In particular embodiments, high accuracy includes 99.99% accuracy.

In particular embodiments, each gene encoding a viral entry protein variant can be associated with its barcode by subassembly as described in U.S. Pat. No. 8,383,345. In particular embodiments, if the gene encoding a viral entry protein variant is small, each gene encoding a viral entry protein variant can be associated with its barcode by a barcoded subamplicon approach as described above and in Doud and Bloom (2016) Viruses 8: 155.

Figure 6:
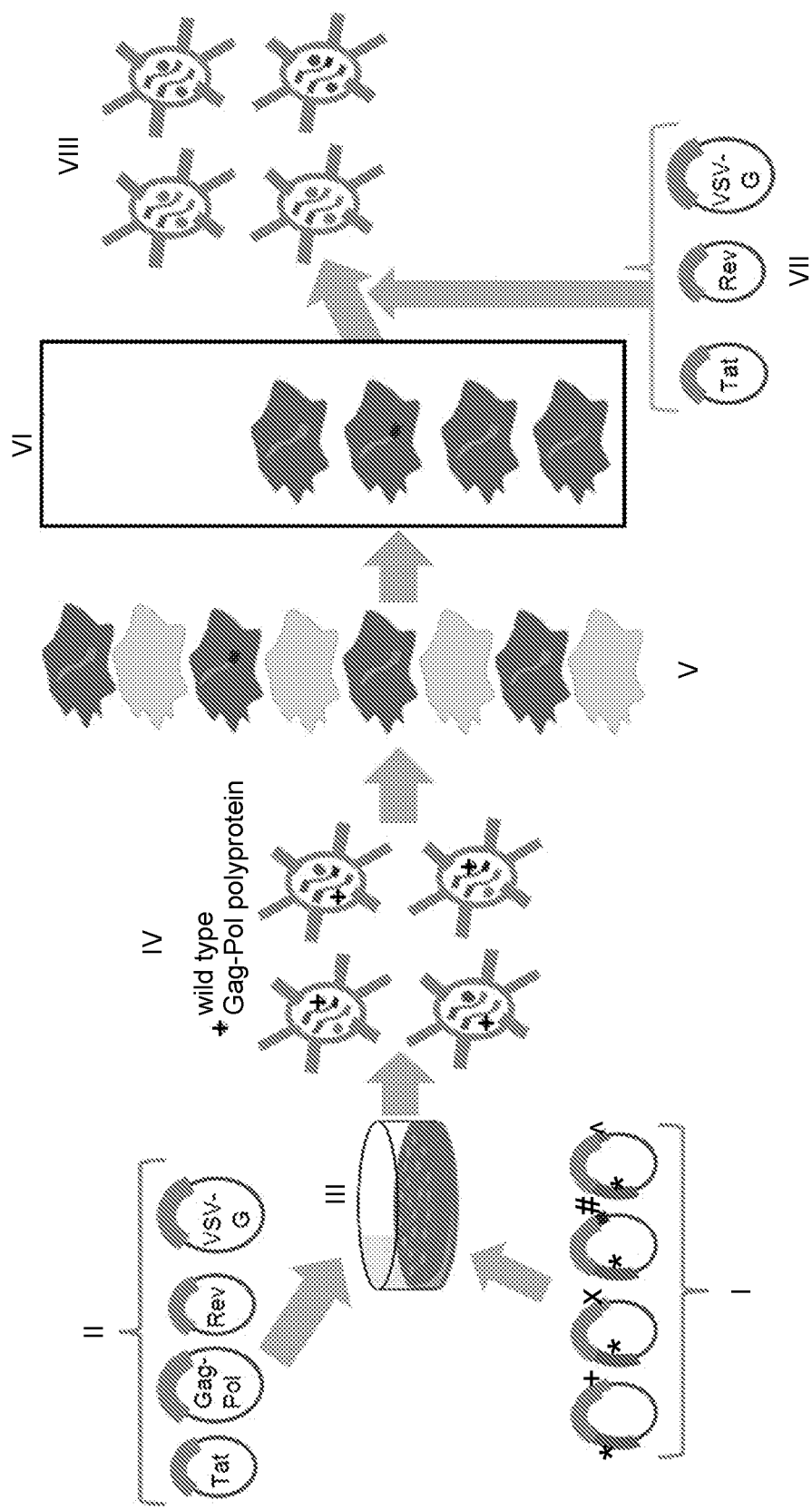
FIG. 6. Schematic to generate a library of variants for a non-viral entry protein of a virus, such as the Gag-Pol polyprotein. The resulting genotype-phenotype linked virus can be subjected to different drugs that inhibit various steps that rely on protein products of the Gag-Pol protein (virion assembly, reverse transcription, protease cleavage, integration). Drug selection could be administered while producing the final library or during another round of entry into cells, depending on the target of the drug. Transfection of 293T cells (III) with: lentiviral backbone plasmids including full functional U3, CMV promoter, GFP, 2A linker, and barcoded mutant Gag-Pol genes (I); and plasmids encoding all proteins for lentivirus production, including a wild type Gag-Pol to ensure reverse transcription (II), produces VSV-G pseudotyped lentiviral vectors carrying Gag-Pol protein library with scrambled barcodes and no genotype-phenotype link (IV). Mutant non-functional Gag-pol variants can be rescued by the functional Gag-Pol wild type genes also transfected into cells. Low MOI infection of 293T cells leads to integration of at most a single copy of the vector encoding one Gag-Pol protein variant (V). $5 \times 10^5$ unique GFP+ cells are sorted, and these cells store the library (VI). Transfection of cells in the library (VI) with helper plasmids (VII) creates a lentiviral virion library with Gag-Pol linked to barcodes (VIII). The reporter (e.g., GFP) is marked with a *, and +, x, #, and ^ indicate unique barcodes in I.

One of ordinary skill in the art will appreciate that the systems and methods described above to generate a deep mutational scanning library can be applied to any protein. In particular embodiments, generating a deep mutational scanning library of a given non-viral protein can follow the steps depicted in FIG. 5 and end with a cell-stored library as indicated in the black box (VII) of FIG. 5. The non-viral protein variants of the deep mutational scanning library can then be assessed by assays particular to the function of the given non-viral protein. Additionally, one of ordinary skill in the art will appreciate that the systems and methods described above to generate a deep mutational scanning library can be applied to any viral protein. FIG. 6 shows a schematic to generate a library of variants for a non-viral entry protein of a virus, such as the Gag-Pol polyprotein. The resulting genotype-phenotype linked virus can be subjected to different drugs that inhibit various steps that rely on protein products of the Gag-Pol protein (virion assembly, reverse transcription, protease cleavage, integration). Drug selection can be administered while producing the final library or during another round of entry into cells, depending on the target of the drug. In particular embodiments, a deep mutational scanning library of the present disclosure can include variants of a given viral protein from many different strains or isolates of a given virus.

In particular embodiments, integrated viral cDNA can be harvested by mini-prep. In particular embodiments, non-integrated viral cDNA can be harvested by mini-prep [Haddox, et al. (2016) PLoS Pathogens 12: e1006114; Haddox et al. (2018) eLife 7:e34420; Dingens et al. (2017) Cell Host & Microbe 21: 777-787]. The reason for harvesting non-integrated rather than integrated viral cDNA in particular embodiments is that the former is 20-fold more abundant, and is isolated separately from genomic DNA, simplifying subsequent steps. In particular embodiments, strand switching can be avoided by amplifying barcode-linked genes via emulsion PCR as described in Schutze, et al. (2011) Analytical Biochemistry 410: 155-157. In particular embodiments, these embodiments can further include ligating SMRTbell adaptors, sequencing on a PacBio Sequel, and building circular consensus sequences using ccs (v2).

Adopting the described approaches, an unmutated 2.5 kb gene was sequenced and $10^5$ circular consensus reads at 99.99% accuracy on one SMRT cell of a Sequel was obtained. In particular embodiments, because the amplicons that will be sequenced are subject to reverse-transcription and PCR errors, it is not useful to require >99.99% accuracy. Instead, one can oversequence 3-fold and only retain barcodes for which multiple circular consensus sequences agree (which will be the vast majority). Once a barcode lookup table is created, in all subsequent experiments it is only necessary to sequence (e.g., Illumina sequence) the barcode. In particular embodiments, a high throughput sequencing method that can sequence reads of 10 bp, 20 bp, 30 bp, 40 bp, 50 bp, 60 bp, 70 bp, 80 bp, 90 bp, 100 bp, or more with a low error rate (e.g., 1 error per 100 bases, 1 error per 200 bases) can be used to sequence barcodes. This is tremendously useful because there are so many different types of downstream selection experiments that are valuable.

The cells storing the barcoded library can be expanded and stored to propagate the library. In particular embodiments, the cells should be passaged at $>10^6$ to maintain diversity. If needed, these titers can be increased by concentration [Coleman, et al. (2003) Physiological Genomics 12: 221-228; Kutner, et al. (2009) Nature Protocols 4: 495-505]. Cells will produce different viral yields depending on the site of retroviral integration. However, the assays are on virions not cells, so the VSV-G control can be used to correct for differences. If unevenness is extreme, the retroviral backbones can be integrated at a defined location for example, as described in Matreyek, et al. (2017) Nucleic Acids Research 45: e102-e102. In particular embodiments, retroviral backbones can be integrated using a gene editing system including zinc finger nucleases, homing endonucleases, Transcription Activator-Like Effector Nucleases (TALENs), megaTALs, and Clustered Regularly Interspaced Short Palindromic Repeats (CRISPR)-CRISPR associated nuclease (Cas) systems. Zinc finger nucleases are described in, for example, US2003/0232410; US2005/0208489; US2005/0026157; US2005/0064474; US2006/0188987; US2006/0063231; US2007/0134796; US2008/015164; US2008/0131962; US2008/015996; WO2007/014275; WO2008/133938; Kim et al. (1996) Proceedings of the National Academy of Sciences of the United States of America 93: 1156-1160; Wolfe et al. (2000) Annual review of biophysics and biomolecular structure 29: 183-212; Bibikova et al. (2003) Science 300, 764; Bibikova et al. (2002) Genetics 161: 1169-1175; Miller et al. (1985) The EMBO journal 4: 1609-1614; and Miller et al. (2007) Nature biotechnology 25: 778-785. Homing endonucleases are described in, for example, Stoddard (2011) Structure 19(1): 7-15; Arnould et al. (2006) Journal of molecular biology 355(3): 443-458; Jurica et al. (1998) Molecular cell 2(4): 469-476; US2011/0256607; WO2007/049095; WO2007/049156; WO2008/102198; WO2014/191527; and WO2014/191525. TALENs are described in, for example, Boch et al. (2009) Science 326: 1509-1512; Moscou, & Bogdanove (2009) Science 326: 1501; Christian et al. (2010) Genetics 186: 757-761; and Miller et al. (2011) Nature biotechnology 29: 143-148. MegaTALs are described in, for example, Boissel et al. (2014) Nucleic Acids Res. 42(4): 2591-601. CRISPR-Cas systems are described in, for example, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, and WO2017/127807.

Figure 7:
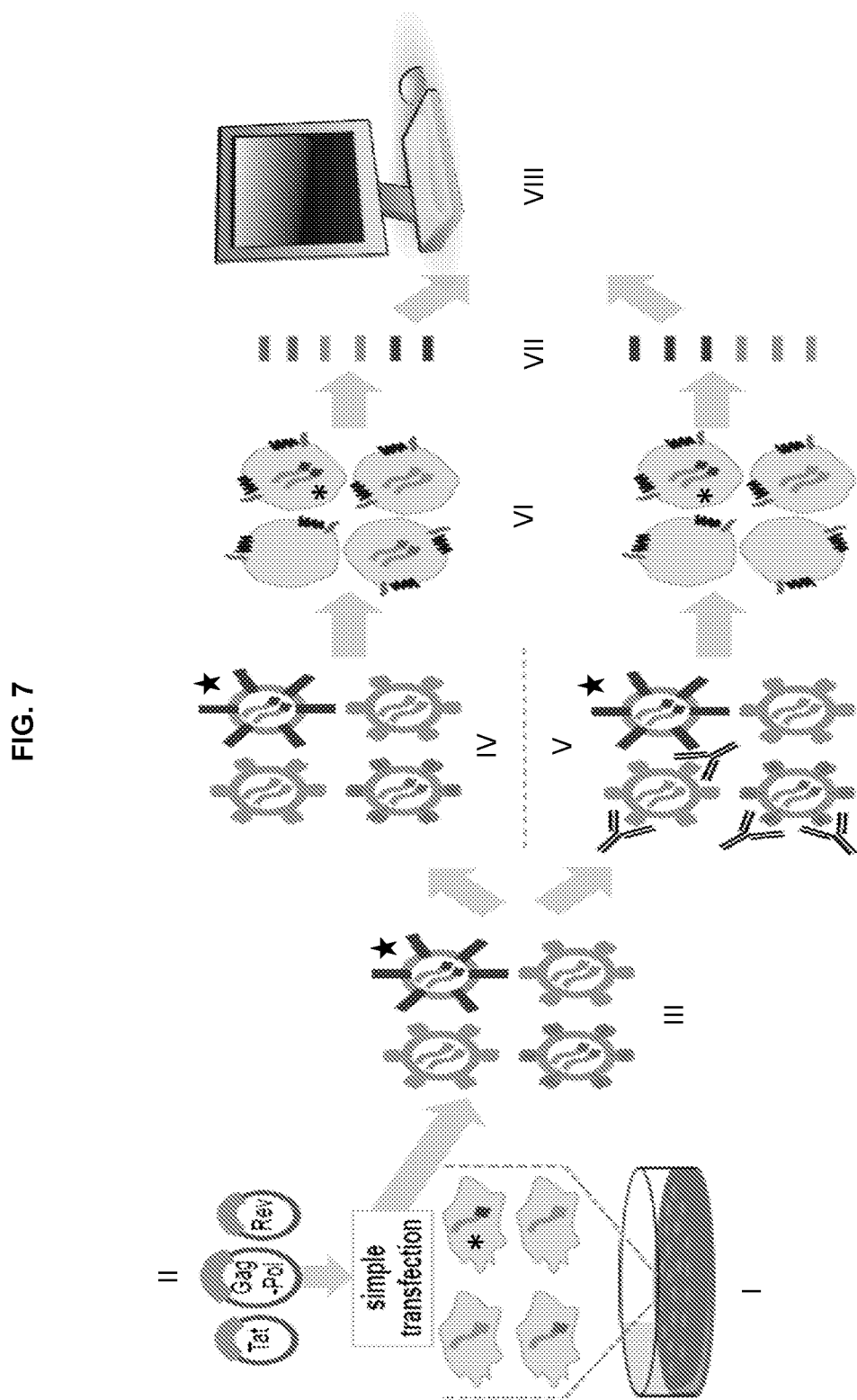
FIG. 7. In the depicted schematic, the libraries are stored in cells (I), each cell having an integrated non-self-inactivating lentiviral vector encoding a single entry protein variant. The lentiviral vectors contain barcoded mutants of entry protein (e.g. Ebola GP) or an unrelated entry protein (e.g., MLV Env) as an absolute standard. Transfection of the cells with plasmids expressing the necessary lentiviral proteins (II) produces non-replicative virions that can be handled at biosafety level (BSL)-2 (III). These virions have a genotype-phenotype link, and there is no recombinational scrambling since both copies of the pseudodiploid lentiviral genome are identical in each virion. The virus libraries are subjected to functional (IV) or immune (antibody/serum) selections (V), target cells are subjected to a short infection with selected virions (VI), and variant frequencies read out by sequencing the barcodes (VII). For immune selections, an absolute standard containing an unrelated entry protein can be used to quantify virus neutralization. Barcode counts are analyzed to determine functional and antigenic effects of mutations (VIII). Entry protein mutants can include non-functional mutants (not selected in either functional selections or in immune selections) and escape mutants (selected in functional selections and in immune selections as they escape antibodies). Counts for antibody selections can be normalized to an absolute standard. *cell containing barcoded entry protein serving as absolute standard. ★Virion expressing barcoded entry protein serving as absolute standard.

FIG. 7 depicts use of the stored library once it has been created. Again, cells with integrated retroviral backbones encoding barcoded mutants (or an unrelated viral entry protein included as a control) can be transfected with viral helper plasmids to induce creation of barcoded and genotype-phenotype linked non-replicative virions that can be handled at BSL-2. As indicated previously, most lentiviral vectors have deletions in U3 in the 3' LTR that make them self-inactivating. This is not desirable within the current disclosure because the first step in FIG. 7 (and the last step in FIGS. 5 and 6) is to produce the virions by transfecting the cells with helper plasmids. With repair of the 3' LTR of the pHAGE2 lentiviral backbone, titers of >5×10$^5$ infectious particles per ml have been achieved.

Following expression of virions from the storage cells, functional studies can be conducted to assess variant viral entry proteins. As indicated, these studies can assess the ability of different viral entry proteins to evade antibody neutralization and/or infect new species. If numerous mutations to a viral entry protein allow antibody evasion or infection of a new host species, the virus may have a higher probability of becoming a health threat. If, however, only few or very specific mutations allow antibody evasion or infection of a new host species, the virus may pose less of a threat.

In particular embodiments, libraries of the present disclosure can be used to assess the efficacy of therapeutic compounds intended to prevent, reduce, or treat the likelihood of a viral infection. Therapeutic compounds can include antiviral compounds or compositions. Examples of antiviral compounds or compositions are disclosed in, for example, U.S. Pat. Nos. 5,994,515, 6,790,611, 8,476,225, 9,259,433, US2009/0214510, US2017/0157190, WO1998/045259, WO2006/138118, WO2008/147427, WO2009/027057, WO2009/151313, WO2012/006596, WO2013/006795, WO2013/072917, WO2013/147584, WO2014/062892, and WO2015/011483; Laursen and Wilson (2013) Antiviral Res 98(3): 476-483; and Pelegrin et al. (2015) Trends in Microbiology 23(10): 653-665. Therapeutic compounds can include small molecules, derivatives of small molecules, antibodies, biologics, proteins, peptides, polynucleotides, polysaccharides, oils, solutions, and plant extracts. In particular embodiments, therapeutic compounds can include entry inhibitors and/or fusion inhibitors. Entry and fusion inhibitors can include enfuvirtide (Fuzeon® (Roche, Basel, Switzerland); a biomimetic peptide that is an HIV fusion inhibitor); AMD070 (investigational; Accession no. DB05501 from Drugbank; small molecule entry inhibitor that targets the CXCR4 receptor to block HIV infection); BMS-488043 (Hanna et al. (2011) Antimicrob Agents Chemother. 55(2): 722-728; oral small molecule HIV-1 attachment inhibitor); fozivudine tidoxil (Fogle et al. (2011) J Vet Intern Med. 25(3): 413-418; thymidine nucleoside analog is a lipid-zidovudine conjugate and member of the family of nucleoside reverse transcriptase inhibitors that decreases viremia in feline immunodeficiency virus (FIV) infected cats); aplaviroc (GSK-873,140; Nakata et al. (2005) J Virol. 79(4): 2087-2096; CCR5 entry inhibitor belonging to a class of 2,5-diketopiperazines developed for the treatment of HIV infection); leronlimab (PRO 140; fully humanized IgG4 monoclonal antibody directed against CCR5, a co-receptor that HIV uses to enter T-cells); PRO 542 (investigational; Accession no. DB05793 from Drugbank; a tetravalent CD4-immunoglobulin fusion protein which neutralizes primary HIV-1 isolates); Peptide T (Pert et al. (1986) Proc Natl Acad Sci USA. 83(23): 9254-9258; a short peptide derived from the HIV envelope protein gp120 which is an HIV entry inhibitor, blocking binding and infection of viral strains which use the CCR5 receptor to infect cells); vicriviroc (SCH-D; $C_{28}H_{38}F_3N_5O_2$; piperazine-based CCR5 receptor antagonist with activity against HIV); ibalizumab (TNX-355; Jacobson et al. (2009) Antimicrob Agents Chemother. 53(2): 450-457; a humanized monoclonal antibody that binds CD4); and maraviroc (Selzentry® (Pfizer, New York, NY); an entry inhibitor that acts as a negative allosteric modulator of the CCR5 receptor). Other examples of viral fusion inhibitor compounds include, for example, highly sulfated polysaccharides from fucoidan or algae; calcium spirulan, nostoflan, or extract of Scoparia dulcis, or antiviral diterpene components contained therein, such as scoparic acid A, scoparic acid B, scoparic acid C, scopodiol, scopadulin, scopadulcic acid A (SDA), scopadulcic acid B (SDB), and/or scopadulcic acid C (SDC). In particular embodiments, anti-viral antibodies can include PRO 140; PRO 542; TNX-355 (ibalizumab); b12 (Burton et al. (1994) Science. 266: 1024-1027; broadly neutralizing human monoclonal IgG1 anti-gp120 antibody); polyclonal caprine antibody PEHRG214 (Verity et al. (2006) AIDS. 20(4): 505-515; antibody raised against purified HIV-associated proteins); PGT121 (Julien et al. (2013) PLoS Pathog 9(5): e1003342; broadly neutralizing antibody); 3BNC117 (Scheid et al. (2016) Nature. 535: 556-560); broadly neutralizing antibody against the CD4 binding site of HIV-1 Env); anti-RSV G protein monoclonal antibody clone 131-2G (Boyoglu-Barnum et al. (2014) J Virol. 88(18): 10569-10583); anti-CXCR4 monoclonal antibody clone 12G5 (McKnight et al. (1997) J Virol. 71(2): 1692-1696); MAB8582 (Anderson et al. (1986) Journal of Clinical Microbiology. 23(3): 475-480; anti-RSV F protein monoclonal antibody clone 102-10B); MAB8581(Anderson et al. (1986) Journal of Clinical Microbiology. 23(3): 475-480; anti-RSV F protein monoclonal antibody clone 92-11C); MCA490 (available from Bio-Rad, Hercules, CA; anti-RSV F protein monoclonal antibody clone RSV3216 (B016)); anti-RSV F antibodies disclosed in U.S. Pat. No. 9,139,642 (104E5, 38F10, 14G3, 90D3, 56E11, 69F6); anti-Ebola virus glycoprotein (GP) monoclonal antibodies c13C6, c2G4, c4G7, and c1H3 (Tran et al. (2016) J. Virol. 90(17): 7618-7627; Murin et al. (2014) Proc Natl Acad Sci USA. 111(48): 17182-17187); LCA60 (Corti et al. (2015) PNAS. 112(33): 10473-10478; MERS-CoV-neutralizing antibody); human anti-MERS-CoV Spike protein neutralizing antibodies REGN3051 and REGN3048 (Pascal et al. (2015) PNAS. 112(28): 8738-8743); human anti-Lassa virus glycoprotein monoclonal antibodies 37.2D, 8.9F, 19.7E, 37.7H, and 12.1F (Robinson et al. (2016) Nat Commun. 7: 11544); or Hendra virus neutralizing human monoclonal antibody m102.4 (Bossart et al. (2011) Sci Transl Med. 3(105): 105ra103).

In particular embodiments, therapeutic compounds can include viral sequence integration inhibitors, proviral transcription inhibitors, protease inhibitors, and inhibitors that inhibit binding of a viral genome to one or more nucleoproteins. In particular embodiments, therapeutic compounds are compounds that are directly or indirectly effective in specifically interfering with at least one viral action including virus penetration of eukaryotic cells, virus replication in eukaryotic cells, virus assembly, virus release from infected eukaryotic cells, or that is effective in nonspecifically inhibiting a virus titer increase or in nonspecifically reducing a virus titer level in a eukaryotic or mammalian host system.

An effective therapeutic compound can refer to a compound that can reduce, prevent, or treat a state, disorder, disease, or condition when the compound is administered to a subject. In particular embodiments, an effective therapeutic compound can prevent, reduce, or treat the likelihood of a viral infection. An amount of the therapeutic compound that is effective will vary depending on the compound, the disease and its severity and the age, weight, physical condition and responsiveness of the subject to be treated. The exact dose and formulation will depend on the purpose of the treatment and can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). In certain cases, "therapeutically effective amount" is used to mean an amount or dose sufficient to modulate, e.g., increase or decrease a desired activity e.g., by 10%, by 50%, or by 90%. Generally, a therapeutically effective amount is sufficient to cause an improvement in a clinically significant condition in the host following a therapeutic regimen involving one or more therapeutic compounds. The concentration or amount of the compound depends on the desired dosage and administration regimen. The effective amounts of compounds containing active agents include doses that partially or completely achieve the desired therapeutic, prophylactic, and/or biological effect. The actual amount effective for a particular application depends on the condition being treated and the route of administration.

Resistance Analysis of Therapeutics. The systems and methods of the present disclosure can be used to assess resistance to therapeutic compounds caused by mutations of a given protein represented in the deep mutational scanning libraries that result in reduced phenotypic susceptibility to a given antiviral therapeutic compound. In particular embodiments, in vitro resistance analysis studies can assess the potential barrier of a target virus to develop reduced susceptibility (i.e., resistance) to a therapeutic compound and to help in designing clinical studies. Virus resistant to a given therapeutic compound can be selected in cell culture, and the selection can provide a genetic threshold for resistance development. In particular embodiments, a therapeutic compound with a low genetic threshold may select for resistance with only one or two mutations. In contrast, a therapeutic compound with a high genetic threshold may require multiple mutations to select for resistance. In particular embodiments, the development of resistance in vitro can be assessed over a concentration range of a therapeutic compound spanning the anticipated concentration of the therapeutic compound that will be used in vivo. Selection of variants resistant to a therapeutic compound can be repeated more than once (e.g., with different strains of wild-type, with resistant strains, under high and low selective pressure) to determine if the same or different patterns of resistance mutations develop, and to assess the relationship of therapeutic compound concentration to the genetic barrier to resistance.

As discussed above, determining the mutations that might contribute to reduced susceptibility to a therapeutic compound using the systems and methods of the present disclosure can include sequencing barcodes after linking a barcode to a particular variant in a deep mutational scanning library. Identifying resistance mutations by this genotypic analysis can be useful in predicting clinical outcomes and supporting the proposed mechanism of action of a therapeutic compound. In particular embodiments, the pattern of mutations leading to resistance of a therapeutic compound can be compared with the pattern of mutations of other therapeutic compounds in the same class. In particular embodiments, resistance pathways can be characterized in several genetic backgrounds (i.e., strains, subtypes, genotypes) and protein variants can be obtained throughout the selection process to identify the order in which multiple mutations appear.

Phenotypic analysis determines if mutant viruses have reduced susceptibility to a therapeutic compound. In particular embodiments, using the systems and methods of the present disclosure, phenotypic analysis is performed when virions including protein variants of a cell-stored deep mutational scanning library are selected for resistance to a therapeutic compound. In particular embodiments, phenotypic resistance can be scored, for example, by an $EC_{50}$ value. An $EC_{50}$ value can refer to an effective concentration of a therapeutic compound which induces a response halfway between the baseline and maximum after a specified exposure time. In particular embodiments, an $EC_{50}$ value can be used as a measure of a therapeutic compound's potency. $EC_{50}$ can be expressed in molar units (M), where 1 M is equivalent to 1 mol/L. The fold resistant change can be calculated as the $EC_{50}$ value of the variant protein/$EC_{50}$ value of a reference protein. Phenotypic results can be determined with any standard virus assay (e.g., protein assay, viral RNA assay, polymerase assay, MTT cytotoxic assay, reporter or selectable marker expression). In particular embodiments, virus titer can be calculated as a function of the concentration of the therapeutic compound to obtain an $EC_{50}$ value. In particular embodiments, virus titer can be calculated by a plaque assay or focus forming assay. A plaque assay takes advantage of plaques that can arise through virus-mediated cell death within a monolayer of a cell culture when cells are infected with a cytopathic virus and typically requires plaques to grow until visible to the naked eye. The focus-forming assay can be used to titer non-cytopathic viruses. This assay usually relies on the detection of infected cells by immunostaining for viral antigen or via a genetically encoded fluorescent reporter. The shift in susceptibility (or fold resistant change) for a protein variant can be measured by determining the $EC_{50}$ value for the variant protein and comparing it to the $EC_{50}$ value of a reference protein. In particular embodiments, a reference protein can be a counterpart viral protein (equivalent viral protein having the same function from the same virus or from a different virus) from a wild-type virus, from a well-characterized wild-type laboratory strain, from a parental virus, or from a baseline clinical isolate done under the same conditions and at the same time. In particular embodiments, a wild-type virus can be naturally occurring. In particular embodiments, a wild-type virus has no mutations that confer drug resistance. In particular embodiments, a parental virus can be a virus having a viral protein that did not undergo mutagenesis as described herein to create a cell-stored barcoded deep mutational scanning library of variants of the viral protein. In particular embodiments, a parental virus can be a wild type virus. A baseline clinical isolate includes an isolate from a subject being screened for inclusion in a clinical trial or an isolate from a subject in a clinical trial before treatment in the trial has begun. The use of the $EC_{50}$ value for determining shifts in susceptibility can offer greater precision than an $EC_{90}$ or $EC_{95}$ value. The utility of a phenotypic assay depends on its sensitivity (i.e., its ability to measure shifts in susceptibility (fold resistance change) in comparison to a reference). Calculating the fold resistant change ($EC_{50}$ value of variant protein/$EC_{50}$ value of reference protein) allows for comparisons among phenotypic assays.

A viral protein may develop mutations that lead to reduced susceptibility to one antiviral therapeutic compound and can result in decreased or loss of susceptibility to other antiviral therapeutic compounds in the same therapeutic compound class. This observation is referred to as cross-resistance. Cross-resistance is not necessarily reciprocal, so it is important to evaluate both possibilities. For example, if virus X is resistant to drug A and drug B, and virus Y is also resistant to drug A, virus Y may still be sensitive to drug B. In particular embodiments, the effectiveness of a therapeutic compound against viruses resistant to other approved therapeutic compounds in the same class and the effectiveness of approved therapeutic compounds belonging to a given class against viruses resistant to a therapeutic compound belonging to that same class can be evaluated by phenotypic analyses. In particular embodiments, cross-resistance can be analyzed between therapeutic classes in instances where more than one therapeutic compound class targets a single protein or protein complex (e.g., nucleoside reverse transcriptase inhibitors (NRTIs) and non-nucleoside reverse transcriptase inhibitors (NNRTIs), which both target the HIV-encoded reverse transcriptase). Variant viral proteins representative of the breadth of diverse mutations and combinations of mutations known to confer reduced susceptibility to therapeutic compounds in the same class can be tested for phenotypic susceptibility to a new therapeutic compound belonging to that same class.

Therapeutic Treatment Neutralization—Antibodies. Two primary countermeasures against emerging viruses are vaccines and antibody therapeutics, both of which generally target viral entry proteins. The barcoded virus libraries can be used to identify viral mutations that affect viral sensitivity to neutralization by antibodies and sera. The resulting data can inform the choice and evaluation of vaccines and therapeutic antibodies used to treat emerging viruses. In particular embodiments, these approaches can be used to map the epitope of monoclonal antibodies rapidly and in mutation-level detail. Further, quantifying the effect of all possible viral mutations on antibody neutralization is useful for resistance analysis of antibody drug candidates. Such data can also be used to predict if a particular viral genotype will be susceptible to neutralization by a particular antibody, facilitating personalized use of antibody immunotherapies.

Figures 8A, 8B, 8C:
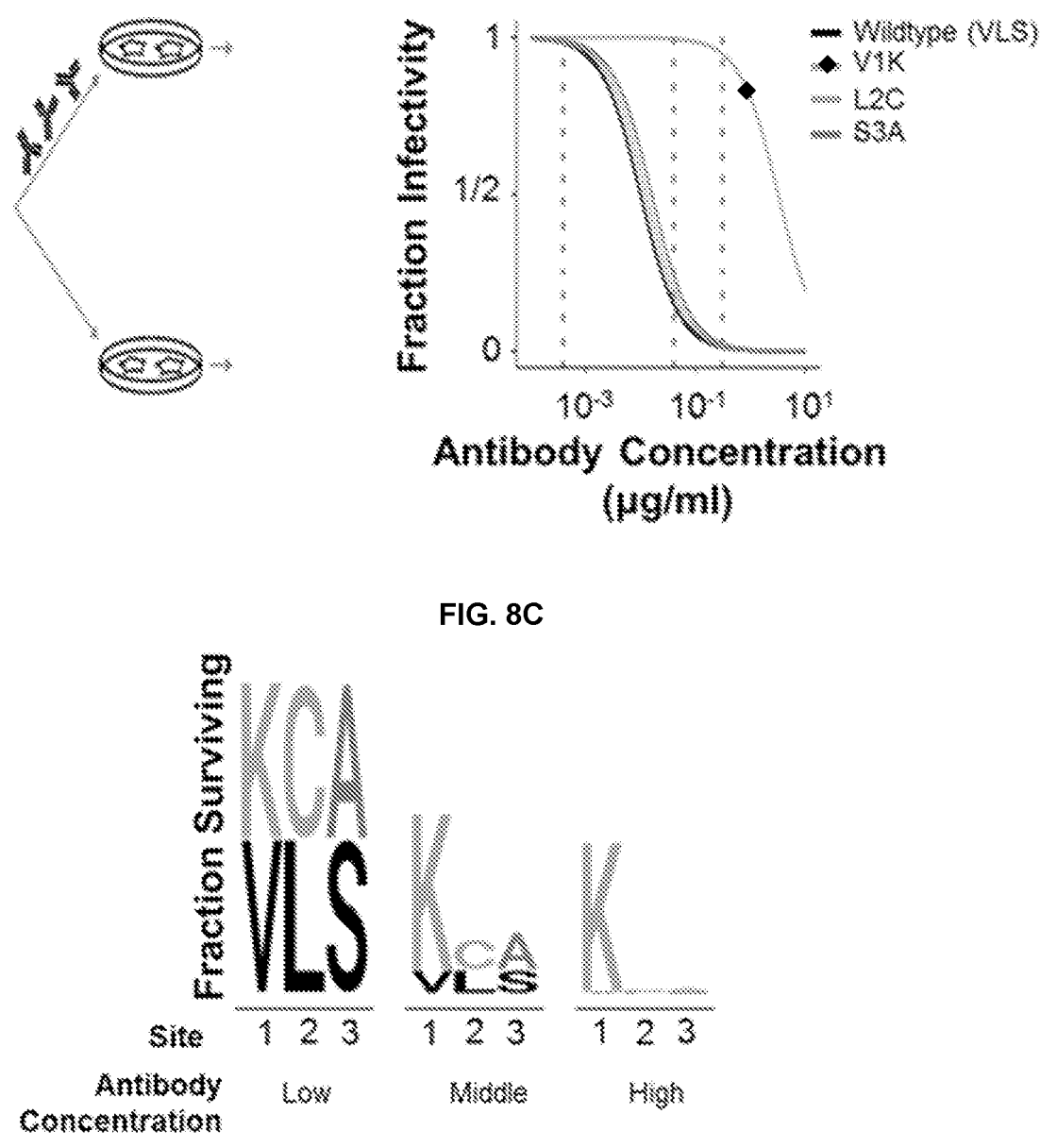

The sensitivity of a virus to an antibody or serum sample can be quantified by a neutralization curve (FIGS. 8A-8C). Such curves are conventionally measured on individual viral variants, but they can in principle be measured for many variants at once using deep sequencing. In prior work, deep sequencing of viral libraries has been used to measure antibody selection on viral mutations [Doud, et al. (2017) PLoS Pathog. 13(3): e1006271; Dingens et al. (2017) Cell Host & Microbe 21: 777-787; Doud et al. (2018) bioRxiv DOI: 210468]. Because these libraries were not barcoded, however, it was only feasible to use one or a few antibody concentrations. With the barcoded libraries disclosed herein, multiple concentrations to interpolate full curves can be tested. In particular embodiments, curves for >$10^4$ mutants can be generated. In these embodiments, it can be more informative to represent the results in logo plots rather than overlaying vast numbers of curves (FIGS. 8A-8C). In particular embodiments, a sequence logo plot can be a graphical representation of sequence conservation of nucleotides or amino acids. A sequence logo can be created from a collection of aligned sequences and depicts the consensus sequence and diversity of the sequences. In particular embodiments, sequence logos can be used to depict sequence characteristics such as protein-binding sites in DNA or functional units in proteins. In particular embodiments, sequence logos can be used to depict the preference for a nucleotide base or an amino acid residue at a given position in a nucleotide sequence or in an amino acid sequence, respectively. In particular embodiments, sequence logos can be used to depict the effect of each amino acid or nucleotide on a selective pressure, such as antibody neutralization or drug inhibition as described above.

In particular embodiments, to obtain neutralization curves, the absolute fraction of each viral variant that survives exposure to an antibody or sera can be measured. For an absolute standard, virions with an unrelated entry protein not affected by the antibody or sera can be used. FIG. 7 shows the MLV entry protein as this standard. The RD114 entry protein can also be used. Both MLV and RD114 are amphotropic, and antibodies to them are not found in human sera. In particular embodiments, any viral entry protein not affected by the antibody or sera can be used as an absolute standard. In particular embodiments, an envelope glycoprotein described above can be used as an absolute standard. With these standards, neutralization curves can be generated by incubating the virus libraries at several antibody concentrations, infecting them into cells, and sequencing the barcodes (the viruses have RNA genomes, so neutralized viruses do not contribute to the DNA pool). The fraction of each mutant surviving relative to the standards can be computed. In particular embodiments, the use of two standards will allow detection of whether one is unexpectedly affected by the antibody. Neutralization curves can be fit and the data can be represented as in FIG. 8B.

In particular embodiments, neutralization curves for all amino acid mutants for the following antibodies can be obtained: those in the ZMapp cocktail against Ebola [Qiu et al. (2014) Nature 514(7520): 47-53; Qiu et al. (2016) Science Translational Medicine 8(329): 329ra33]; LCA60, REGN3051, and REGN3048 against MERS-CoV [Pascal et al. (2015) PNAS 112(28): 8738-8743; Corti et al. (2015) PNAS 112(33): 10473-10478]; 37.2D, 8.9F, 19.7E, 37.7H and 12.1F against Lassa [Mire et al. (2017) Nature Medicine 23: 1146]; and m102.4 against Nipah [Geisbert et al. (2014) Science Translational Medicine 6: 242ra82-242ra82]. These antibodies are under consideration for use in humans, so mapping mutations that affect neutralization will provide insight into the interaction surfaces and aid identification of viral resistance mutations that arise during use. For instance, the ZMapp antibody cocktail [Qiu et al. (2014), supra] used during the Ebola outbreak was created without specific consideration of the viral strain causing the outbreak. In future outbreaks, the results could guide the selection of which antibodies would perform optimally against relevant viral strains.

A second consideration is that Lassa and Ebola viruses are relatively proficient at evading antibody neutralization via evolution and glycan shielding [Sommerstein et al. (2015) PLoS Pathogens 11: e1005276; Jahrling et al. (1985) Transactions of the Royal Society of Tropical Medicine and Hygiene 79: 380-384; Francica et al. (2010) PLoS Pathogens 6: e1001098]. It is therefore beneficial to choose antibodies for immunotherapy that are resistant to evolutionary escape. By mapping how all mutations affect neutralization, the ease with which the viruses can escape different antibodies can be compared, thereby guiding selection of the most escape-resistant antibodies.

In particular embodiments, sera samples can be obtained from vaccine studies to map mutations that affect resistance to these sera. This work can functionally map the epitopes targeted by the vaccines and enable correlation of animal-to-animal variation in protection with variation in epitope targeting, both of which could help inform further immunogen design.

Engineering more effective antibodies. The systems and methods of the present disclosure can be used to engineer antibodies that are more effective in neutralizing a viral protein. In particular embodiments, a method of engineering a second, more effective therapeutic antibody from a first antibody against a virus using a cell-stored barcoded deep mutational scanning library can include: obtaining the library including storage cells, wherein at least 90% of storage cells include (or, in particular embodiments, each storage cell includes) at most a single copy of a non-self-inactivating viral vector including a single homozygous barcoded variant nucleotide sequence from a set of homozygous barcoded variant sequences in the library integrated into the storage cell's genome, wherein the set of homozygous barcoded variant nucleotide sequences collectively encode viral protein variants including at least 15 amino acid substitutions at at least 95% of amino acid positions of the viral protein; transfecting the storage cells with plasmids including sequences encoding viral proteins for production of virions; culturing the transfected storage cells to produce virions, wherein each virion includes a homozygous barcoded variant sequence encoding a viral protein variant of the virus; exposing target cells to (i) the produced virions and (ii) the first antibody; sequencing barcodes following exposure to the first antibody, wherein the barcodes associated with variant nucleotide sequences conferring an ability to evade the first antibody increase in frequency and the barcodes associated with variant nucleotide sequences conferring an inability to evade the first antibody decrease in frequency; comparing variant nucleotide sequences conferring an ability to evade the first antibody with the nucleotide sequence of a reference viral protein that the first antibody binds; modifying amino acid residues in the first antibody based on the comparing and on a known crystal structure of the reference viral protein/first antibody complex, thereby engineering a second, more effective therapeutic antibody from a first antibody against the virus. In particular embodiments, engineering a more effective antibody can include the method described in Diskin et al. (2013) J. Exp. Med. 210(6): 1235-1249.

Naturally occurring antibody structural units include a tetramer. Each tetramer includes two pairs of polypeptide chains, each pair having one light chain and one heavy chain. The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, MD (1987 and 1991)), or Chothia & Lesk, J. Mol. Biol., 196:901-917 (1987); Chothia et al., Nature, 342:878-883 (1989).

The carboxy-terminal portion of each chain defines a constant region that can be responsible for effector function. Examples of effector functions include: C1q binding and complement dependent cytotoxicity (CDC); antibody-dependent cell-mediated cytotoxicity (ADCC); antibody-dependent phagocytosis (ADCP); down regulation of cell surface receptors (e.g. B cell receptors); and B cell activation.

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989).

Unless otherwise indicated, the term "antibody" includes, in addition to antibodies including two full-length heavy chains and two full-length light chains as described above, variants, derivatives, and fragments thereof, examples of which are described below. Furthermore, unless explicitly excluded, antibodies can include monoclonal antibodies, human antibodies, bispecific antibodies, polyclonal antibodies, linear antibodies, minibodies, domain antibodies, synthetic antibodies, chimeric antibodies, antibody fusions, and fragments thereof, respectively. In particular embodiments, antibodies (e.g., full length antibodies) can be produced in human suspension cells.

In particular embodiments, monoclonal antibodies refer to antibodies produced by a clone of B cells or hybridoma cells. In particular embodiments, monoclonal antibodies are identical to each other and/or bind the same epitope, except for possible antibodies containing naturally occurring mutations or mutations arising during production of a monoclonal antibody. In particular embodiments, in contrast to polyclonal antibody preparations, which include different antibodies directed against different epitopes, each monoclonal antibody of a monoclonal antibody preparation is directed against a single epitope on an antigen.

A "human antibody" is one which includes an amino acid sequence which corresponds to that of an antibody produced by a human or a human cell or derived from a non-human source that utilizes human antibody repertoires or other human antibody-encoding sequences.

A "human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda MD (1991), vols. 1-3. In particular embodiments, for the $V_L$, the subgroup is subgroup kappa I as in Kabat et al., supra. In particular embodiments, for the $V_H$, the subgroup is subgroup III as in Kabat et al., supra.

In particular embodiments, an antibody fragment is used. An "antibody fragment" denotes a portion of a complete or full length antibody that retains the ability to bind to an epitope. Examples of antibody fragments include Fv, single chain Fv fragments (scFvs), Fab, Fab', Fab'-SH, F(ab')$_2$, diabodies, linear antibodies, Fc, and/or any biologically effective fragments of an immunoglobulin that bind specifically to an epitope described herein. Antibodies or antibody fragments include all or a portion of polyclonal antibodies, monoclonal antibodies, human antibodies, humanized antibodies, synthetic antibodies, chimeric antibodies, bispecific antibodies, mini bodies, and linear antibodies.

A single chain variable fragment (scFv) is a fusion protein of the variable regions of the heavy and light chains of immunoglobulins connected with a short linker peptide. Fv fragments include the VL and VH domains of a single arm of an antibody. Although the two domains of the Fv fragment, VL and VH, are coded by separate genes, they can be joined, using, for example, recombinant methods, by a synthetic linker that enables them to be made as a single protein chain in which the VL and VH regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including $V_L$, $V_H$, $C_L$ and $C_{H1}$ domains. A F(ab')$_2$ fragment is a bivalent fragment including two Fab fragments linked by a disulfide bridge at the hinge region. For discussion of Fab and F(ab')$_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90 (1993) 6444-6448. Dual affinity retargeting antibodies (DART™; based on the diabody format but featuring a C-terminal disulfide bridge for additional stabilization (Moore et al., Blood 117, 4542-51 (2011)) can also be used. Antibody fragments can also include isolated CDRs. For a review of antibody fragments, see Hudson, et al., Nat. Med. 9 (2003) 129-134.

Antibody fragments can be made by various techniques, including proteolytic digestion of an intact antibody as well as production by recombinant host-cells (e.g., human suspension cell lines, E. coli or phage), as described herein. Antibody fragments can be screened for their binding properties in the same manner as intact antibodies.

A neutralizing antibody can refer to an antibody that, upon epitope binding, can reduce biological function of its target antigen. In particular embodiments neutralizing antibodies can reduce (i.e., neutralize) viral infection of cells. In particular embodiments percent neutralization can refer to a percent decrease in viral infectivity in the presence of the antibody, as compared to viral infectivity in the absence of the antibody. For example, if half as many cells in a sample become infected in the presence of an antibody, as compared to in the absence of the antibody, this can be calculated as 50% neutralization. In particular embodiments "neutralize viral infection" can refer to at least 40% neutralization, at least 50% neutralization, at least 60% neutralization, at least 70% neutralization, at least 80% neutralization, or at least 90% neutralization of viral infection. In particular embodiments, the antibodies can block viral infection (i.e., 100% neutralization). In particular embodiments, the anti-viral antibodies can inhibit envelope fusion with target cells, which can result in neutralization of viral infection. Inhibition of viral envelope fusion to target cells can be at least 40%, inhibition, at least 50%, inhibition, at least 60%, inhibition, at least 70%, inhibition, at least 80%, inhibition, or at least 90%, inhibition, as compared to viral envelope fusion in the absence of the anti-viral antibody.

In particular embodiments, an antibody that neutralizes a viral infection is effective against the virus.

Host adaptation. To enable identification of host adaptation, how mutations affect each viral entry protein's ability to mediate infection of cells from relevant host species can be measured (FIG. 9). In particular embodiments, methods described herein measure the preference for each amino acid at each site in a viral entry protein under selection to infect different cell lines.

Using an HA library as an example, the libraries can be used to measure the functional effects of all mutations to HA. To do this, the library-carrying cells can be transfected with the helper plasmids (first step of FIG. 7) both with and without adding VSV-G. In the presence of VSV-G, all virions will be infectious. In the absence of VSV-G, infectivity will depend on HA. The virions can be used to infect cells (e.g., MDCK-SIAT1 cells). Then, non-integrated viral cDNA can be isolated and the barcodes can be sequenced to quantify the variant frequencies in each case. On an Illumina HiSeq 4000, the cost of sequencing $5 \times 10^5$ barcodes to 10× coverage is currently $25. Since the typical single amino acid mutant will have 15 barcodes, this gives >100 counts for the typical mutation in the unselected condition (with VSV-G). Counts in the selected condition will vary depending on the functionality of that particular HA mutant. Algorithms to extract functional information from deep mutational scanning counts have been described and implemented (see FIG. 7 adapted from Bloom (2015) BMC Bioinformatics 16: 168 and on the World Wide Web at jbloomlab.githubio/dms_tools2). These algorithms can be used to estimate the "preference" of each site in HA for each amino acid (see FIG. 1 and FIG. 9). Such preferences are a useful way to represent the data since they can be related to viral evolution in nature using phylogenetic methods [Hilton, et al. (2017) PeerJ 5: e3657]. In particular embodiments, the preferences can be estimated using barcode counts for single amino acid mutants. Preferences for multiple can also be estimated.

As exemplary uses, the libraries can be used to map how all mutations to entry proteins of four emerging viruses (e.g., Ebola, Lassa, Nipah, MERS-CoV) affect capacity to infect cells from relevant species. Ebola, Lassa, Nipah, and MERS-CoV all circulate in animal reservoirs but occasionally transmit to humans. These viruses could therefore cause epidemics or pandemics if they adapt to better infect and transmit among humans. Although these four viruses are BSL-3 or BSL-4, their entry proteins can be safely used on non-replicative viral virions at BSL-2 based on the systems and methods disclosed herein.

Differences that are host-specific rather than cell-line specific can often be more interesting. Accordingly, in particular embodiments, multiple cell lines for all hosts can be used to identify mutations that are robustly favored in numerous or all cell lines of that host.

The animal reservoir of Ebola virus is probably bats. In particular embodiments, how mutations affect infection of the following cell lines can be mapped: HuH7 (human liver), A549 (human lung epithelial), BEAS-2B (human lung epithelial), HypLu/45.1 (fruit bat lung), and/or HypNi/1.1 (fruit bat kidney).

MERS-CoV likely also has a reservoir in bats and can infect humans via the intermediate host of camels. In particular embodiments, how mutations affect infection of the following cell lines can be mapped: RoNi/7 (Egyptian fruit bat), PipNi (pipestrelle bat), TT-R.B (dromedary camel), Calu-3 (human lung), and/or MRC-5 (human lung). In addition, because the DPP4 receptor for Spike is thought to be a major determinant of host range, infection in 293T cells engineered to express DPP4 from human, bat, and camel can be mapped.

Lassa virus has a reservoir in multimammate rats. In particular embodiments, how mutations affect infection of the following cell lines can be mapped: A549 (human lung epithelial), HuH7 (human liver), RLE-6TN (rat lung), and/or H-4-II-E (rat liver).

In particular embodiments, (i) duplicate libraries, (ii) the existence of a few barcodes to hundreds of barcodes for each amino acid mutant, and (iii) algorithms similar to those in [Haddox et al. (2018) eLife 7:e34420] can be used to quantify noise, and identify cell-line-specific differences that exceed this noise.

Results across more than one strain of a virus can be used to determine the extent that mutations are generally host adaptive versus strain-specific effects because viral strains can be genetically diverse (see algorithms in [Haddox et al. (2018) eLife 7:e34420]). Using, for example, two or more strains of a virus allows assessment of how well the measurements can be generalized across strains. In particular embodiments, assessing strain-specificity can be important in order to use the methods to better score host adaptation. Another way to examine this question is via the multiple mutants in the libraries. Particularly, whether effects of multiple mutations are the sum of the effects of the individual mutations can be assessed under an optimal scale as determined in Sailer et al. (2017) Genetics 205: 1079-1088.

As indicated, in particular embodiments, measurements can be used to develop algorithms that score a virus's host adaptation from its sequence. This will advance assessment of the risk of viral host jumps [Russell, et al. (2014) eLife 3: e03883], and improve the ability to identify viral adaptation during human outbreaks.

Figures 10, 11A, 11B:
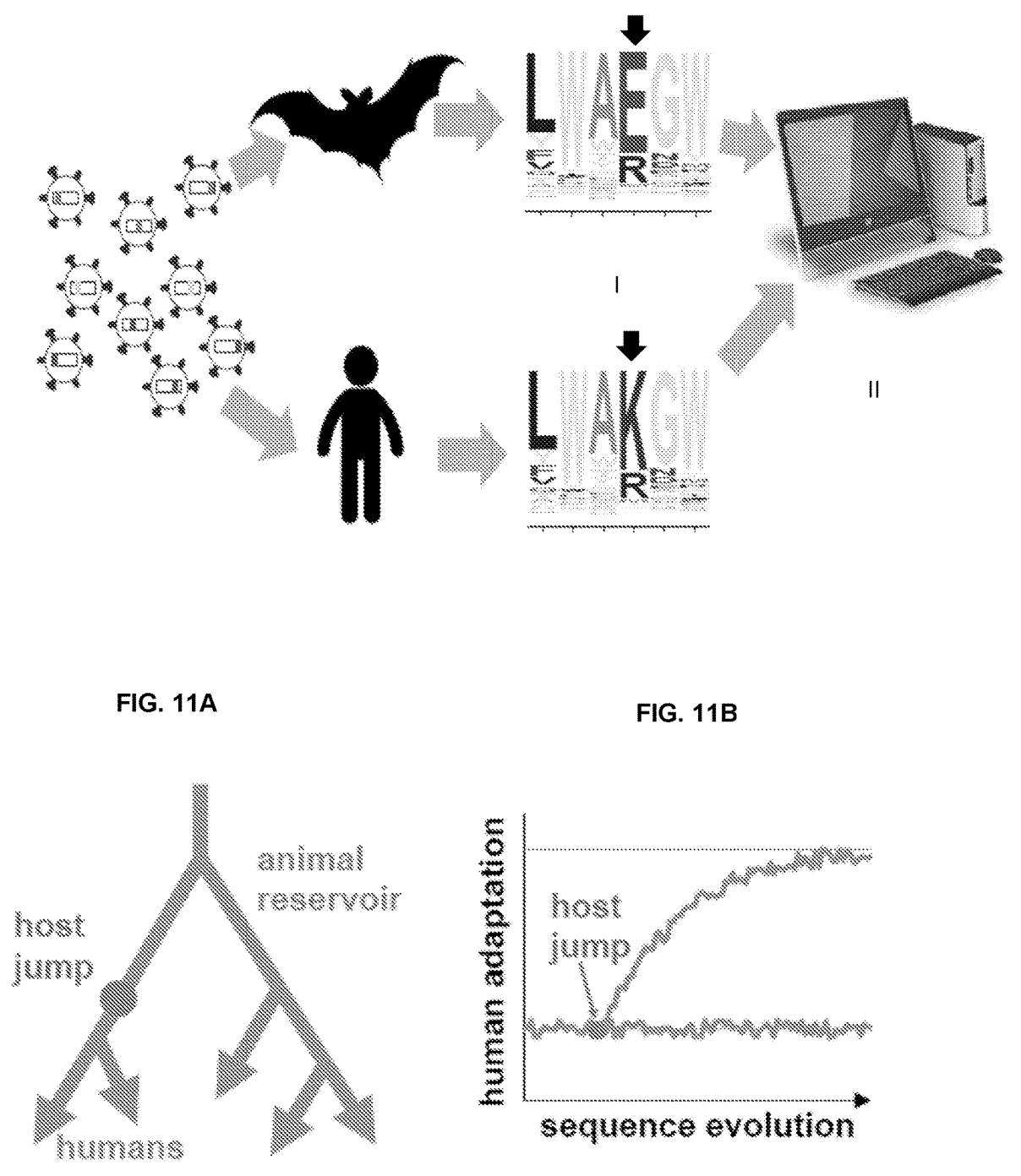

In particular embodiments, host adaptation can be scored as in FIG. 10. In particular embodiments, host scoring can be performed using an additive model. For example, if $\pi_{r,a}^h$ is the preference for amino acid a at site r measured in cells from host h (e.g., the logo plots in FIG. 8C), then the adaptation to host h of sequence s is scored as $$S_h(s) = \sum_r \log(\pi_{r,s_r}^h)$$

where $s_r$ is the amino acid at site r of sequence s.

Historical data can be used to evaluate the scoring models. While additive models might seem simplistic, similar models informed by deep mutational scanning discriminated the evolutionary success of human influenza virus lineages [Lee, et al. (2018) Deep mutational scanning of hemagglutinin helps predict evolutionary fates of human H3N2 influenza variants. Proceedings of the National Academy of Sciences, 115(35), E8276-E8285], which is probably a harder problem since fitness differences between human influenza variants are likely smaller than those between variants of emerging viruses that have and have not adapted to humans.

As measurements for multiple mutations and different strain backgrounds are accumulated, epistatic models that incorporate non-additivity in forms can be explored (see, e.g., [Louie, et al. (2018) Proceedings of the National Academy of Sciences: 201717765; Hopf, et al. (2017) Nature Biotechnology 35: 128; Poelwijk, et al. (2017) Learning the pattern of epistasis linking genotype and phenotype in a protein. bioRxiv: 213835; Sailer & Harms (2017) PLoS Computational Biology 13: e1005541].

In particular embodiments, the systems and methods disclosed herein can be used to assess whether antigenic selection drives viral evolution. For example, it is unclear if immune selection drives the evolution of the emerging viruses such as Ebola, Lassa, and Nipah. Uses of the libraries disclosed herein can identify sites where mutations affect immune recognition. Whether these immune-targeted sites evolve faster than other sites can be assessed. For example, one can fit codon-substitution models where the relative rate of amino acid substitution (dN/dS) is uniform across the gene or takes on a different value at sites experiments map as being under immune selection. HyPhy [Pond & Muse (2005) HyPhy: hypothesis testing using phylogenies. In: Statistical Methods in Molecular Evolution, Springer. pp. 125-181] can be used to fit these models, and a likelihood-ratio test to evaluate the support for the partitioned model versus the nested non-partitioned alternative can be used. Issues associated with strain specificity can also apply in these uses. That is, it may be that the antigenic effects of mutations vary among the strains of a virus. However, this issue can be assessed. These uses are based on the idea that epitopes are similar among different sera, but different sera could target very different epitopes due to host-to-host variation. In that case the generality of the mapping is reduced, but the throughput of disclosed methods then provides a way to characterize this variation, which is interesting in its own right.

Particular embodiments can assess the viral entry proteins of: [virus (entry protein)]: Chikungunya (E1 Env and E2 Env), Ebola glycoprotein (EBOV GP), Hendra (F glycoprotein and G glycoprotein), hepatitis B (large (L), middle (M), and small (S)), hepatitis C (glycoprotein E1 and glycoprotein E2), HIV envelope (Env), influenza hemagglutinin (HA), Lassa virus envelope glycoprotein (GPC), measles (hemagglutinin glycoprotein (H) and fusion glycoprotein F0 (F)), MERS-CoV (Spike (S)), Nipah (fusion glycoprotein F0 (F) and glycoprotein G), Rabies virus glycoprotein (RABV G), RSV (fusion glycoprotein F0 (F) and glycoprotein G), and SARS-CoV (Spike (S)), among many others.

Kits. Combinations of elements of the deep mutational scanning libraries disclosed herein can be provided as kits. Kits of the present disclosure can include: a viral (e.g., lentiviral) vector for insertion of viral entry protein variant sequences; expression plasmids including viral non-surface proteins; a plasmid including an unrelated functional viral entry protein; and one or more cell lines. In particular embodiments, the viral vector includes a barcode. In particular embodiments, the viral vector includes sequences to facilitate sequencing. In particular embodiments, the viral vector includes a reporter gene. In particular embodiments, the viral vector includes a functional U3. In particular embodiments, the viral non-surface proteins include one or more of Gag, Pol, Tat, and Rev. In particular embodiments, the unrelated functional viral entry protein is VSV-G. In particular embodiments, the one or more cell lines include 293T and/or MDCK-SIAT1-TMPRSS2. In particular embodiments kits can include one or more cell-stored libraries as disclosed herein and/or one or more retroviral particle libraries made by transfecting cells of a cell-stored library with helper plasmids.

Kits can include further instructions for using the kit, for example, instructions regarding cloning of variant sequences into the viral vector, transfection of plasmids, selection of cells expressing a reporter protein, and propagation of the cell-stored library. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In particular embodiments, kits can also include laboratory supplies needed to use the kit effectively, such as cell culture media, buffers, enzymes, sterile plates, sterile flasks, pipettes, gloves, and the like. Variations in contents of any of the kits described herein can be made.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A method of creating a cell-stored barcoded deep mutational scanning library of variants of a viral protein including:
   Obtaining a set of barcoded variant nucleotide sequences wherein the set collectively encodes viral protein variants including at least 15 amino acid substitutions at at least 95% of amino acid positions of the viral protein;
   Infecting a population of cells with an amount of virions to generate storage cells wherein each virion includes barcoded variant nucleotide sequences of the set and wherein after the infecting at least 90% of storage cells include a non-self-inactivating viral vector including a single homozygous barcoded variant nucleotide sequence of the set integrated into the storage cell's genome
   thereby creating a cell-stored barcoded deep mutational scanning library of variants of a viral protein.
2. The method of embodiment 1, wherein the set of barcoded variant nucleotide sequences collectively encode viral protein variants including at least 17 amino acid substitutions at at least 95% of amino acid positions of the viral protein.
3. The method of embodiment 1 or 2, wherein the set of barcoded variant nucleotide sequences collectively encode viral protein variants including at least 19 amino acid substitutions at all amino acid positions of the viral protein.
4. The method of any one of embodiments 1-3, wherein the viral protein variants include viral entry protein variants.
5. The method of any one of embodiments 1-3, wherein the viral protein variants include viral Gag Pol variants.
6. The method of any one of embodiments 1-3, wherein the viral protein variants include viral Tat variants.
7. The method of any one of embodiments 1-3, wherein the viral protein variants include viral Rev variants.
8. The method of any one of embodiments 1-7, wherein the viral vector includes a retroviral vector.
9. The method of any one of embodiments 1-8, wherein the viral vector includes a lentiviral vector.
10. The method of any one of embodiments 1-9, wherein the viral vector includes a functional U3.
11. The method of any one of embodiments 1-10, wherein the viral vector includes sequences to facilitate sequencing.
12. The method of any one of embodiments 1-11, wherein the viral vector includes a gene encoding a reporter or selectable marker.
13. The method of embodiment 12, wherein expression of the reporter or selectable marker is used to select storage cells that have integrated the viral vector.
14. The method of embodiment 12 or 13, wherein the gene encoding the reporter or selectable marker is linked to each barcoded variant sequence by a linker.
15. The method of embodiment 14, wherein the linker is selected from *Thosea asigna* virus 2A, porcine teschovirus-1 P2A, equine rhinitis A virus E2A, and foot-and-mouth disease virus F2A.
16. The method of any one of embodiments 12-35, wherein the reporter and each viral variant protein are expressed from different promoters.
17. The method of any one of embodiments 1-16, wherein the barcode includes 4 to 30 nucleotides.
18. The method of any one of embodiments 1-17, wherein the barcode is located after the stop codon of the variant sequence.
19. The method of any one of embodiments 1-18, wherein the storage cells are derived from 293T, HEK293T/17, HEK293F, HEK293S, HEK293SGH, EK293FTM, HEK293SGGD, GP2-293, HeLa, HeLa S3, HeLa B, HeLa T4, COS, COS-1, COS-6, COS-M6A, COS-7, A549, MDCK, HepG2, C2C12, THP-1, HUDEP-2, C8161, CCRF-CEM, MOLT, mIMCD-3, NHDF, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, BS-C-1, monkey kidney epithelial, BALB/3T3 mouse embryo fibroblast, 3T3 Swiss, 3T3-L1, 132-d5 human fetal fibroblasts, 10.1 mouse fibroblasts, 3T3, 721, 9L, A2780, A2780ADR, A2780cis, A172, A20, A253, A431, A-549, ALC, B16, B35, BCP-1, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, Hepa1c1c7, HL-60, HMEC, HT-29, JY, K562, Ku812, KCL22, KG1, KYO1, LNCap, Ma-Mel 1-48, MC-38, MCF-7, MCF-10A, MDA-MB-231, MDA-MB-468, MDA-MB-435, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT2, RenCa, RIN-5F, RMA/RMAS, Saos-2, Sf-9, SkBr3, T2, T-47D, T84, THP1, U373, U87, U937, VCaP, Vero, WM39, WT-49, X63, YAC-1, or YAR cells.

20. The method of any one of embodiments 1-19, wherein the infecting is at a low multiplicity of infection (MOI).

21. The method of embodiment 20, wherein the low MOI is from 0.01 to 0.5.

22. The method of any one of embodiments 1-21, wherein the storage cells are passaged to propagate the library.

23. The method of any one of embodiments 4, and 8-22, wherein the method further includes:
    Transfecting the storage cells with plasmids including sequences encoding viral Gag Pol, Tat, and Rev proteins; and
    Culturing the transfected storage cells to produce non-replicative virions that can be assessed at biosafety level (BSL)-2.

24. The method of any one of embodiments 5, and 8-22, wherein the method further includes:
    Transfecting the storage cells with plasmids including sequences encoding Tat, Rev, and an entry protein; and
    Culturing the transfected storage cells to produce non-replicative virions that can be assessed at BSL-2.

25. The method of any one of embodiments 6, and 8-22, wherein the method further includes:
    Transfecting the storage cells with plasmids including sequences encoding an entry protein, Gag Pol, and Rev; and
    Culturing the transfected storage cells to produce non-replicative virions that can be assessed at BSL-2.

26. The method of any one of embodiments 7, and 8-22, wherein the method further includes:
    Transfecting the storage cells with plasmids including sequences encoding an entry protein, Gag Pol, and Tat; and
    Culturing the transfected storage cells to produce non-replicative virions that can be assessed at BSL-2.

27. The method of any one of embodiments 23-26, wherein the proteins encoded by the plasmids are expressed in the storage cells.

28. The method of any one of embodiments 1-27, wherein the virus is selected from Chikungunya, Ebola, Hendra, hepatitis B, hepatitis C, human immunodeficiency virus (HIV)-1, HIV-2, simian immunodeficiency virus (SIV), influenza, Lassa, measles, Middle East respiratory syndrome coronavirus (MERS-CoV), Nipah, Rabies, respiratory syncytial virus (RSV), and severe acute respiratory syndrome coronavirus (SARS-CoV).

29. The method of any one of embodiments 4-28, wherein the viral entry protein variants include variants of a viral entry protein selected from influenza hemagglutinin (HA), HIV envelope (Env), Chikungunya E1 Env, Chikungunya E2 Env, Ebola glycoprotein (EBOV GP), Hendra F glycoprotein, Hendra G glycoprotein, hepatitis B large (L), hepatitis B middle (M), hepatitis B small (S), hepatitis C glycoprotein E1, hepatitis C glycoprotein E2, Lassa virus envelope glycoprotein (LASV GP), measles hemagglutinin glycoprotein (H), measles fusion glycoprotein F0 (F), MERS-CoV Spike (S), Nipah fusion glycoprotein F0 (F), Nipah glycoprotein G, Rabies virus glycoprotein G (RABV G), RSV fusion glycoprotein F0 (F), RSV glycoprotein G, and SARS-CoV Spike (S).

30. A cell-stored barcoded deep mutational scanning library of variants of a viral protein including: storage cells, wherein at least 90% of the storage cells include a non-self-inactivating viral vector including a single homozygous barcoded variant nucleotide sequence encoding a viral protein variant from a set of homozygous barcoded variant nucleotide sequences in the library integrated into the storage cell's genome, wherein the set of homozygous barcoded variant nucleotide sequences collectively encode viral protein variants including at least 15 amino acid substitutions at at least 95% of amino acid positions of the viral protein.

31. The library of embodiment 30, wherein the set of homozygous barcoded variant nucleotide sequences collectively encode viral protein variants including at least 17 amino acid substitutions at at least 95% of amino acid positions of the viral protein.

32. The library of embodiment 30 or 31, wherein the set of homozygous barcoded variant nucleotide sequences collectively encode viral protein variants including at least 19 amino acid substitutions at all amino acid positions of the viral protein.

33. The library of any one of embodiments 30-32, wherein the viral protein variants include viral entry protein variants.

34. The library of any one of embodiments 30-32, wherein the viral protein variants include viral gag pol variants.

35. The library of any one of embodiments 30-32, wherein the viral protein variants include viral Tat variants.

36. The library of any one of embodiments 30-32, wherein the viral protein variants include viral Rev variants.

37. The library of any one of embodiments 30-36, wherein the viral vector includes a retroviral vector.

38. The library of any one of embodiments 30-37, wherein the viral vector includes a lentiviral vector.

39. The library of any one of embodiments 30-38, wherein the viral vector includes a functional U3.

40. The library of any one of embodiments 30-39, wherein the viral vector includes sequences to facilitate sequencing.

41. The library of any one of embodiments 30-40, wherein the viral vector includes a gene encoding a reporter or selectable marker.

42. The library of embodiment 41, wherein expression of the reporter or selectable marker is used to select storage cells that have integrated the viral vector.

43. The library of embodiment 41 or 42, wherein the gene encoding the reporter or selectable marker is linked to each barcoded variant sequence by a linker.

44. The library of embodiment 43, wherein the linker is selected from *Thosea asigna* virus 2A, porcine teschovirus-1 P2A, equine rhinitis A virus E2A, and foot-and-mouth disease virus F2A.

45. The library of any one of embodiments 41-44, wherein the viral vector includes a first promoter to express the reporter or selectable marker and a second promoter to express the viral variant protein.

46. The library of any one of embodiments 30-45, wherein each barcoded variant sequence includes a barcode 4 to 30 nucleotides in length.

47. The library of any one of embodiments 30-46, wherein each barcoded variant sequence includes a barcode located after the stop codon of the variant sequence.

48. The library of any one of embodiments 30-47, wherein the storage cells are derived from 293T, HEK293T/17, HEK293F, HEK293S, HEK293SGH, EK293FTM, HEK293SGGD, GP2-293, HeLa, HeLa S3, HeLa B, HeLa T4, COS, COS-1, COS-6, COS-M6A, COS-7, A549, MDCK, HepG2, C2C12, THP-1, HUDEP-2, C8161, CCRF-CEM, MOLT, mIMCD-3, NHDF, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, BS-C-1, monkey kidney epithelial, BALB/3T3 mouse embryo fibroblast, 3T3 Swiss, 3T3-L1, 132-d5 human fetal fibroblasts, 10.1 mouse fibroblasts, 3T3, 721, 9L, A2780, A2780ADR, A2780cis, A172, A20, A253, A431, A-549, ALC, B16, B35, BCP-1, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, Hepa1c1c7, HL-60, HMEC, HT-29, JY, K562, Ku812, KCL22, KG1, KYO1, LNCap, Ma-Mel 1-48, MC-38, MCF-7, MCF-10A, MDA-MB-231, MDA-MB-468, MDA-MB-435, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT2, RenCa, RIN-5F, RMA/RMAS, Saos-2, Sf-9, SkBr3, T2, T-47D, T84, THP1, U373, U87, U937, VCaP, Vero, WM39, WT-49, X63, YAC-1, and YAR cells.

49. The library of any one of embodiments 33, and 37-48, wherein the storage cells further include plasmids including sequences encoding viral Gag Pol, Tat, and Rev proteins.

50. The library of any one of embodiments 33, and 37-48, wherein the storage cells further include a plasmid including a sequence encoding a functional unrelated viral entry protein.

51. The library of any one of embodiments 34, and 37-48, wherein the storage cells further include plasmids including sequences encoding Tat, Rev, and an entry protein.

52. The library of any one of embodiments 35, and 37-48, wherein the storage cells further include plasmids including sequences encoding an entry protein, Gag Pol, and Rev.

53. The library of any one of embodiments 36, and 37-48, wherein the storage cells further include plasmids including sequences encoding an entry protein, Gag Pol, and Tat.

54. The library of any one of embodiments 30-53, wherein the virus is selected from Chikungunya, Ebola, Hendra, hepatitis B, hepatitis C, human immunodeficiency virus (HIV), simian immunodeficiency virus (SIV), influenza, Lassa, measles, Middle East respiratory syndrome coronavirus (MERS-CoV), Nipah, Rabies, respiratory syncytial virus (RSV), and severe acute respiratory syndrome coronavirus (SARS-CoV).

55. The library of any one of embodiments 33-54, wherein the viral entry protein variants are variants of a viral entry protein selected from influenza hemagglutinin (HA), HIV envelope (Env), Chikungunya E1 Env, Chikungunya E2 Env, Ebola glycoprotein (EBOV GP), Hendra F glycoprotein, Hendra G glycoprotein, hepatitis B large (L), hepatitis B middle (M), hepatitis B small (S), hepatitis C glycoprotein E1, hepatitis C glycoprotein E2, Lassa virus envelope glycoprotein (LASV GP), measles hemagglutinin glycoprotein (H), measles fusion glycoprotein F0 (F), MERS-CoV Spike (S), Nipah fusion glycoprotein F0 (F), Nipah glycoprotein G, Rabies virus glycoprotein G (RABV G), RSV fusion glycoprotein F0 (F), RSV glycoprotein G, and SARS-CoV Spike (S).

56. A method of identifying mutations in a viral protein that affect the sensitivity of the virus to a selection pressure using a cell-stored barcoded deep mutational scanning library including storage cells wherein the method includes:
Obtaining the library including storage cells, wherein at least 90% of storage cells include a non-self-inactivating viral vector including a single homozygous barcoded variant nucleotide sequence from a set of homozygous barcoded variant nucleotide sequences in the library integrated into the storage cell's genome, wherein the set of homozygous barcoded variant nucleotide sequences collectively encode viral protein variants including at least 15 amino acid substitutions at at least 95% of amino acid positions of the viral protein;
Transfecting the storage cells with plasmids including sequences encoding viral proteins for production of virions;
Culturing the transfected storage cells to produce virions, wherein each virion includes a homozygous barcoded variant nucleotide sequence encoding a viral protein variant;
Exposing the virions to the selection pressure;
Sequencing barcodes of variant nucleotide sequences from surviving virions; and
Linking sequenced barcodes to encoded viral protein variants to identify mutations in each surviving variant relative to a reference under the selection pressure, thereby identifying mutations in a viral protein that affect the sensitivity of a virus to the selection pressure.

57. The method of embodiment 56, wherein each viral protein variant is expressed.

58. The method of embodiment 56 or 57, wherein the set of homozygous barcoded variant nucleotide sequences collectively encode viral protein variants including at least 17 amino acid substitutions at at least 95% of amino acid positions of the viral protein.

59. The method of any one of embodiments 56-58, wherein the set of homozygous barcoded variant nucleotide sequences collectively encode viral protein variants including at least 19 amino acid substitutions at all amino acid positions of the viral protein.

60. The method of any one of embodiments 56-59, wherein the reference is a counterpart viral protein of a wild-type virus, of a parental virus, or of a baseline clinical isolate.

61. The method of any one of embodiments 56-60, wherein the selection pressure is a therapeutic compound.

62. The method of embodiment 61, further including sequencing the nucleotide sequence of the counterpart viral protein in a subject infected with the virus; comparing the sequenced nucleotide sequence from the subject to variant nucleotide sequences from surviving virions and/or the reference; and predicting whether the therapeutic compound will be an effective therapeutic compound for the subject.

63. The method of embodiment 61 or 62, further including calculating a percentage of viral protein variants that the therapeutic compound is effective against, thereby identifying the percentage of viral entry protein variants of a virus that the therapeutic compound is effective against.

64. The method of any one of embodiments 61-63, further including selecting a therapeutic compound effective against the virus by repeating the exposing, sequencing, linking, and calculating steps for a multitude of therapeutic compounds, thereby selecting a therapeutic compound effective against the virus.

65. The method of any one of embodiments 61-64, wherein the therapeutic compound is undergoing pre-clinical development.
66. The method of any one of embodiments 61-64, wherein the therapeutic compound is undergoing clinical development.
67. The method of any one of embodiments 61-66, wherein the therapeutic compound includes viral entry and/or fusion inhibitors.
68. The method of any one of embodiments 61-67, wherein the therapeutic compound is an antibody, or sera from humans or animals following infection or vaccination.
69. The method of embodiment 68, wherein the antibody is selected from leronlimab (PRO 140), PRO 542, TNX-355 (ibalizumab), human monoclonal IgG1 anti-gp120 antibody b12, polyclonal caprine anti-HIV antibody PEHRG214, anti-HIV antibody PGT121, anti-HIV antibody 3BNC117, anti-RSV G protein monoclonal antibody clone 131-2G, anti-CXCR4 monoclonal antibody clone 12G5 12G5, anti-RSV F protein antibody MAB8582, anti-RSV F protein antibody MAB8581, anti-RSV F protein antibody MCA490, anti-RSV F protein antibody 104E5, anti-RSV F protein antibody 38F10, anti-RSV F protein antibody 14G3, anti-RSV F protein antibody 90D3, anti-RSV F protein antibody 56E11, anti-RSV F protein antibody 69F6, anti-Ebola virus glycoprotein (GP) monoclonal antibody c13C6, anti-Ebola virus glycoprotein (GP) monoclonal antibody c2G4, anti-Ebola virus glycoprotein (GP) monoclonal antibody c4G7, anti-Ebola virus glycoprotein (GP) monoclonal antibody c1H3, LCA60, REGN3051, REGN3048, anti-Lassa virus glycoprotein antibody 37.2D, anti-Lassa virus glycoprotein antibody 8.9F, anti-Lassa virus glycoprotein antibody 19.7E, anti-Lassa virus glycoprotein antibody 37.7H, anti-Lassa virus glycoprotein antibody 12.1F, and Hendra virus neutralizing antibody m102.4.
70. The method of any one of embodiments 61-69, wherein the therapeutic compound includes a small molecule, a protein, a peptide, a polynucleotide, a polysaccharide, an oil, a solution, or a plant extract.
71. The method of any one of embodiments 56-60, wherein the selection pressure is selected from heat, cold, low pH, high pH, and a toxic agent.
72. The method of any one of embodiments 56-60, wherein the selection pressure is the ability of the virus to enter (i) a host cell of a species or (ii) a cell expressing a receptor protein of a species that is different from the species from which the cell was derived, wherein the ability is not dependent on presence of a functional unrelated viral entry protein.
73. The method of embodiment 72, wherein the species is human.
74. The method of embodiment 72 or 73, wherein the host cell is derived from human liver, human lung epithelia, or human lung.
75. The method of any one of embodiments 72-74, wherein the host cell derived from human liver is HuH7, the host cell derived from human lung epithelia is A549 or BEAS-2B, and/or the host cell derived from human lung is Calu-3 or MRC-5.
76. A method of identifying mutations in a viral protein that affect the sensitivity of the virus to a therapeutic compound using a cell-stored barcoded deep mutational scanning library including storage cells wherein the method includes:
Obtaining the library including storage cells, wherein at least 90% of the storage cells include a non-self-inactivating viral vector including a single homozygous barcoded variant nucleotide sequence from a set of homozygous barcoded variant nucleotide sequences in the library integrated into the storage cell's genome, wherein the set of homozygous barcoded variant nucleotide sequences collectively encode viral protein variants including at least 15 amino acid substitutions at at least 95% of amino acid positions of the viral protein;
Transfecting the storage cells with plasmids including sequences encoding viral proteins for production of virions;
Culturing the transfected storage cells to produce virions, wherein each virion includes a homozygous barcoded variant nucleotide sequence encoding a viral protein variant;
Partitioning the produced virions into experimental population groups;
Exposing target cells to (i) different experimental populations groups, and (ii) different concentrations of the therapeutic compound;
Sequencing barcodes of variant nucleotide sequences from surviving virions; and
Linking sequenced barcodes to encoded viral protein variants to identify mutations in each surviving variant relative to a reference exposed to the therapeutic compound, thereby identifying mutations in a viral protein that affect the sensitivity of a virus to the therapeutic compound.
77. The method of embodiment 76, wherein each viral protein variant is expressed.
78. The method of embodiment 76 or 77, wherein the set of homozygous barcoded variant nucleotide sequences collectively encode viral protein variants including at least 17 amino acid substitutions at at least 95% of amino acid positions of the viral protein.
79. The method of any one of embodiments 76-78, wherein the set of homozygous barcoded variant nucleotide sequences collectively encode viral protein variants including at least 19 amino acid substitutions at all amino acid positions of the viral protein.
80. The method of any one of embodiments 76-79, wherein the therapeutic compound is a neutralizing antibody, or sera from humans or animals following infection or vaccination.
81. The method of embodiment 80, further including: calculating the fraction of each surviving virion associated with a particular variant relative to the reference at each antibody concentration; and generating an antibody neutralization curve for each variant nucleotide sequence associated with a surviving virion.
82. The method of any one of embodiments 76-81, wherein the reference is a functional unrelated viral entry protein.
83. The method of embodiment 82, wherein the functional unrelated entry protein is derived from a species selected from vesicular stomatitis virus (Indiana virus), Chandipura virus, rabies virus, Mokola virus, Lymphocytic choriomeningitis virus (LCMV), Ross River virus (RRV), Sindbis virus, Semliki Forest virus (SFV), Venezuelan equine encephalitis virus, Ebola virus Reston, Ebola virus Zaire, Marburg virus, Lassa virus, avian leukosis virus (ALV), Jaagsiekte sheep retrovirus (JSRV), MLV, GALV, RD114, human T-lymphotropic virus 1 (HTLV-1), human foamy virus, Maedi-visna virus (MVV), SARS-CoV, Sendai virus, Respiratory syncytial virus (RSV), human parainfluenza virus type 3, hepatitis C virus (HCV), influenza virus, fowl plague virus (FPV), and *Autographa californica* multiple nucleopolyhedro virus (AcMNPV).

84. The method of embodiment 81, wherein the antibody neutralization curve is visualized as sequence logo plots.
85. The method of any one of embodiments 80-84, wherein barcode counts for a given variant nucleotide sequence greater than barcode counts for the reference at each antibody concentration indicate that a virus including the viral protein encoded by the variant nucleotide sequence is resistant to the neutralization antibody.
86. The method of any one of embodiments 76-85, further including scoring a phenotype as a function of the concentration of the therapeutic compound to obtain an $EC_{50}$ value for each surviving virion associated with a variant viral protein.
87. The method of embodiment 86, further including calculating a ratio of the $EC_{50}$ value for each surviving virion to an $EC_{50}$ value of the reference, wherein the ratio indicates a fold resistance change for each surviving virion associated with a variant viral protein.
88. The method of embodiment 87, further including calculating the fold resistance change for each variant protein to other therapeutic compounds in the same class.
89. The method of any one of embodiments 76-88, wherein the reference is a counterpart viral protein from a wild-type virus, from a parental virus, or from a baseline clinical isolate.
90. The method of any one of embodiments 86-89, wherein the phenotype is virus titer or target cell survival.
91. The method of embodiment 90, wherein the virus titer is calculated from an assay selected from plaque assay and focus-forming assay.
92. The method of embodiment 90, wherein target cell survival is calculated from a colorimetric MTT cytotoxicity assay.
93. The method of any one of embodiments 56-92, wherein the viral vector is a lentiviral vector.
94. The method of any one of embodiments 56-93, wherein the viral vector includes a functional U3.
95. The method of any one of embodiments 56-94, wherein the viral vector includes a gene encoding a reporter or selectable marker.
96. The method of embodiment 95, wherein the gene encoding the reporter or selectable marker is linked to a variant sequence by a linker.
97. The method of embodiment 96, wherein the linker is selected from *Thosea asigna* virus 2A, porcine teschovirus-1 P2A, equine rhinitis A virus E2A, and foot-and-mouth disease virus F2A.
98. The method of any one of embodiments 95-97, wherein the reporter or selectable marker and each viral variant protein are expressed from different promoters.
99. The method of any one of embodiments 56-98, wherein each barcoded variant sequence includes a barcode 4 to 30 nucleotides in length.
100. The method of any one of embodiments 56-99, wherein each barcoded variant nucleotide sequence includes a barcode located after the stop codon of the variant nucleotide sequence.
101. The method of any one of embodiments 56-100, wherein the storage cells are derived from 293T, HEK293T/17, HEK293F, HEK293S, HEK293SGH, EK293FTM, HEK293SGGD, GP2-293, HeLa, HeLa S3, HeLa B, HeLa T4, COS, COS-1, COS-6, COS-M6A, COS-7, A549, MDCK, HepG2, C2C12, THP-1, HUDEP-2, C8161, CCRF-CEM, MOLT, mIMCD-3, NHDF, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, BS-C-1, monkey kidney epithelial, BALB/3T3 mouse embryo fibroblast, 3T3 Swiss, 3T3-L1, 132-d5 human fetal fibroblasts, 10.1 mouse fibroblasts, 3T3, 721, 9L, A2780, A2780ADR, A2780cis, A172, A20, A253, A431, A-549, ALC, B16, B35, BCP-1, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr –/–, COR-L23, COR-L23/CPR, COR-L23/5010, COR-L23/R23, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, Hepa1c1c7, HL-60, HMEC, HT-29, JY, K562, Ku812, KCL22, KG1, KYO1, LNCap, Ma-Mel 1-48, MC-38, MCF-7, MCF-10A, MDA-MB-231, MDA-MB-468, MDA-MB-435, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT2, RenCa, RIN-5F, RMA/RMAS, Saos-2, Sf-9, SkBr3, T2, T-47D, T84, THP1, U373, U87, U937, VCaP, Vero, WM39, WT-49, X63, YAC-1, or YAR cells.
102. The method of any one of embodiments 56-101, wherein the viral protein variants include viral entry protein variants.
103. The method of any one of embodiments 56-101, wherein the viral protein variants include viral Gag Pol variants.
104. The method of any one of embodiments 56-101, wherein the viral protein variants include viral Tat variants.
105. The method of any one of embodiments 56-101, wherein the viral protein variants include viral Rev variants.
106. The method of any one of embodiments 56-105, wherein the viral proteins for production of virions are selected from one or more of Gag Pol, Tat, Rev, and entry protein.
107. The method of any one of embodiments 56-106, wherein the viral proteins for production of virions are expressed in the storage cells.
108. The method of any one of embodiments 102, 106, and 107, wherein the transfecting step further includes transfecting the storage cells with a plasmid including a sequence encoding a functional unrelated viral entry protein to capture non-functional viral entry protein variants.
109. The method of any one of embodiments 102, and 106-108, wherein the viral entry protein variants include variants of a viral entry protein selected from Chikungunya E1 Env, Chikungunya E2 Env, Ebola glycoprotein (EBOV GP), Hendra F glycoprotein, Hendra G glycoprotein, hepatitis B large (L), hepatitis B middle (M), hepatitis B small (S), hepatitis C glycoprotein E1, hepatitis C glycoprotein E2, HIV envelope (Env), influenza hemagglutinin (HA), Lassa virus envelope glycoprotein (LASV GP), measles hemagglutinin glycoprotein (H), measles fusion glycoprotein F0 (F), MERS-CoV Spike (S), Nipah fusion glycoprotein F0 (F), Nipah glycoprotein G, Rabies virus glycoprotein G (RABV G), RSV fusion glycoprotein F0 (F), RSV glycoprotein G, and SARS-CoV Spike (S).

110. The method of any one of embodiments 56-109, wherein the virions from transfected storage cells are non-replicative.
111. The method of any one of embodiments 56-110, wherein the virus is selected from Chikungunya, Ebola, Hendra, hepatitis B, hepatitis C, HIV, influenza, Lassa, measles, MERS-CoV, Nipah, Rabies, RSV, and SARS-CoV.
112. A method of engineering a second, more effective therapeutic antibody from a first antibody against a virus using a cell-stored barcoded deep mutational scanning library including storage cells wherein the method includes:
   Obtaining the library including storage cells, wherein at least 90% of the storage cells include a non-self-inactivating viral vector including a single homozygous barcoded variant nucleotide sequence from a set of homozygous barcoded variant sequences in the library integrated into the storage cell's genome, wherein the set of homozygous barcoded variant nucleotide sequences collectively encode viral protein variants including at least 15 amino acid substitutions at at least 95% of amino acid positions of the viral protein;
   Transfecting the storage cells with plasmids including sequences encoding viral proteins for production of virions;
   Culturing the transfected storage cells to produce virions, wherein each virion includes a homozygous barcoded variant sequence encoding a viral protein variant of the virus;
   Exposing target cells to (i) the produced virions and (ii) the first antibody;
   Sequencing barcodes following exposure to the first antibody, wherein the barcodes associated with variant nucleotide sequences conferring an ability of a virion to evade the first antibody increase in frequency and the barcodes associated with variant nucleotide sequences conferring an inability of a virion to evade the first antibody decrease in frequency;
   Comparing variant nucleotide sequences conferring the ability to evade the first antibody with the nucleotide sequence of a reference viral protein that the first antibody binds;
   Modifying amino acid residues in the first antibody such that the second antibody can neutralize virions that escaped the first antibody based on the comparing and/or on a known structural model of the reference viral protein/first antibody complex, thereby engineering a second, more effective therapeutic antibody from a first antibody against the virus.
113. A method of mapping viral protein mutations of a virus that affect the ability of the virus to infect a host using a cell-stored barcoded deep mutational scanning library including storage cells wherein the method includes:
   Obtaining the library including storage cells, wherein at least 90% of the storage cells include a non-self-inactivating viral vector including a single homozygous barcoded variant sequence from a set of homozygous barcoded variant sequences in the library integrated into the storage cell's genome, wherein the set of homozygous barcoded variant nucleotide sequences collectively encode viral protein variants including at least 15 amino acid substitutions at at least 95% of amino acid positions of the viral protein;
   Transfecting the storage cells with plasmids including sequences encoding viral proteins for production of virions;
   Culturing the transfected storage cells to produce virions, wherein each virion includes a homozygous barcoded variant sequence encoding a viral protein variant of the virus;
   Exposing cells of a target host to the produced virions; and
   Sequencing barcodes of variant nucleotide sequences encoding viral protein variants from surviving cells, thereby mapping viral protein mutations of a virus that affect the ability of the virus to infect a host.
114. The method of embodiment 113, wherein each viral protein variant is expressed.
115. The method of embodiment 113 or 114, wherein the set of homozygous barcoded variant nucleotide sequences collectively encode viral protein variants including at least 17 amino acid substitutions at at least 95% of amino acid positions of the viral protein.
116. The method of any one of embodiments 113-115, wherein the set of homozygous barcoded variant nucleotide sequences collectively encode viral protein variants including at least 19 amino acid substitutions at all amino acid positions of the viral protein.
117. The method of any one of embodiments 113-116, wherein adaptation to a host h of a variant amino acid sequence s is scored as $$S_h(s) = \sum_r \log(\pi_{r,s_r}^h)$$

where $s_r$ is the amino acid at site r of sequence s.
118. The method of any one of embodiments 113-117, wherein the target host is selected from human, bat, camel, rat, and bird.
119. The method of any one of embodiments 113-118, wherein the cells of a target host are from human cell lines.
120. The method of embodiment 119 wherein the human cell lines are derived from human liver, human lung, or human lung epithelia.
121. The method of embodiment 120, wherein the human cell line derived from human liver is HuH7, the human cell line derived from human lung is Calu-3 or MRC-5, and/or the human cell line derived from human lung epithelia is A549 or BEAS-2B.
122. The method of any one of embodiments 113-118, wherein the cells of a target host are from bat cell lines.
123. The method of embodiment 122, wherein the bat cell lines are derived from fruit bat lung, fruit bat kidney, Egyptian fruit bat, or pipestrelle bat.
124. The method of embodiment 123, wherein the bat cell line derived from fruit bat lung is HypLu/45.1, the bat cell line derived from fruit bat kidney is HypNi/1.1, the bat cell line derived from Egyptian fruit bat is RoNi/7, and/or the bat cell line derived from pipestrelle bat is PipNi.
125. The method of any one of embodiments 113-118, wherein the cells of a target host are from a camel cell line.
126. The method of embodiment 125 wherein the camel cell line is derived from a dromedary camel.
127. The method of embodiment 126, wherein the camel cell line derived from a dromedary camel is TT-R.B.
128. The method of any one of embodiments 113-118, wherein the cells of a target host are from a rat cell line.
129. The method of embodiment 128, wherein the rat cell line is derived from rat lung or rat liver.

130. The method of claim 129, wherein the rat cell line derived from rat lung is RLE-6TN and/or wherein the rat cell line derived from rat liver is H-4-II-E.

131. The method of any one of embodiments 113-130, wherein the viral protein variants include viral entry protein variants.

132. The method of any one of embodiments 113-130, wherein the viral protein variants include viral Gag Pol variants.

133. The method of any one of embodiments 113-130, wherein the viral protein variants include viral Tat variants.

134. The method of any one of embodiments 113-130, wherein the viral protein variants include viral Rev variants.

135. The method of any one of embodiments 113-134, wherein the viral proteins for production of virions are selected from one or more of Gag Pol, Tat, Rev, and entry protein.

136. The method of any one of embodiments 113-135, wherein the viral proteins for production of virions are expressed in the storage cells.

137. The method of any one of embodiments 113-131, 135, and 136, wherein the transfecting step further includes transfecting the storage cells with a plasmid including a sequence encoding a functional unrelated entry protein to capture non-functional viral entry protein variants.

138. The method of any one of embodiments 131, and 135-137, wherein the viral entry protein variants include variants of a viral entry protein selected from Chikungunya E1 Env, Chikungunya E2 Env, Ebola glycoprotein (EBOV GP), Hendra F glycoprotein, Hendra G glycoprotein, hepatitis B large (L), hepatitis B middle (M), hepatitis B small (S), hepatitis C glycoprotein E1, hepatitis C glycoprotein E2, HIV envelope (Env), influenza hemagglutinin (HA), Lassa virus envelope glycoprotein (LASV GP), measles hemagglutinin glycoprotein (H), measles fusion glycoprotein F0 (F), MERS-CoV Spike (S), Nipah fusion glycoprotein F0 (F), Nipah glycoprotein G, Rabies virus glycoprotein G (RABV G), RSV fusion glycoprotein F0 (F), RSV glycoprotein G, and SARS-CoV Spike (S).

139. The method of any one of embodiments 113-138, wherein the virions from transfected storage cells are non-replicative.

140. The method of any one of embodiments 113-139, wherein the virus is selected from Chikungunya, Ebola, Hendra, hepatitis B, hepatitis C, HIV, influenza, Lassa, measles, MERS-CoV, Nipah, Rabies, RSV, and SARS-CoV.

141. A kit to generate a cell-stored barcoded viral protein deep mutational scanning library including:
Non-self-inactivating viral vectors for insertion of variant nucleotide sequences encoding viral protein variants;
Expression plasmids including viral proteins for production of virions; and One or more cell lines.

142. The kit of embodiment 141, wherein the viral vectors include retroviral vectors.

143. The kit of embodiment 141 or 142, wherein the viral vectors include lentiviral vectors.

144. The kit of any one of embodiments 141-143, wherein each viral vector includes a unique barcode.

145. The kit of any one of embodiments 141-144, wherein the viral vectors include sequences to facilitate sequencing.

146. The kit of any one of embodiments 141-145, wherein the viral vectors include a gene encoding a reporter or selectable marker.

147. The kit of any one of embodiments 141-146, wherein the viral vectors include a functional U3.

148. The kit of any one of embodiments 141-147, wherein the viral proteins for production of virions are selected from one or more of Gag, Pol, Tat, Rev, and entry protein.

149. The kit of any one of embodiments 141-148, further including a plasmid including an unrelated functional viral entry protein;

150. The kit of embodiment 149, wherein the unrelated functional viral entry protein is VSV-G.

151. The kit of any one of embodiments 141-150, wherein the one or more cell lines is selected from 293T, HEK293T/17, HEK293F, HEK293S, HEK293SGH, EK293FTM, HEK293SGGD, GP2-293, HeLa, HeLa S3, HeLa B, HeLa T4, COS, COS-1, COS-6, COS-M6A, COS-7, A549, MDCK, HepG2, C2C12, THP-1, HUDEP-2, C8161, CCRF-CEM, MOLT, mIMCD-3, NHDF, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, BS-C-1, monkey kidney epithelial, BALB/3T3 mouse embryo fibroblast, 3T3 Swiss, 3T3-L1, 132-d5 human fetal fibroblasts, 10.1 mouse fibroblasts, 3T3, 721, 9L, A2780, A2780ADR, A2780cis, A172, A20, A253, A431, A-549, ALC, B16, B35, BCP-1, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr –/–, COR-L23, COR-L23/CPR, COR-L23/5010, COR-L23/R23, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, Hepa1c1c7, HL-60, HMEC, HT-29, JY, K562, Ku812, KCL22, KG1, KYO1, LNCap, Ma-Mel 1-48, MC-38, MCF-7, MCF-10A, MDA-MB-231, MDA-MB-468, MDA-MB-435, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT2, RenCa, RIN-5F, RMA/RMAS, Saos-2, Sf-9, SkBr3, T2, T-47D, T84, THP1, U373, U87, U937, VCaP, Vero, WM39, WT-49, X63, YAC-1, and YAR cells.

In particular embodiments of each of the Exemplary Embodiments, the 95% percentage can be based on a portion of the protein, for example a portion that excludes areas not of interest to a particular analysis (e.g., a cytoplasmic tail).

In particular embodiments of each of the Exemplary Embodiments, and unless otherwise specified by a particular embodiment (e.g., embodiments 2 and 3), 15 amino acid substitutions at the requisite number of positions is not required. For example, one could select a smaller number of amino acids. In particular embodiments, one could select one or more amino acids from different biochemical classes of amino acids not represented by the native amino acid of the protein (e.g., aliphatic (glycine, alanine, valine, leucine, isoleucine); hydroxyl or sulfur-containing (serine, cysteine, threonine, methionine); cyclic (proline); aromatic (phenylalanine, tyrosine, tryptophan); basic (histidine, lysine, arginine); acidic (aspartate, glutamate, asparagine, glutamine). In particular embodiments, one could select one or more amino acids from each biochemical class of amino acids.

In particular embodiments of each of the Exemplary Embodiments, the variants of the viral protein, along with their barcode, are activatable and packageable into new viruses.

In particular embodiments of each of the Exemplary Embodiments, and unless otherwise specified by a particular embodiment, the libraries can include distinct protein variants that are not deep mutational scanning variants, but instead reflect a collection of different variants of a protein. As just one example, a library could include 200 different Env genes. Such an alternative library can yield valuable information using "neutralization fingerprinting" (i.e. looking at sequence motifs of variants that survive or evade a selection pressure vs those that do not).

In particular embodiments of each of the Exemplary Embodiments that reference a selective process (e.g. a selection pressure (see, e.g., Exemplary Embodiments 56 and 76)), and unless otherwise specified by a particular embodiment, virions can be selected for by the selection pressure (e.g., an antibody or inhibitor) and then the selected for virions can be used to infect cells. In these embodiments, the barcode of virions that survive/escape or evade the selection pressure and infect cells can be sequenced. In particular embodiments, the ability of selected for virions to infect cells is considered a critical component to the identification of escape variants.

When assessing selective pressures, particularly for non-viral entry proteins (e.g., Gag pol, Rev, Tat etc), processes similar to those depicted in FIG. 6 can be used. In particular embodiments, appropriate tweaks to the processes are made. For example, if a drug blocked assembly of Gag, then the drug would be present while generating the virions (not after the virions are generated).

In particular embodiments of each of the Exemplary Embodiments, and unless otherwise specified by a particular embodiment, libraries disclosed herein can be used to select for therapeutic compound (e.g., antibody) binding. Selecting for binding could be done on the cell-stored libraries (assuming the viral entry protein is expressed on the cell surface), and/or on produced virions. In this scenario, one could then sequence the barcode of viruses that do or do not bind the therapeutic compound.

Example 1. Exemplary Methods to Create Codon-Mutant Libraries. The following description of methods to create codon-mutant libraries is adapted from Bloom JD (2014) Mol Biol Evol 31:1956-1978 and directed to the influenza virus nucleoprotein (NP). These methods are provided for illustrative purposes so that one of ordinary skill may adapt these teachings to create codon-mutant libraries for viral entry proteins. The methods described in Bloom involved iterative rounds of low-cycle PCR with pools of mutagenic synthetic oligonucleotides that each contained a randomized NNN triplet at a specific codon site. Two replicate libraries each of the VVT and, in this example, N334H variants of the Aichi/1968 NP were prepared in full biological duplicate, beginning each with independent preps of the plasmid templates pHWAichi68-NP and pHWAichi68-NP-N334H. The sequences of the NP genes in these plasmids are provided in Gong et al. (2013) eLife, 2: e00631. To avoid cross-contamination, all purification steps used an independent gel for each sample, with the relevant equipment thoroughly washed to remove residual DNA.

First, for each codon except for that encoding the initiating methionine in the 498-residue NP gene, an oligonucleotide that contained a randomized NNN nucleotide triplet preceded by the 16 nucleotides upstream of that codon in the NP gene and followed by the 16 nucleotides downstream of that codon in the NP gene were designed. Oligonucleotides can be ordered in a 96-well plate format from, for example, Integrated DNA Technologies. They can be combined in equimolar quantities to create the forward-mutagenesis primer pool. The reverse complement of each of these oligonucleotides can also be designed and ordered and combined in equimolar quantities to create the reverse-mutagenesis pool. The primers for the N334H variants differed only for those that overlapped the N334H codon. End primers that anneal to the termini of the NP sequence and contain sites appropriate for BsmBI cloning into the influenza reverse-genetics plasmid pHW2000 (Hoffmann, et al. (2000) Proc Natl Acad Sci USA, 97: 6108-6113) can also be designed. These primers were 5'-BsmBI-Aichi68-NP (catgatcgtctcagggagcaaaagcagggtagataatcactcacag (SEQ ID NO: 57)) and 3'-BsmBI-Aichi68-NP (catgatcgtctcgtatt-agtagaaacaagggtattttctta (SEQ ID NO: 58)).

PCR reactions were conducted that contained 1 µl of 10 ng/µl template pHWAichi68-NP plasmid (Gong, et al. (2013) eLife, 2: e00631), 25 µl of 2×KOD Hot Start Master Mix (product number 71842, EMD Millipore), 1.5 µl each of 10 µM solutions of the end primers 5'-BsmBI-Aichi68-NP and 3'-BsmBI-Aichi68-NP, and 21 µl of water. The following PCR program was used (referred to as the amplicon PCR program in the remainder of this article): The PCR products were purified over agarose gels using ZymoClean columns (product number D4002, Zymo Research) and used as templates for the initial codon mutagenesis fragment PCR.
1. 95° C. for 2 min.
2. 95° C. for 20 s.
3. 70° C. for 1 s.
4. 50° C. for 30 s cooling to 50° C. at 0.5° C./s.
5. 70° C. for 40 s.
6. Repeat steps 2 through 5 for 24 additional cycles.
7. Hold 4° C.

Two fragment PCR reactions were run for each template. The forward-fragment reactions contained 15 µl of 2×KOD Hot Start Master Mix, 2 µl of the forward mutagenesis primer pool at a total oligonucleotide concentration of 4.5 µM, 2 µl of 4.5 µM 3'-BsmBI-Aichi68-NP, 4 µl of 3 ng/µl of the aforementioned gel-purified linear PCR product template, and 7 µl of water. The reverse-fragment reactions were identical except that the reverse mutagenesis pool was substituted for the forward mutagenesis pool and that 5'-BsmBI-Aichi68-NP was substituted for 3'-BsmBI-Aichi68-NP. The PCR program for these fragment reactions was identical to the amplicon PCR program except that it utilized a total of 7 rather than 25 thermal cycles.

The products from the fragment PCR reactions were diluted 1:4 in water. These dilutions were then used for the joining PCR reactions, which contained 15 µl of 2×KOD Hot Start Master Mix, 4 µl of the 1:4 dilution of the forward-fragment reaction, 4 µl of the 1:4 dilution of the reverse-fragment reaction, 2 µl of 4.5 µM 5'-BsmBI-Aichi68-NP, 2 µl of 4.5 µM 3'-BsmBI-Aichi68-NP, and 3 µl of water. The PCR program for these joining reactions was identical to the amplicon PCR program except that it utilized a total of 20 rather than 25 thermal cycles. The products from these joining PCRs were purified over agarose gels.

The purified products of the first joining PCR reactions were used as templates for a second round of fragment reactions followed by joining PCRs. These second-round products were used as templates for a third round. The third-round products were purified over agarose gels, digested with BsmBI (product number R0580L, New England Biolabs), and ligated into a dephosphorylated (Antarctic Phosphatase, product number M0289L, New England Biolabs) BsmBI digest of pHW2000 (Hoffmann et al. 2000) using T4 DNA ligase. The ligations were purified using ZymoClean columns, electroporated into ElectroMAX DH10B T1 phage-resistant competent cells (product number 12033-015, Invitrogen), and plated on LB plates supplemented with 100 µg/ml of ampicillin. These transformations yielded between 400,000 and 800,000 unique transformants per plate, as judged by plating a 1:4,000 dilution of the transformations on a second set of plates. Transformation of a parallel no-insert control ligation yielded 50-fold fewer colonies, indicating that self ligation of pHW2000 only accounts for a small fraction of the transformants. For each library, three transformations were performed, the plates were grown overnight, and then the colonies were scraped into liquid LB supplemented with ampicillin and mini-prepped several hours later to yield the plasmid mutant libraries. These libraries each contained in excess of $10^6$ unique transformants, most of which will be unique codon mutants of the NP gene.

The NP gene was sequenced for 30 individual clones drawn from the four mutant libraries. The number of mutations per clone was Poisson distributed and the mutations occurred uniformly along the primary sequence. If all codon mutations are made with equal probability, 9/63 of the mutations should be single-nucleotide changes, 27/63 should be two-nucleotide changes, and 27/63 should be three-nucleotide changes. This is what was observed in the Sanger-sequenced clones. The nucleotide composition of the mutated codons was roughly uniform, and there was no tendency for clustering of multiple mutations in primary sequence. The results of this Sanger sequencing are compatible with the mutation frequencies obtained from deep sequencing the "mutDNA" samples after subtracting off the sequencing error rate estimated from the DNA samples, especially considering that the statistics from the Sanger sequencing are subject to sampling error due to the limited number of clones analyzed.

Example 2. Producing lentiviruses pseudotyped with diverse viral entry proteins. Viral entry proteins from different viruses (vesicular stomatitis virus G glycoprotein (VSV G); Ebola virus glycoprotein (EBOV GP); rabies virus glycoprotein (RABV G); and Lassa virus glycoprotein (LASV GP)) were cloned into a repaired U3 lentiviral backbone vector. FIG. 12 shows the viral titer of lentiviruses when each construct was transfected into 293T cells alongside lentiviral helper plasmids (expressing Gag/Pol, Tat, and Rev) (squares) or when each construct and lentiviral helper plasmids were transfected along with a construct containing VSV G (circles), such that the lentivirus is pseudotyped with both the viral entry protein of interest and VSV G. These data show that lentiviruses pseudotyped with diverse viral entry proteins can be expressed from the lentiviral backbone, and that additional pseudotyping of VSV G does not adversely affect these titers, showing that producing lentiviruses pseudotyped with diverse viral entry proteins can be done. Titer in transduction units (TU) was determined using flow cytometry to measure GFP expression in 293T cells, which express the relevant receptors for these viruses (VSV G: LDL receptor; EBOV GP: NPC1; RABV G: Endocytosis mediated cell entry; LASV: alpha-dystroglycan).

Figure 13:
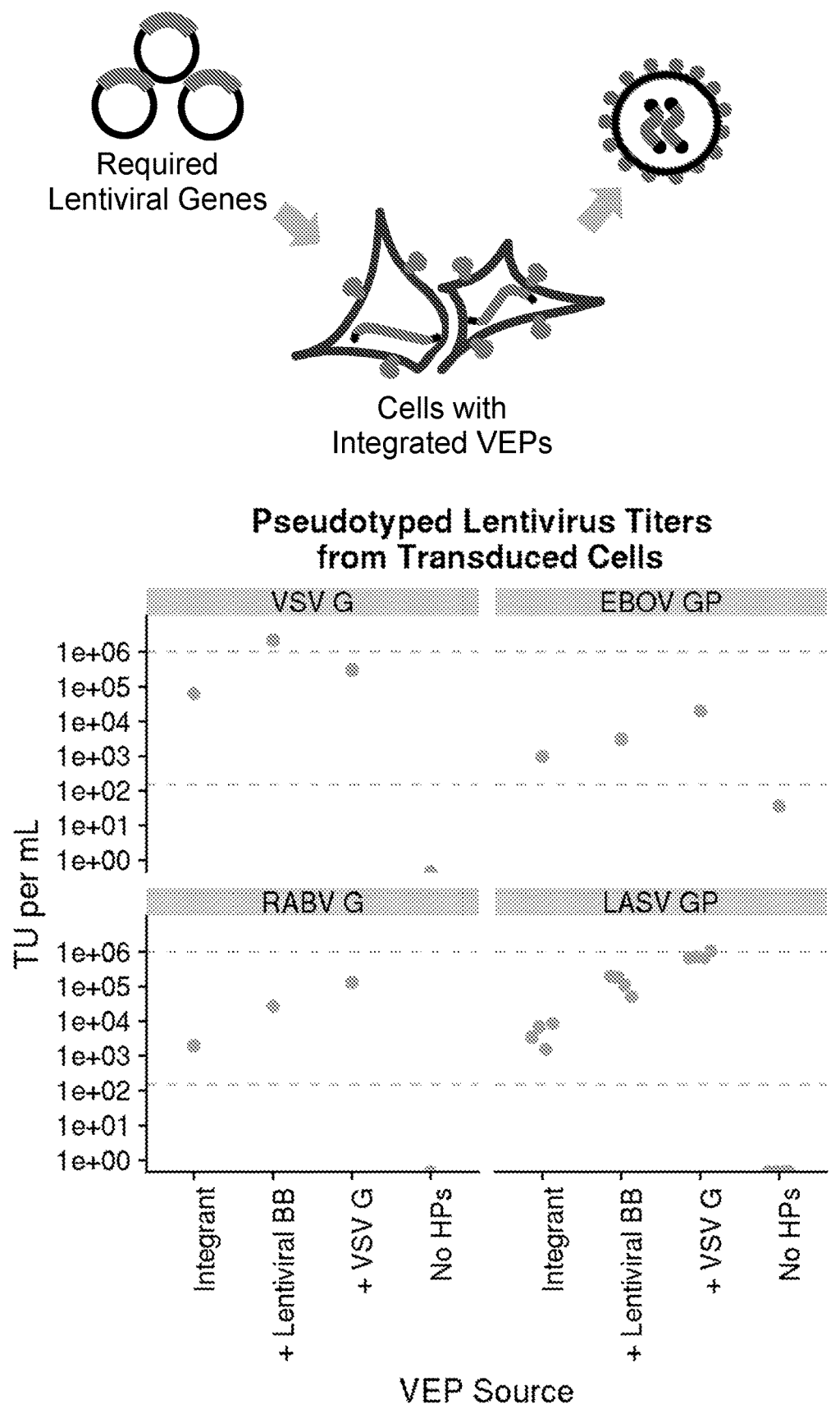

Example 3. Recovery of lentiviruses bearing diverse viral entry proteins from transduced cells. Lentiviral helper plasmids (expressing Gag/Pol, Tat, and Rev, without VSV G or other viral entry protein) were transfected into a cell line containing integrated non-self-inactivating lentiviral vector encoding a viral entry protein to produce virions having homozygous barcoded nucleotide sequences encoding the viral entry protein. FIG. 13 shows the titers of pseudotyped lentiviruses, in which the viral entry protein comes from an integrated viral entry protein gene (the "Integrant" condition). Additionally, transfecting in the lentiviral backbone (the "+lentiviral BB" condition) boosts titers, but virus is able to be recovered without this additional control. The "+VSV G" condition shows the lentiviral titer when also transfecting in VSV G protein expression plasmid, serving as an additional positive control. When no helper plasmids ("no HPs" condition) are transfected, no lentivirus is produced from the integrated cell line. This shows that lentiviruses bearing diverse viral entry proteins can be recovered from cell lines transduced with non-self-inactivating lentiviral vectors encoding viral entry proteins of interest.

Figure 14A:
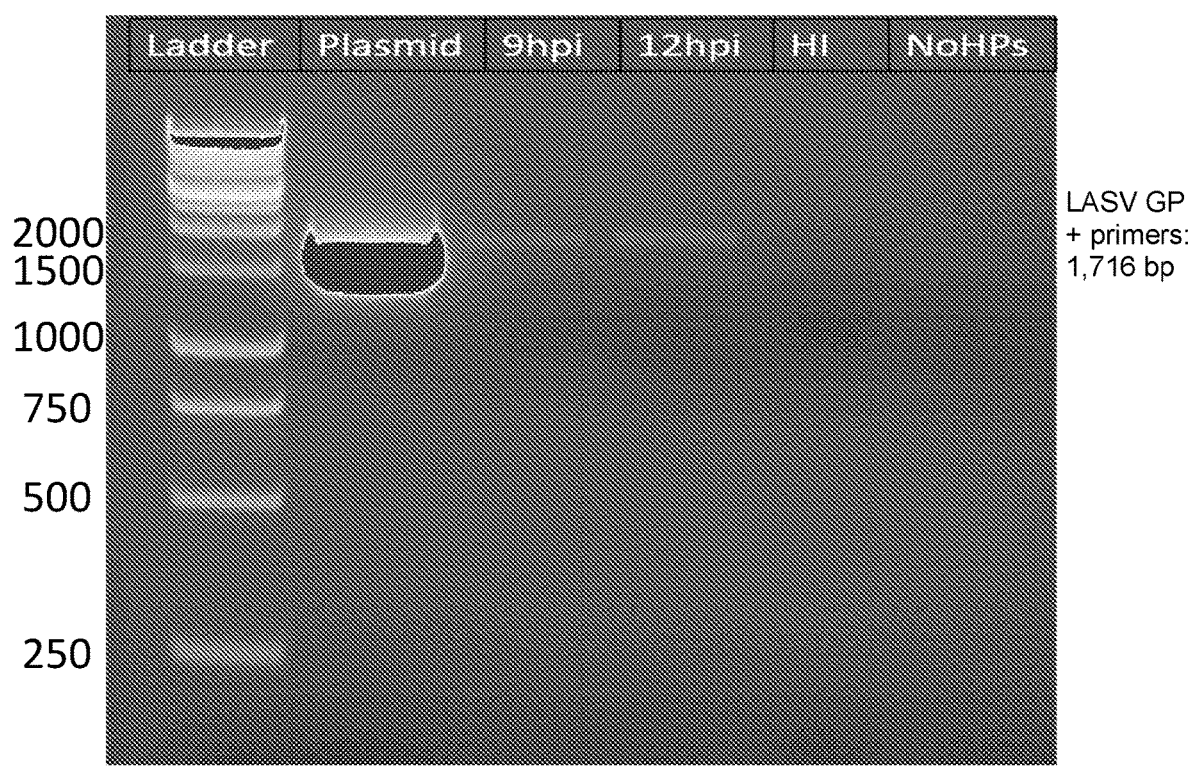

Example 4. Lentiviral backbones encoding viral entry proteins of interest can be sequenced from infected cells. Non-integrated viral DNA was harvested from cells infected with lentiviruses packaging a backbone encoding LASV GP at 9 hours post-infection (hpi) and 12 hpi. FIG. 14A shows that full-length LASV GP gene can be clearly and cleanly amplified from these samples. The plasmid lane started with significantly more DNA and is clearly saturated. As expected, lentiviral constructs cannot be amplified from cells infected with heat-inactivated (HI) virus or with a negative control supernatant (NoHPs—no helper plasmids). FIG. 14B shows that lentiviral constructs can be successfully harvested from cells infected with lentivirus pseudotyped with and packaging the gene encoding a viral entry protein of a virus for many viruses. Cells infected with lentiviruses made with the constructs indicated in FIG. 14B have $2^{10}$ to $2^5$ more copies of DNA than the negative control background heat inactivated sample. This results in sufficient DNA for downstream sequencing experiments. These data show that packaged lentiviral genomes produced from transduced cells can be successfully amplified after they enter target cells.

Example 5. Antibody selection of a cell-stored barcoded deep mutational scanning library of a viral entry protein. Antibody selection can assess the ability of different viral entry proteins to evade antibody neutralization. Virions produced from the library and carrying homozygous barcoded nucleotide sequences encoding variants of a viral entry protein can be incubated with an antibody that targets the virus. Target cells can then be infected again with the treated virions. Virions not treated with antibody can serve as a replicate-specific control to calculate differential selection. For each condition, $10^6$ infectious units of the library can be incubated ±1 µg/mL of antibody at 37° C. for 1 hr, then infected into $10^6$ (not antibody treated) or $2 \times 10^5$ (antibody treated) target cells in the presence of 100 µg/mL DEAE-dextran. The antibody concentration can be chosen with the goal of inhibiting 97.5% of the viral infectivity. Three hours post infection, cells can be spun down and resuspended in fresh media, containing no DEAE-dextran. At 12 hr post infection, cells can be spun down, washed with phosphate-buffered saline (PBS), and then subjected to a mini-prep to harvest non-integrated viral cDNA. Non-neutralized wild-type virus can be infected in parallel.

Example 6. Deep sequencing and data analysis. Deep sequencing can be used to determine the frequency of each mutation in the antibody-selected and non-selected conditions. A high throughput sequencing method that can sequence long reads with high accuracy, such as circular consensus Pac-Bio sequencing (Travers, et al. (2010) Nucleic Acids Research 38: e159-e159; and Laird Smith, et al. (2016) Virus Evolution 2: vew018), can be used to associate each entry protein variant with its barcode. Amplification of barcode-linked genes can be via emulsion PCR to allow clonal amplification of templates from complex mixtures in a bias-free manner. Schütze et al. (2011) Analytical Biochemistry 410: 155-157. Briefly, the PCR mixture can be combined with an oil surfactant and an emulsion is formed by vigorous vortexing. After PCR, the emulsion can be broken with isobutanol, and binding buffer from a DNA cleanup kit can be added. Centrifugation can be performed to separate organic and aqueous phases, the organic phase can be removed, and DNA in the aqueous phase can be purified using a DNA cleanup kit.

Single Molecule Real Time (SMRT)bell template libraries of barcoded viral entry protein genes can be prepared according to the manufacturer's instructions using the SMRTbell Template Prep Kit 1.0 (part no. 100-259-100; Pacific Biosciences, Menlo Park, CA). A total of 250 ng of AMPure PB bead-purified amplicon can be added directly into the DNA damage repair step of the 10-kb Template Preparation and Sequencing (with low-input DNA) protocol. Library quality and quantity can be assessed using the Agilent 12000 DNA Kit and the 2100 Bioanalyzer System (Santa Clara, CA, USA), as well as the Qubit dsDNA BR Assay kit and Qubit Fluorometer (Thermo Fisher, Waltham, MA). Sequencing primer annealing can be performed using the recommended 20:1 primer:template ratio, whereas P5 polymerase binding can be performed at a modified polymerase:template ratio of 3:1. Barcoded viral entry protein gene SMRTbell libraries can be immobilized onto SMRT cells at a starting concentration of 10 µM on chip. Loading titrations can be performed to achieve optimal sequencing conditions for particular samples as necessary. SMRT sequencing can be performed on the PacBio RS II using the C3 sequencing kit with magnetic bead loading and 180-minute movies. Circular consensus sequencing (CCS) reads can be generated using Quiver (Chin et al. (2013) Nature Methods. 10: 563-569) and the Reads of Insert (Larsen et al. (2014) BMC Genomics. 15: 720) protocol as a part of SMRT analysis version 2.3, and .fastq files can be used for downstream analysis.

Once each entry protein variant is associated with its barcode, only barcodes need to be sequenced to determine the frequency of each mutation. Sequencing of barcodes can be performed by an Illumina deep sequencing approach as previously described (Doud and Bloom, 2016; Haddox et al., 2016). KOD Hot Start Master Mix (71842, EMD Millipore, Burlington, MA) can be used for each PCR reaction. PCR products can be cleaned with Agencourt AMPure XP beads (A63880, Beckman Coulter, Brea, CA) using a bead-to-sample ratio of 1.0 and quantified via Quant-iT PicoGreen dsDNA Assay Kit (P7589, Life Technologies). 20 µL PCR reaction can be performed to add the remainder of the Illumina sequencing adapters. The PCR reaction conditions can include:
1. 95° C., 2 min
2. 95° C., 20 s
3. 70° C., 1 s
4. 60° C., 10 s
5. 70° C., 10 s
6. Go to 2, repeat 23 times
7. Hold at 4° C.

Finally, samples can be pooled, purified by gel electrophoresis, and sequenced on an Illumina HiSeq or MiSeq using 2×250 bp paired-end reads.

dms_tools on the World Wide Web at jbloomlab.github.io/dms_tools/, version 1.1.dev13, can be used to filter and align the deep-sequencing reads, count the number of times each codon mutation was observed both before and after selection, and infer the viral entry protein's site-specific amino-acid preferences using the algorithm described in Bloom et al. BMC bioinformatics. 2015; 16:168.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability to detect viral entry protein susceptibility to a selection pressure, such as ability to evade a therapeutic treatment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A cell-stored barcoded deep mutational scanning library of variants of a viral protein comprising: storage cells, wherein at least 90% of the storage cells comprise a non-self-inactivating viral vector comprising a single homozygous barcoded variant nucleotide sequence encoding a viral protein variant from a set of homozygous barcoded variant nucleotide sequences in the library integrated into the storage cell's genome, wherein the set of homozygous barcoded variant nucleotide sequences collectively encode viral protein variants comprising at least 15 amino acid substitutions at at least 95% of amino acid positions of the viral protein.

2. The library of claim 1, wherein the viral protein variants comprise viral entry protein variants.

3. The library of claim 1, wherein the viral protein variants comprise viral gag pol variants.

4. The library of claim 1, wherein the viral protein variants comprise viral Tat variants.

5. The library of claim 1, wherein the viral protein variants comprise viral Rev variants.

6. The library of claim 1, wherein the viral vector comprises a retroviral vector or a lentiviral vector.

7. The library of claim 1, wherein the viral vector comprises a functional U3.

8. The library of claim 1, wherein the viral vector comprises a gene encoding a reporter or selectable marker.

9. The library of claim 8, wherein the gene encoding the reporter or selectable marker is linked to each barcoded variant sequence by a linker.

10. The library of claim 9, wherein the linker is selected from *Thosea asigna* virus 2A, porcine teschovirus-1 P2A, equine rhinitis A virus E2A, and foot-and-mouth disease virus F2A.

11. The library of claim 1, wherein the viral vector comprises a first promoter to express the reporter or selectable marker and a second promoter to express the viral variant protein.

12. The library of claim 1, wherein each barcoded variant sequence comprises a barcode located after the stop codon of the variant sequence.

13. The library of claim 1, wherein the storage cells are derived from 293T, HEK293T/17, HEK293F, HEK293S, HEK293SGH, EK293FTM, HEK293SGGD, GP2-293, HeLa, HeLa S3, HeLa B, HeLa T4, COS, COS-1, COS-6, COS-M6A, COS-7, A549, MDCK, HepG2, C2C12, THP-1, HUDEP-2, C8161, CCRF-CEM, MOLT, mIMCD-3, NHDF, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, BS-C-1, monkey kidney epithelial, BALB/3T3 mouse embryo fibroblast, 3T3 Swiss, 3T3-L1, 132-d5 human fetal fibroblasts, 10.1 mouse fibroblasts, 3T3, 721, 9L, A2780, A2780ADR, A2780cis, A172, A20, A253, A431, A-549, ALC, B16, B35, BCP-1, BEAS-2B, bEnd.3, BHK-21, BR 293, BxPC3, C3H-10T1/2, C6/36, Cal-27, CHO, CHO-7, CHO—IR, CHO-K1, CHO-K2, CHO-T, CHO Dhfr-/-, COR-L23, COR-L23/CPR, COR-L23/5010, COR-L23/R23, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, Hepa1c1c7, HL-60, HMEC, HT-29, JY, K562, Ku812, KCL22, KG1, KYO1, LNCap, Ma-Mel 1-48, MC-38, MCF-7, MCF-10A, MDA-MB-231, MDA-MB-468, MDA-MB-435, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT2, RenCa, RIN-5F, RMA/RMAS, Saos-2, Sf-9, SkBr3, T2, T-47D, T84, THP1, U373, U87, U937, VCaP, Vero, WM39, WT-49, X63, YAC-1, and YAR cells.

14. The library of claim 2, wherein the storage cells further comprise plasmids comprising sequences encoding viral Gag Pol, Tat, and Rev proteins.

15. The library of claim 2, wherein the storage cells further comprise a plasmid comprising a sequence encoding a functional unrelated viral entry protein.

16. The library of claim 3, wherein the storage cells further comprise plasmids comprising sequences encoding Tat, Rev, and an entry protein.

17. The library of claim 4, wherein the storage cells further comprise plasmids comprising sequences encoding an entry protein, Gag Pol, and Rev.

18. The library of claim 5, wherein the storage cells further comprise plasmids comprising sequences encoding an entry protein, Gag Pol, and Tat.

19. The library of claim 1, wherein the viral protein is derived from a virus selected from Chikungunya, Ebola, Hendra, hepatitis B, hepatitis C, human immunodeficiency virus (HIV), simian immunodeficiency virus (SIV), influenza, Lassa, measles, Middle East respiratory syndrome coronavirus (MERS-COV), Nipah, Rabies, respiratory syncytial virus (RSV), and severe acute respiratory syndrome coronavirus (SARS-COV).

20. The library of claim 2, wherein the viral entry protein variants are variants of a viral entry protein selected from influenza hemagglutinin (HA), HIV envelope (Env), Chikungunya E1 Env, Chikungunya E2 Env, Ebola glycoprotein (EBOV GP), Hendra F glycoprotein, Hendra G glycoprotein, hepatitis B large (L), hepatitis B middle (M), hepatitis B small(S), hepatitis C glycoprotein E1, hepatitis C glycoprotein E2, Lassa virus envelope glycoprotein (LASV GP), measles hemagglutinin glycoprotein (H), measles fusion glycoprotein F0 (F), MERS-COV Spike(S), Nipah fusion glycoprotein F0 (F), Nipah glycoprotein G, Rabies virus glycoprotein G (RABV G), RSV fusion glycoprotein F0 (F), RSV glycoprotein G, and SARS-COV Spike(S).

* * * * *

SEQUENCE LISTING

```
<160> NUMBER OF SEQ ID NOS: 58

<210> SEQ ID NO 1
<211> LENGTH: 63
<212> TYPE: DNA
<213> ORGANISM: artificial sequence
<220> FEATURE:
<223> OTHER INFORMATION: thosea asigna virus T2A

<400> SEQUENCE: 1
ggcagcggcg aaggccgcgg cagcctgctg acctgcggcg atgtggaaga aaacccgggc    60
ccg                                                                  63

<210> SEQ ID NO 2
<211> LENGTH: 66
<212> TYPE: DNA
<213> ORGANISM: artificial sequence
<220> FEATURE:
<223> OTHER INFORMATION: porcine teschovirus-1 P2A

<400> SEQUENCE: 2
ggcagcggcg cgaccaactt tagcctgctg aaacaggcgg gcgatgtgga agaaaacccg    60
ggcccg                                                               66

<210> SEQ ID NO 3
```

```
<211> LENGTH: 69
<212> TYPE: DNA
<213> ORGANISM: artificial sequence
<220> FEATURE:
<223> OTHER INFORMATION: equine rhinitis A virus E2A

<400> SEQUENCE: 3
ggcagcggcc agtgcaccaa ctatgcgctg ctgaaactgg cgggcgatgt ggaaagcaac      60
ccgggcccg                                                             69

<210> SEQ ID NO 4
<211> LENGTH: 75
<212> TYPE: DNA
<213> ORGANISM: artificial sequence
<220> FEATURE:
<223> OTHER INFORMATION: foot-and-mouth disease virus F2A

<400> SEQUENCE: 4
ggcagcggcg tgaaacagac cctgaacttt gatctgctga aactggcggg cgatgtggaa      60 agcaaccccgg gcccg                                                      75

<210> SEQ ID NO 5
<211> LENGTH: 90
<212> TYPE: DNA
<213> ORGANISM: artificial sequence
<220> FEATURE:
<223> OTHER INFORMATION: equine rhinitis B virus 12A

<400> SEQUENCE: 5
gaagcaactt tgtctaccat tctgtctgag ggtgccacaa attttctctt gttgaagtta      60 gcagggatg ttgaacttaa ccccggccca                                        90

<210> SEQ ID NO 6
<211> LENGTH: 90
<212> TYPE: DNA
<213> ORGANISM: artificial sequence
<220> FEATURE:
<223> OTHER INFORMATION: Saffold virus 2A

<400> SEQUENCE: 6
ttcactgatt ttttcaaagc cgttagagac tatcatgctt cttattacaa acagagactt      60
caacatgacg ttgaaacaaa ccctggccct                                       90

<210> SEQ ID NO 7
<211> LENGTH: 90
<212> TYPE: DNA
<213> ORGANISM: artificial sequence
<220> FEATURE:
<223> OTHER INFORMATION: Ljungan virus 2A

<400> SEQUENCE: 7
tactttaata taatgcacag tgatgaaatg gattttgccg gggggaaatt tttgaatcaa      60
tgtggtgatg tggaaactaa cccaggccct                                       90

<210> SEQ ID NO 8
<211> LENGTH: 90
<212> TYPE: DNA
<213> ORGANISM: artificial sequence
<220> FEATURE:
<223> OTHER INFORMATION: infectious flacherie virus 2A

<400> SEQUENCE: 8
ccctcaattg gtaatgtcgc gcggactctg acgagggcgg agattgagga tgaattgatt      60
```
cgtgcaggaa ttgaatcaaa tcctggacct                                              90

<210> SEQ ID NO 9
<211> LENGTH: 90
<212> TYPE: DNA
<213> ORGANISM: artificial sequence
<220> FEATURE:
<223> OTHER INFORMATION: Perina nuda picorna-like virus 2A1

<400> SEQUENCE: 9
ggacaaagga cgactgaaca gatagttacg gcccaggggt gggttccgga tttgactgtg       60
gatggagatg ttgagtcaaa tcccggaccc                                        90

<210> SEQ ID NO 10
<211> LENGTH: 90
<212> TYPE: DNA
<213> ORGANISM: artificial sequence
<220> FEATURE:
<223> OTHER INFORMATION: Perina nuda picorna-like virus 2A2

<400> SEQUENCE: 10
acgcgtggtg gtttacgacg gcaaaatatt attggtggtg ggcagaagga tttgacacaa       60
gatggtgaca tcgagtcgaa tcctgggccc                                        90

<210> SEQ ID NO 11
<211> LENGTH: 90
<212> TYPE: DNA
<213> ORGANISM: artificial sequence
<220> FEATURE:
<223> OTHER INFORMATION: Ectropis obliqua picorna-like virus 2A1

<400> SEQUENCE: 11
ggacaacgga caactgagca gatcgtgact gcacaaggtt gggccccgga tttgacacag       60
gatggagatg tagagtcaaa ccccggcccc                                        90

<210> SEQ ID NO 12
<211> LENGTH: 90
<212> TYPE: DNA
<213> ORGANISM: artificial sequence
<220> FEATURE:
<223> OTHER INFORMATION: Ectropis obliqua picorna-like virus 2A2

<400> SEQUENCE: 12
acacgtggtg gtttacagcg tcaaaacatt attggtggtg gccaaaggga tctgactcaa       60
gatggcgaca tcgagtcgaa ccccggccca                                        90

<210> SEQ ID NO 13
<211> LENGTH: 90
<212> TYPE: DNA
<213> ORGANISM: artificial sequence
<220> FEATURE:
<223> OTHER INFORMATION: Drosophila C virus 2A

<400> SEQUENCE: 13
caaggcatcg gtaagaagaa tccgaaacag gaagctgcac gtcagatgtt gctcttgtta       60
tcaggagatg ttgagactaa ccctggaccc                                        90

<210> SEQ ID NO 14
<211> LENGTH: 90
<212> TYPE: DNA
<213> ORGANISM: artificial sequence
<220> FEATURE:

<223> OTHER INFORMATION: acute bee paralysis virus 2A

<400> SEQUENCE: 14 actggtttttt taaacaagtt atatcattgt ggctcatgga ctgacatatt gttgttgttg    60
tctggagatg tagaaaccaa tccaggacct                                      90

<210> SEQ ID NO 15
<211> LENGTH: 90
<212> TYPE: DNA
<213> ORGANISM: artificial sequence
<220> FEATURE:
<223> OTHER INFORMATION: Euprosterna elaeasa virus 2A

<400> SEQUENCE: 15
cgacgattgc cggagtccgc ccagctcccc caagggggcgg ggcgcggaag tctggtaaca    60
tgtggcgacg tggaggagaa tccagggccc                                      90

<210> SEQ ID NO 16
<211> LENGTH: 90
<212> TYPE: DNA
<213> ORGANISM: artificial sequence
<220> FEATURE:
<223> OTHER INFORMATION: Providence virus 2A1

<400> SEQUENCE: 16
ttggagatga aggagtctaa tagtggttac gtagtcggtg accgggggtc tcttctcact    60
tgtggggacg ttgaatccaa ccctggaccc                                      90

<210> SEQ ID NO 17
<211> LENGTH: 90
<212> TYPE: DNA
<213> ORGANISM: artificial sequence
<220> FEATURE:
<223> OTHER INFORMATION: Providence virus 2A3

<400> SEQUENCE: 17
acgcttatgg ggaacatcat gacacttgca gggtcaggtg gtcggggaag cttgctgacc    60
gcaggcgatg ttgaaaagaa ccctgggccc                                      90

<210> SEQ ID NO 18
<211> LENGTH: 95
<212> TYPE: DNA
<213> ORGANISM: artificial sequence
<220> FEATURE:
<223> OTHER INFORMATION: Bombyx mori cypovirus-1 2A

<400> SEQUENCE: 18
agaacagcgt tcgatttcca gcaggacgtt tttcgctcta attatgacct actaaagttg    60
tgcggtgata tcgagtctaa tcctggacct gttac                                95

<210> SEQ ID NO 19
<211> LENGTH: 90
<212> TYPE: DNA
<213> ORGANISM: artificial sequence
<220> FEATURE:
<223> OTHER INFORMATION: Operophtera brumata cypovirus-18 2A

<400> SEQUENCE: 19
atccatgcta atgattatca gatggctgtg tttaaatcaa attatgattt gctgaagtta    60 tgcgggggacg tggaatcaaa tcctggccct                                     90

<210> SEQ ID NO 20
<211> LENGTH: 90
<212> TYPE: DNA
<213> ORGANISM: artificial sequence
<220> FEATURE:
<223> OTHER INFORMATION: new adult diarrhea virus 2A

<400> SEQUENCE: 20
ttcttcgatt cggtttgggt gtaccacttg gcaaacagct cttgggttcg agatttaact    60
agagaatgca ttgaatctaa ccctggacca                                     90

<210> SEQ ID NO 21
<211> LENGTH: 21
<212> TYPE: PRT
<213> ORGANISM: artificial sequence
<220> FEATURE:
<223> OTHER INFORMATION: thosea asigna virus T2A

<400> SEQUENCE: 21

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 22
<211> LENGTH: 22
<212> TYPE: PRT
<213> ORGANISM: artificial sequence
<220> FEATURE:
<223> OTHER INFORMATION: porcine teschovirus-1 P2A

<400> SEQUENCE: 22

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 23
<211> LENGTH: 23
<212> TYPE: PRT
<213> ORGANISM: artificial sequence
<220> FEATURE:
<223> OTHER INFORMATION: equine rhinitis A virus E2A

<400> SEQUENCE: 23

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 24
<211> LENGTH: 25
<212> TYPE: PRT
<213> ORGANISM: artificial sequence
<220> FEATURE:
<223> OTHER INFORMATION: foot-and-mouth disease virus F2A

<400> SEQUENCE: 24

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 25

```
<211> LENGTH: 30
<212> TYPE: PRT
<213> ORGANISM: artificial sequence
<220> FEATURE:
<223> OTHER INFORMATION: equine rhinitis B virus 12A

<400> SEQUENCE: 25

Glu Ala Thr Leu Ser Thr Ile Leu Ser Gly Ala Thr Asn Phe Ser
1               5                   10                  15
Leu Leu Lys Leu Ala Gly Asp Val Glu Leu Asn Pro Gly Pro
            20                  25                  30

<210> SEQ ID NO 26
<211> LENGTH: 30
<212> TYPE: PRT
<213> ORGANISM: artificial sequence
<220> FEATURE:
<223> OTHER INFORMATION: Saffold virus 2A

<400> SEQUENCE: 26

Phe Thr Asp Phe Phe Lys Ala Val Arg Asp Tyr His Ala Ser Tyr Tyr
1               5                   10                  15
Lys Gln Arg Leu Gln His Asp Val Glu Thr Asn Pro Gly Pro
            20                  25                  30

<210> SEQ ID NO 27
<211> LENGTH: 30
<212> TYPE: PRT
<213> ORGANISM: artificial sequence
<220> FEATURE:
<223> OTHER INFORMATION: Ljungan virus 2A

<400> SEQUENCE: 27

Tyr Phe Asn Ile Met His Ser Asp Glu Met Asp Phe Ala Gly Gly Lys
1               5                   10                  15
Phe Leu Asn Gln Cys Gly Asp Val Glu Thr Asn Pro Gly Pro
            20                  25                  30

<210> SEQ ID NO 28
<211> LENGTH: 30
<212> TYPE: PRT
<213> ORGANISM: artificial sequence
<220> FEATURE:
<223> OTHER INFORMATION: infectious flacherie virus 2A

<400> SEQUENCE: 28

Pro Ser Ile Gly Asn Val Ala Arg Thr Leu Thr Arg Ala Glu Ile Glu
1               5                   10                  15
Asp Glu Leu Ile Arg Ala Gly Ile Glu Ser Asn Pro Gly Pro
            20                  25                  30

<210> SEQ ID NO 29
<211> LENGTH: 30
<212> TYPE: PRT
<213> ORGANISM: artificial sequence
<220> FEATURE:
<223> OTHER INFORMATION: Perina nuda picorna-like virus 2A1

<400> SEQUENCE: 29

Gly Gln Arg Thr Thr Glu Gln Ile Val Thr Ala Gln Gly Trp Val Pro
1               5                   10                  15
Asp Leu Thr Val Asp Gly Asp Val Glu Ser Asn Pro Gly Pro
            20                  25                  30
```

```
<210> SEQ ID NO 30
<211> LENGTH: 30
<212> TYPE: PRT
<213> ORGANISM: artificial sequence
<220> FEATURE:
<223> OTHER INFORMATION: Perina nuda picorna-like virus 2A2

<400> SEQUENCE: 30

Thr Arg Gly Gly Leu Arg Arg Gln Asn Ile Ile Gly Gly Gln Lys
1               5                   10                  15

Asp Leu Thr Gln Asp Gly Asp Ile Glu Ser Asn Pro Gly Pro
            20                  25                  30

<210> SEQ ID NO 31
<211> LENGTH: 30
<212> TYPE: PRT
<213> ORGANISM: artificial sequence
<220> FEATURE:
<223> OTHER INFORMATION: Ectropis obliqua picorna-like virus 2A1

<400> SEQUENCE: 31

Gly Gln Arg Thr Thr Glu Gln Ile Val Thr Ala Gln Gly Trp Ala Pro
1               5                   10                  15

Asp Leu Thr Gln Asp Gly Asp Val Glu Ser Asn Pro Gly Pro
            20                  25                  30

<210> SEQ ID NO 32
<211> LENGTH: 30
<212> TYPE: PRT
<213> ORGANISM: artificial sequence
<220> FEATURE:
<223> OTHER INFORMATION: Ectropis obliqua picorna-like virus 2A2

<400> SEQUENCE: 32

Thr Arg Gly Gly Leu Gln Arg Gln Asn Ile Ile Gly Gly Gln Arg
1               5                   10                  15

Asp Leu Thr Gln Asp Gly Asp Ile Glu Ser Asn Pro Gly Pro
            20                  25                  30

<210> SEQ ID NO 33
<211> LENGTH: 30
<212> TYPE: PRT
<213> ORGANISM: artificial sequence
<220> FEATURE:
<223> OTHER INFORMATION: Drosophila C virus 2A

<400> SEQUENCE: 33

Gln Gly Ile Gly Lys Lys Asn Pro Lys Gln Glu Ala Ala Arg Gln Met
1               5                   10                  15

Leu Leu Leu Leu Ser Gly Asp Val Glu Thr Asn Pro Gly Pro
            20                  25                  30

<210> SEQ ID NO 34
<211> LENGTH: 30
<212> TYPE: PRT
<213> ORGANISM: artificial sequence
<220> FEATURE:
<223> OTHER INFORMATION: acute bee paralysis virus 2A

<400> SEQUENCE: 34

Thr Gly Phe Leu Asn Lys Leu Tyr His Cys Gly Ser Trp Thr Asp Ile
1               5                   10                  15

Leu Leu Leu Leu Ser Gly Asp Val Glu Thr Asn Pro Gly Pro
            20                  25                  30
```

<210> SEQ ID NO 35
<211> LENGTH: 30
<212> TYPE: PRT
<213> ORGANISM: artificial sequence
<220> FEATURE:
<223> OTHER INFORMATION: Euprosterna elaeasa virus 2A

<400> SEQUENCE: 35

Arg Arg Leu Pro Glu Ser Ala Gln Leu Pro Gln Gly Ala Gly Arg Gly
1               5                   10                  15

Ser Leu Val Thr Cys Gly Asp Val Glu Glu Asn Pro Gly Pro
            20                  25                  30

<210> SEQ ID NO 36
<211> LENGTH: 30
<212> TYPE: PRT
<213> ORGANISM: artificial sequence
<220> FEATURE:
<223> OTHER INFORMATION: Providence virus 2A1

<400> SEQUENCE: 36

Leu Glu Met Lys Glu Ser Asn Ser Gly Tyr Val Val Gly Asp Arg Gly
1               5                   10                  15

Ser Leu Leu Thr Cys Gly Asp Val Glu Ser Asn Pro Gly Pro
            20                  25                  30

<210> SEQ ID NO 37
<211> LENGTH: 30
<212> TYPE: PRT
<213> ORGANISM: artificial sequence
<220> FEATURE:
<223> OTHER INFORMATION: Providence virus 2A3

<400> SEQUENCE: 37

Thr Leu Met Gly Asn Ile Met Thr Leu Ala Gly Ser Gly Gly Arg Gly
1               5                   10                  15

Ser Leu Leu Thr Ala Gly Asp Val Glu Lys Asn Pro Gly Pro
            20                  25                  30

<210> SEQ ID NO 38
<211> LENGTH: 30
<212> TYPE: PRT
<213> ORGANISM: artificial sequence
<220> FEATURE:
<223> OTHER INFORMATION: Bombyx mori cypovirus-1 2A

<400> SEQUENCE: 38

Arg Thr Ala Phe Asp Phe Gln Gln Asp Val Phe Arg Ser Asn Tyr Asp
1               5                   10                  15

Leu Leu Lys Leu Cys Gly Asp Ile Glu Ser Asn Pro Gly Pro
            20                  25                  30

<210> SEQ ID NO 39
<211> LENGTH: 30
<212> TYPE: PRT
<213> ORGANISM: artificial sequence
<220> FEATURE:
<223> OTHER INFORMATION: Operophtera brumata cypovirus-18 2A

<400> SEQUENCE: 39

Ile His Ala Asn Asp Tyr Gln Met Ala Val Phe Lys Ser Asn Tyr Asp
1               5                   10                  15

Leu Leu Lys Leu Cys Gly Asp Val Glu Ser Asn Pro Gly Pro
            20                  25                  30

<210> SEQ ID NO 40
<211> LENGTH: 30
<212> TYPE: PRT
<213> ORGANISM: artificial sequence
<220> FEATURE:
<223> OTHER INFORMATION: new adult diarrhea virus 2A

<400> SEQUENCE: 40

Phe Phe Asp Ser Val Trp Val Tyr His Leu Ala Asn Ser Ser Trp Val
1               5                   10                  15

Arg Asp Leu Thr Arg Glu Cys Ile Glu Ser Asn Pro Gly Pro
            20                  25                  30

<210> SEQ ID NO 41
<211> LENGTH: 8
<212> TYPE: PRT
<213> ORGANISM: artificial sequence
<220> FEATURE:
<223> OTHER INFORMATION: Consensus motif
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid

<400> SEQUENCE: 41

Asp Xaa Glu Xaa Asn Pro Gly Pro
1               5

<210> SEQ ID NO 42
<211> LENGTH: 280
<212> TYPE: DNA
<213> ORGANISM: artificial sequence
<220> FEATURE:
<223> OTHER INFORMATION: Rous sarcoma virus U3 (Cullen BR et al. (1985)
      Mol Cell Biol 5(3): 438-447)

<400> SEQUENCE: 42
agtcccctca ggatatagta gtttcgcttt tgcataggga gggggaaatg tagccttatg      60
caatactctt gtagtcttgc aacatgctta tgtaacgatg agttagcaac atgccttaca     120
aggagagaaa aagcaccgtg catgccgatt ggtggaagta aggtggtacg atcgtgcctt     180
attaggaagg caacagacgg gtctgacatg gattggacga accaccgaat tcgcattgca     240
gagagtattg tatttaagtg cctagctcga tacaataaac                           280

<210> SEQ ID NO 43
<211> LENGTH: 1503
<212> TYPE: DNA
<213> ORGANISM: artificial sequence
<220> FEATURE:
<223> OTHER INFORMATION: HIV-1 gag nucleotide sequence from plasmid
      psPAX2

<400> SEQUENCE: 43
atgggtgcga gagcgtcagt attaagcggg ggagaattag atcgatggga aaaaattcgg      60
ttaaggccag ggggaaagaa aaaatataaa ttaaaacata tagtatgggc aagcagggag     120
ctagaacgat tcgcagttaa tcctggcctg ttagaaacat cagaaggctg tagacaaata     180
ctgggacagc tacaaccatc ccttcagaca ggatcagaag aacttagatc attatataat     240
acagtagcaa ccctctattg tgtgcatcaa aggatagaga taaaagacac caaggaagct     300

```
ttagacaaga tagaggaaga gcaaaacaaa agtaagaaaa aagcacagca agcagcagct      360
gacacaggac acagcaatca ggtcagccaa aattacccta tagtgcagaa catccagggg      420
caaatggtac atcaggccat atcacctaga actttaaatg catgggtaaa agtagtagaa      480
gagaaggctt tcagcccaga agtgataccc atgttttcag cattatcaga aggagccacc      540
ccacaagatt taaacaccat gctaaacaca gtggggggac atcaagcagc catgcaaatg      600
ttaaaagaga ccatcaatga ggaagctgca gaatgggata gagtgcatcc agtgcatgca      660
gggcctattg caccaggcca gatgagagaa ccaaggggaa gtgacatagc aggaactact      720
agtacccttc aggaacaaat aggatggatg acacataatc cacctatccc agtaggagaa      780
atctataaaa gatggataat cctgggatta aataaaatag taagaatgta tagccctacc      840
agcattctgg acataagaca aggaccaaag gaacccttta gagactatgt agaccgattc      900
tataaaactc taagagccga gcaagcttca caagaggtaa aaaattggat gacagaaacc      960
ttgttggtcc aaaatgcgaa cccagattgt aagactattt taaaagcatt gggaccagga     1020
gcgacactag aagaaatgat gacagcatgt cagggagtgg ggggacccgg ccataaagca     1080
agagttttgg ctgaagcaat gagccaagta acaaatccag ctaccataat gatacagaaa     1140
ggcaatttta ggaaccaaag aaagactgtt aagtgtttca attgtggcaa agaagggcac     1200
atagccaaaa attgcagggc ccctaggaaa aagggctgtt ggaaatgtgg aaaggaagga     1260
caccaaatga aagattgtac tgagagacag gctaattttt tagggaagat ctggccttcc     1320
cacaagggaa ggccagggaa ttttcttcag agcagaccag agccaacagc cccaccagaa     1380
gagagcttca ggtttgggga agagacaaca actccctctc agaagcagga gccgatagac     1440
aaggaactgt atcctttagc ttccctcaga tcactctttg gcagcgaccc ctcgtcacaa     1500
taa                                                                   1503
```

<210> SEQ ID NO 44
<211> LENGTH: 500
<212> TYPE: PRT
<213> ORGANISM: artificial sequence
<220> FEATURE:
<223> OTHER INFORMATION: HIV-1 gag protein sequence from plasmid psPAX2

<400> SEQUENCE: 44

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140
```

Gln Ala Ile Ser Pro Arg Thr Leu Asn Ala Trp Val Lys Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Arg Gln Gly
                275                 280                 285

Pro Lys Glu Pro Phe Arg Asp Tyr Val Asp Arg Phe Tyr Lys Thr Leu
                290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
                340                 345                 350

Val Gly Gly Pro Gly His Lys Ala Arg Val Leu Ala Glu Ala Met Ser
                355                 360                 365

Gln Val Thr Asn Pro Ala Thr Ile Met Ile Gln Lys Gly Asn Phe Arg
370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser His Lys Gly Arg Pro Gly Asn Phe
                435                 440                 445

Leu Gln Ser Arg Pro Glu Pro Thr Ala Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500

<210> SEQ ID NO 45
<211> LENGTH: 1503
<212> TYPE: DNA
<213> ORGANISM: artificial sequence
<220> FEATURE:
<223> OTHER INFORMATION: HIV-1 gag nucleotide sequence from plasmid
      pNL4-3 (GenBank accession no. AF324493.2)

<400> SEQUENCE: 45

```
atgggtgcga gagcgtcggt attaagcggg ggagaattag ataaatggga aaaaattcgg      60
ttaaggccag ggggaaagaa acaatataaa ctaaaacata tagtatgggc aagcagggag     120
ctagaacgat tcgcagttaa tcctggcctt ttagagacat cagaaggctg tagacaaata     180
ctgggacagc tacaaccatc ccttcagaca ggatcagaag aacttagatc attatataat     240
acaatagcag tcctctattg tgtgcatcaa aggatagatg taaaagacac caaggaagcc     300
ttagataaga tagaggaaga gcaaaacaaa agtaagaaaa aggcacagca agcagcagct     360
gacacaggaa acaacagcca ggtcagccaa aattacccta tagtgcagaa cctccagggg     420
caaatggtac atcaggccat atcacctaga actttaaatg catgggtaaa agtagtagaa     480
gagaaggctt tcagcccaga agtaataccc atgttttcag cattatcaga aggagccacc     540
ccacaagatt taaataccat gctaaacaca gtggggggac atcaagcagc catgcaaatg     600
ttaaaagaga ccatcaatga ggaagctgca gaatgggata gattgcatcc agtgcatgca     660
gggcctattg caccaggcca gatgagagaa ccaaggggaa gtgacatagc aggaactact     720
agtacccttc aggaacaaat aggatggatg acacataatc cacctatccc agtaggagaa     780
atctataaaa gatggataat cctgggatta aataaaatag taagaatgta tagccctacc     840
agcattctgg acataagaca aggaccaaag gaacccttta gagactatgt agaccgattc     900
tataaaactc taagagccga gcaagcttca caagaggtaa aaaattggat gacagaaacc     960
ttgttggtcc aaaatgcgaa cccagattgt aagactattt taaaagcatt gggaccagga    1020
gcgacactag aagaaatgat gacagcatgt cagggagtgg ggggacccgg ccataaagca    1080
agagttttgg ctgaagcaat gagccaagta acaaatccag ctaccataat gatacagaaa    1140
ggcaatttta ggaaccaaag aaagactgtt aagtgtttca attgtggcaa agaagggcac    1200
atagccaaaa attgcagggc ccctaggaaa aagggctgtt ggaaatgtgg aaaggaagga    1260
caccaaatga aagattgtac tgagagacag gctaattttt tagggaagat ctggccttcc    1320
cacaagggaa ggccagggaa ttttcttcag agcagaccag agccaacagc cccaccagaa    1380
gagagcttca ggtttgggga agagacaaca actccctctc agaagcagga gccgatagac    1440
aaggaactgt atcctttagc ttccctcaga tcactctttg gcagcgaccc ctcgtcacaa    1500
taa                                                                 1503
```

<210> SEQ ID NO 46
<211> LENGTH: 500
<212> TYPE: PRT
<213> ORGANISM: artificial sequence
<220> FEATURE:
<223> OTHER INFORMATION: HIV-1 gag protein sequence from plasmid pNL4-3
      (GenBank accession no. AAK08483.1)

<400> SEQUENCE: 46

```
Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Gln Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80
```

```
Thr Ile Ala Val Leu Tyr Cys Val His Gln Arg Ile Asp Val Lys Asp
                    85                  90                  95

Thr Lys Glu Ala Leu Asp Lys Ile Glu Glu Gln Asn Lys Ser Lys
            100                 105                 110

Lys Lys Ala Gln Gln Ala Ala Asp Thr Gly Asn Asn Ser Gln Val
        115                 120                 125

Ser Gln Asn Tyr Pro Ile Val Gln Asn Leu Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495
```

Pro Ser Ser Gln
        500

<210> SEQ ID NO 47
<211> LENGTH: 3012
<212> TYPE: DNA
<213> ORGANISM: artificial sequence
<220> FEATURE:
<223> OTHER INFORMATION: HIV-1 pol nucleotide sequence from plasmid
      psPAX2

<400> SEQUENCE: 47

| | | | | |
|---|---|---|---|---|
| tttttagg | aagatctggc | cttcccacaa | gggaaggcca | gggaattttc | ttcagagcag | 60 |
| accagagcca | acagccccac | cagaagagag | cttcaggttt | ggggaagaga | caacaactcc | 120 |
| ctctcagaag | caggagccga | tagacaagga | actgtatcct | ttagcttccc | tcagatcact | 180 |
| ctttggcagc | gacccctcgt | cacaataaag | ataggggggc | aattaaagga | agctctatta | 240 |
| gatacaggag | cagatgatac | agtattagaa | gaaatgaatt | tgccaggaag | atggaaacca | 300 |
| aaaatgatag | ggggaattgg | aggttttatc | aaagtaagac | agtatgatca | gatactcata | 360 |
| gaaatctgcg | gacataaagc | tataggtaca | gtattagtag | gacctacacc | tgtcaacata | 420 |
| attggaagaa | atctgttgac | tcagattggc | tgcactttaa | attttcccat | tagtcctatt | 480 |
| gagactgtac | cagtaaaatt | aaagccagga | atggatggcc | caaaagttaa | acaatggcca | 540 |
| ttgacagaag | aaaaaataaa | agcattagta | gaaatttgta | cagaaatgga | aaaggaagga | 600 |
| aaaatttcaa | aaattgggcc | tgaaaatcca | tacaatactc | cagtatttgc | cataaagaaa | 660 |
| aaagacagta | ctaaatggag | aaaattagta | gatttcagag | aacttaataa | gagaactcaa | 720 |
| gatttctggg | aagttcaatt | aggaatacca | catcctgcag | ggttaaaaca | gaaaaaatca | 780 |
| gtaacagtac | tggatgtggg | cgatgcatat | ttttcagttc | ccttagataa | agacttcagg | 840 |
| aagtatactg | catttaccat | acctagtata | aacaatgaga | caccagggat | tagatatcag | 900 |
| tacaatgtgc | ttccacaggg | atggaaagga | tcaccagcaa | tattccagtg | tagcatgaca | 960 |
| aaaatcttag | agccttttag | aaaacaaaat | ccagacatag | tcatctatca | atacatggat | 1020 |
| gatttgtatg | taggatctga | cttagaaata | gggcagcata | gaacaaaaat | agaggaactg | 1080 |
| agacaacatc | tgttgaggtg | gggatttacc | acaccagaca | aaaaacatca | gaaagaacct | 1140 |
| ccattccttt | ggatgggtta | tgaactccat | cctgataaat | ggacagtaca | gcctatagtg | 1200 |
| ctgccagaaa | aggacagctg | gactgtcaat | gacatacaga | agttagtggg | aaaattgaat | 1260 |
| tgggcaagtc | agatttatgc | agggattaaa | gtaaggcaat | tatgtaaact | tcttagggga | 1320 |
| accaaagcac | taacagaagt | agtaccacta | acagaagaag | cagagctaga | actggcagaa | 1380 |
| aacagggaga | ttctaaaaga | accggtacat | ggagtgtatt | atgacccatc | aaaagactta | 1440 |
| atagcagaaa | tacagaagca | ggggcaaggc | caatggacat | atcaaattta | tcaagagcca | 1500 |
| tttaaaaatc | tgaaaacagg | aaagtatgca | agaatgaagg | gtgcccacac | taatgatgtg | 1560 |
| aaacaattaa | cagaggcagt | gcaaaaaata | gccacagaaa | gcatagtaat | atggggaaag | 1620 |
| actcctaaat | ttaaattacc | catacaaaag | gaaacatggg | aagcatggtg | gacagagtat | 1680 |
| tggcaagcca | cctggattcc | tgagtgggag | tttgtcaata | cccctccctt | agtgaagtta | 1740 |
| tggtaccagt | tagagaaaga | acccataata | ggagcagaaa | ctttctatgt | agatggggca | 1800 |
| gccaataggg | aaactaaatt | aggaaaagca | ggatatgtaa | ctgacagagg | aagacaaaaa | 1860 |
| gttgtccccc | taacggacac | aacaaatcag | aagactgagt | tacaagcaat | tcatctagct | 1920 |
| ttgcaggatt | cgggattaga | agtaaacata | gtgacagact | cacaatatgc | attgggaatc | 1980 |

-continued

```
attcaagcac aaccagataa gagtgaatca gagttagtca gtcaaataat agagcagtta    2040
ataaaaaagg aaaaagtcta cctggcatgg gtaccagcac acaaaggaat tggaggaaat    2100
gaacaagtag ataaattggt cagtgctgga atcaggaaag tactatttt agatggaata    2160 gataaggccc aagaagaaca tgagaaatat cacagtaatt ggagagcaat ggctagtgat    2220
tttaacctac cacctgtagt agcaaaagaa atagtagcca gctgtgataa atgtcagcta    2280
aaaggggaag ccatgcatgg acaagtagac tgtagcccag gaatatggca gctagattgt    2340
acacatttag aaggaaaagt tatcttggta gcagttcatg tagccagtgg atatatagaa    2400
gcagaagtaa ttccagcaga cagggcaa gaaacagcat acttcctctt aaaattagca    2460
ggaagatggc cagtaaaaac agtacataca gacaatggca gcaatttcac cagtactaca    2520
gttaaggccg cctgttggtg ggcggggatc aagcaggaat ttggcattcc ctacaatccc    2580
caaagtcaag gagtaataga atctatgaat aaagaattaa agaaaattat aggacaggta    2640
agagatcagg ctgaacatct taagacagca gtacaaatgg cagtattcat ccacaatttt    2700
aaaagaaaag ggggggattgg ggggtacagt gcaggggaaa gaatagtaga cataatagca    2760
acagacatac aaactaaaga attacaaaaa caaattacaa aaattcaaaa ttttcgggtt    2820
tattacaggg acagcagaga tccagtttgg aaaggaccag caaagctcct ctggaaaggt    2880
gaaggggcag tagtaataca agataatagt gacataaaag tagtgccaag aagaaaagca    2940
aagatcatca gggattatgg aaaacagatg gcaggtgatg attgtgtggc aagtagacag    3000
gatgaggatt aa                                                       3012
```

<210> SEQ ID NO 48
<211> LENGTH: 1003
<212> TYPE: PRT
<213> ORGANISM: artificial sequence
<220> FEATURE:
<223> OTHER INFORMATION: HIV-1 pol protein sequence from psPAX2

<400> SEQUENCE: 48

```
Phe Phe Arg Glu Asp Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
                20                  25                  30

Val Trp Gly Arg Asp Asn Asn Ser Leu Ser Glu Ala Gly Ala Asp Arg
            35                  40                  45

Gln Gly Thr Val Ser Phe Ser Phe Pro Gln Ile Thr Leu Trp Gln Arg
        50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
                100                 105                 110

Arg Gln Tyr Asp Gln Ile Leu Ile Glu Ile Cys Gly His Lys Ala Ile
            115                 120                 125

Gly Thr Val Leu Val Gly Pro Thr Pro Val Asn Ile Ile Gly Arg Asn
        130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175
```

```
Lys Gln Trp Pro Leu Thr Glu Glu Lys Ile Lys Ala Leu Val Glu Ile
                180                 185                 190

Cys Thr Glu Met Glu Lys Glu Gly Lys Ile Ser Lys Ile Gly Pro Glu
            195                 200                 205

Asn Pro Tyr Asn Thr Pro Val Phe Ala Ile Lys Lys Lys Asp Ser Thr
210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Gln Lys Lys Ser Val Thr Val Leu Asp Val Gly Asp Ala Tyr Phe Ser
            260                 265                 270

Val Pro Leu Asp Lys Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
290                 295                 300

Pro Gln Gly Trp Lys Gly Ser Pro Ala Ile Phe Gln Cys Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Phe Thr Thr Pro Asp Lys Lys His Gln Lys Glu Pro Pro Phe Leu Trp
370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Ala Gly Ile Lys Val Arg
            420                 425                 430

Gln Leu Cys Lys Leu Leu Arg Gly Thr Lys Ala Leu Thr Glu Val Val
        435                 440                 445

Pro Leu Thr Glu Glu Ala Glu Leu Glu Leu Ala Glu Asn Arg Glu Ile
450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Lys Asn Leu Lys Thr Gly Lys Tyr Ala Arg Met
            500                 505                 510

Lys Gly Ala His Thr Asn Asp Val Lys Gln Leu Thr Glu Ala Val Gln
        515                 520                 525

Lys Ile Ala Thr Glu Ser Ile Val Ile Trp Gly Lys Thr Pro Lys Phe
530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Ile Gly Ala
            580                 585                 590
```

```
Glu Thr Phe Tyr Val Asp Gly Ala Ala Asn Arg Glu Thr Lys Leu Gly
        595                 600                 605

Lys Ala Gly Tyr Val Thr Asp Arg Gly Arg Gln Lys Val Val Pro Leu
610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
                660                 665                 670

Val Ser Gln Ile Ile Glu Gln Leu Ile Lys Lys Glu Lys Val Tyr Leu
                675                 680                 685

Ala Trp Val Pro Ala His Lys Gly Ile Gly Gly Asn Glu Gln Val Asp
        690                 695                 700

Lys Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Asp Phe Asn Leu Pro Pro Val Val Ala Lys Glu Ile Val
        740                 745                 750

Ala Ser Cys Asp Lys Cys Gln Leu Lys Gly Glu Ala Met His Gly Gln
        755                 760                 765

Val Asp Cys Ser Pro Gly Ile Trp Gln Leu Asp Cys Thr His Leu Glu
        770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Val His Thr Asp Asn
                820                 825                 830

Gly Ser Asn Phe Thr Ser Thr Thr Val Lys Ala Ala Cys Trp Trp Ala
        835                 840                 845

Gly Ile Lys Gln Glu Phe Gly Ile Pro Tyr Asn Pro Gln Ser Gln Gly
850                 855                 860

Val Ile Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
                900                 905                 910

Glu Arg Ile Val Asp Ile Ile Ala Thr Asp Ile Gln Thr Lys Glu Leu
                915                 920                 925

Gln Lys Gln Ile Thr Lys Ile Gln Asn Phe Arg Val Tyr Tyr Arg Asp
        930                 935                 940

Ser Arg Asp Pro Val Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
                980                 985                 990

Asp Asp Cys Val Ala Ser Arg Gln  Asp Glu Asp
        995                 1000
```

<210> SEQ ID NO 49
<211> LENGTH: 3012
<212> TYPE: DNA
<213> ORGANISM: artificial sequence
<220> FEATURE:
<223> OTHER INFORMATION: HIV-1 pol nucleotide sequence from plasmid
      pNL4-3 (GenBank accession no. AF324493.2)

<400> SEQUENCE: 49

| | | | | | |
|---|---|---|---|---|---|
| tttttagggg | aagatctggc | cttcccacaa | gggaaggcca | gggaattttc | ttcagagcag | 60 |
| accagagcca | acagccccac | cagaagagag | cttcaggttt | ggggaagaga | caacaactcc | 120 |
| ctctcagaag | caggagccga | tagacaagga | actgtatcct | ttagcttccc | tcagatcact | 180 |
| ctttggcagc | gacccctcgt | cacaataaag | ataggggggc | aattaaagga | agctctatta | 240 |
| gatacaggag | cagatgatac | agtattagaa | gaaatgaatt | tgccaggaag | atggaaacca | 300 |
| aaaatgatag | ggggaattgg | aggttttatc | aaagtaagac | agtatgatca | gatactcata | 360 |
| gaaatctgcg | gacataaagc | tataggtaca | gtattagtag | gacctacacc | tgtcaacata | 420 |
| attggaagaa | atctgttgac | tcagattggc | tgcactttaa | attttcccat | tagtcctatt | 480 |
| gagactgtac | cagtaaaatt | aaagccagga | atggatggcc | caaaagttaa | acaatggcca | 540 |
| ttgacagaag | aaaaaataaa | agcattagta | gaaatttgta | cagaaatgga | aaaggaagga | 600 |
| aaaatttcaa | aaattgggcc | tgaaaatcca | tacaatactc | cagtatttgc | cataaagaaa | 660 |
| aaagacagta | ctaaatggag | aaaattagta | gatttcagag | aacttaataa | gagaactcaa | 720 |
| gatttctggg | aagttcaatt | aggaatacca | catcctgcag | ggttaaaaca | gaaaaaatca | 780 |
| gtaacagtac | tggatgtggg | cgatgcatat | ttttcagttc | ccttagataa | agacttcagg | 840 |
| aagtatactg | catttaccat | acctagtata | aacaatgaga | caccagggat | tagatatcag | 900 |
| tacaatgtgc | ttccacaggg | atggaaagga | tcaccagcaa | tattccagtg | tagcatgaca | 960 |
| aaaatcttag | agccttttag | aaaacaaaat | ccagacatag | tcatctatca | atacatggat | 1020 |
| gatttgtatg | taggatctga | cttagaaata | gggcagcata | gaacaaaaat | agaggaactg | 1080 |
| agacaacatc | tgttgaggtg | gggatttacc | acaccagaca | aaaacatca | gaaagaacct | 1140 |
| ccattccttt | ggatgggtta | tgaactccat | cctgataaat | ggacagtaca | gcctatagtg | 1200 |
| ctgccagaaa | aggacagctg | gactgtcaat | gacatacaga | aattagtggg | aaaattgaat | 1260 |
| tgggcaagtc | agatttatgc | agggattaaa | gtaaggcaat | tatgtaaact | tcttagggga | 1320 |
| accaaagcac | taacagaagt | agtaccacta | acagaagaag | cagagctaga | actggcagaa | 1380 |
| aacagggaga | ttctaaaaga | accggtacat | ggagtgtatt | atgacccatc | aaaagactta | 1440 |
| atagcagaaa | tacagaagca | ggggcaaggc | caatggacat | atcaaattta | tcaagagcca | 1500 |
| tttaaaaatc | tgaaaacagg | aaagtatgca | agaatgaagg | gtgcccacac | taatgatgtg | 1560 |
| aaacaattaa | cagaggcagt | acaaaaaata | gccacagaaa | gcatagtaat | atggggaaag | 1620 |
| actcctaaat | ttaaattacc | catacaaaag | gaaacatggg | aagcatggtg | gacagagtat | 1680 |
| tggcaagcca | cctggattcc | tgagtgggag | tttgtcaata | cccctccctt | agtgaagtta | 1740 |
| tggtaccagt | tagagaaaga | acccataata | ggagcagaaa | cttctatgt | agatgggca | 1800 |
| gccaataggg | aaactaaatt | aggaaaagca | ggatatgtaa | ctgacagagg | aagacaaaaa | 1860 |
| gttgtccccc | taacggacac | aacaaatcag | aagactgagt | tacaagcaat | tcatctagct | 1920 |
| ttgcaggatt | cgggattaga | agtaaacata | gtgacagact | cacaatatgc | attgggaatc | 1980 |
| attcaagcac | aaccagataa | gagtgaatca | gagttagtca | gtcaaataat | agagcagtta | 2040 |
| ataaaaaagg | aaaaagtcta | cctggcatgg | gtaccagcac | acaaaggaat | tggaggaaat | 2100 |

-continued

```
gaacaagtag ataaattggt cagtgctgga atcaggaaag tactattttt agatggaata    2160
gataaggccc aagaagaaca tgagaaatat cacagtaatt ggagagcaat ggctagtgat    2220
tttaacctac cacctgtagt agcaaaagaa atagtagcca gctgtgataa atgtcagcta    2280
aaaggggaag ccatgcatgg acaagtagac tgtagcccag gaatatggca gctagattgt    2340
acacatttag aaggaaaagt tatcttggta gcagttcatg tagccagtgg atatatagaa    2400
gcagaagtaa ttccagcaga cagggcaa gaaacagcat acttcctctt aaaattagca    2460
ggaagatggc cagtaaaaac agtacataca gacaatggca gcaatttcac cagtactaca    2520
gttaaggccg cctgttggtg ggcggggatc aagcaggaat ttggcattcc ctacaatccc    2580
caaagtcaag gagtaataga atctatgaat aaagaattaa agaaaattat aggacaggta    2640
agagatcagg ctgaacatct taagacagca gtacaaatgg cagtattcat ccacaatttt    2700
aaaagaaaag ggggattggg gggtacagt gcaggggaaa gaatagtaga cataatagca    2760
acagacatac aaactaaaga attacaaaaa caaattacaa aaattcaaaa ttttcgggtt    2820
tattacaggg acagcagaga tccagtttgg aaaggaccag caaagctcct ctggaaaggt    2880
gaaggggcag tagtaataca agataatagt gacataaaag tagtgccaag aagaaaagca    2940
aagatcatca gggattatgg aaaacagatg gcaggtgatg attgtgtggc aagtagacag    3000
gatgaggatt aa    3012
```

<210> SEQ ID NO 50
<211> LENGTH: 1003
<212> TYPE: PRT
<213> ORGANISM: artificial sequence
<220> FEATURE:
<223> OTHER INFORMATION: HIV-1 pol protein sequence from plasmid pNL4-3
      (GenBank accession no. AAK08484.2)

<400> SEQUENCE: 50

```
Phe Phe Arg Glu Asp Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190
```

```
Cys Thr Glu Met Glu Lys Glu Gly Lys Ile Ser Lys Ile Gly Pro Glu
            195                 200                 205

Asn Pro Tyr Asn Thr Pro Val Phe Ala Ile Lys Lys Lys Asp Ser Thr
210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
            245                 250                 255

Gln Lys Lys Ser Val Thr Val Leu Asp Val Gly Asp Ala Tyr Phe Ser
            260                 265                 270

Val Pro Leu Asp Lys Asp Phe Arg Lys Tyr Thr Ala Phe Thr Ile Pro
            275                 280                 285

Ser Ile Asn Asn Glu Thr Pro Gly Ile Arg Tyr Gln Tyr Asn Val Leu
            290                 295                 300

Pro Gln Gly Trp Lys Gly Ser Pro Ala Ile Phe Gln Cys Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
            355                 360                 365

Phe Thr Thr Pro Asp Lys Lys His Gln Lys Glu Pro Pro Phe Leu Trp
            370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Ala Gly Ile Lys Val Arg
            420                 425                 430

Gln Leu Cys Lys Leu Leu Arg Gly Thr Lys Ala Leu Thr Glu Val Val
            435                 440                 445

Pro Leu Thr Glu Glu Ala Glu Leu Glu Leu Ala Glu Asn Arg Glu Ile
            450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Lys Asn Leu Lys Thr Gly Lys Tyr Ala Arg Met
            500                 505                 510

Lys Gly Ala His Thr Asn Asp Val Lys Gln Leu Thr Glu Ala Val Gln
            515                 520                 525

Lys Ile Ala Thr Glu Ser Ile Val Ile Trp Gly Lys Thr Pro Lys Phe
530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Ile Gly Ala
            580                 585                 590

Glu Thr Phe Tyr Val Asp Gly Ala Ala Asn Arg Glu Thr Lys Leu Gly
            595                 600                 605
```

```
Lys Ala Gly Tyr Val Thr Asp Arg Gly Arg Gln Lys Val Val Pro Leu
    610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
    690                 695                 700

Lys Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Asp Phe Asn Leu Pro Pro Val Val Ala Lys Glu Ile Val
            740                 745                 750

Ala Ser Cys Asp Lys Cys Gln Leu Lys Gly Glu Ala Met His Gly Gln
        755                 760                 765

Val Asp Cys Ser Pro Gly Ile Trp Gln Leu Asp Cys Thr His Leu Glu
    770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Val His Thr Asp Asn
            820                 825                 830

Gly Ser Asn Phe Thr Ser Thr Thr Val Lys Ala Ala Cys Trp Trp Ala
        835                 840                 845

Gly Ile Lys Gln Glu Phe Gly Ile Pro Tyr Asn Pro Gln Ser Gln Gly
    850                 855                 860

Val Ile Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
        915                 920                 925

Gln Lys Gln Ile Thr Lys Ile Gln Asn Phe Arg Val Tyr Tyr Arg Asp
    930                 935                 940

Ser Arg Asp Pro Val Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln  Asp Glu Asp
            995                 1000

<210> SEQ ID NO 51
<211> LENGTH: 261
<212> TYPE: DNA
```

<213> ORGANISM: artificial sequence
<220> FEATURE:
<223> OTHER INFORMATION: HIV-1 Tat coding sequence from plasmid pNL4-3
      (GenBank accession no. AF324493.2)

<400> SEQUENCE: 51

```
atggagccag tagatcctag actagagccc tggaagcatc caggaagtca gcctaaaact      60
gcttgtacca attgctattg taaaaagtgt tgctttcatt gccaagtttg tttcatgaca     120
aaagccttag gcatctccta tggcaggaag aagcggagac agcgacgaag agctcatcag     180
aacagtcaga ctcatcaagc ttctctatca agcaaccca cctcccaatc ccgagggac      240 ccgacaggcc cgaaggaata g                                                261
```

<210> SEQ ID NO 52
<211> LENGTH: 86
<212> TYPE: PRT
<213> ORGANISM: artificial sequence
<220> FEATURE:
<223> OTHER INFORMATION: HIV-1 Tat protein sequence from plasmid pNL4-3
      (GenBank accession no. AAK08486.1)

<400> SEQUENCE: 52

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Met Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Ser Arg Gly Asp
65                  70                  75                  80

Pro Thr Gly Pro Lys Glu
                85
```

<210> SEQ ID NO 53
<211> LENGTH: 351
<212> TYPE: DNA
<213> ORGANISM: artificial sequence
<220> FEATURE:
<223> OTHER INFORMATION: HIV-1 Rev coding sequence from plasmid pNL4-3
      (GenBank accession no. AF324493.2)

<400> SEQUENCE: 53

```
atggcaggaa gaagcggaga cagcgacgaa gagctcatca gaacagtcag actcatcaag      60
cttctctatc aaagcaaccc acctcccaat cccgagggga cccgacaggc ccgaaggaat     120
agaagaagaa ggtggagaga gagacagaga cagatccatt cgattagtga acggatcctt     180
agcacttatc tgggacgatc tgcggagcct gtgcctcttc agctaccacc gcttgagaga     240
cttactcttg attgtaacga ggattgtgga acttctggga cgcaggggt gggaagccct     300 caaatattgg tggaatctcc tacagtattg gagtcaggaa ctaaagaata g              351
```

<210> SEQ ID NO 54
<211> LENGTH: 116
<212> TYPE: PRT
<213> ORGANISM: artificial sequence
<220> FEATURE:
<223> OTHER INFORMATION: HIV-1 Rev protein sequence from plasmid pNL4-3
      (GenBank accession no. AAK08487.1)

<400> SEQUENCE: 54

```
Met Ala Gly Arg Ser Gly Asp Ser Asp Glu Glu Leu Ile Arg Thr Val
1               5                   10                  15

Arg Leu Ile Lys Leu Leu Tyr Gln Ser Asn Pro Pro Asn Pro Glu
                20                  25              30

Gly Thr Arg Gln Ala Arg Arg Asn Arg Arg Arg Trp Arg Glu Arg
            35                  40              45

Gln Arg Gln Ile His Ser Ile Ser Glu Arg Ile Leu Ser Thr Tyr Leu
    50              55                  60

Gly Arg Ser Ala Glu Pro Val Pro Leu Gln Leu Pro Pro Leu Glu Arg
65              70                  75              80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Val Leu Glu Ser
                100             105                 110

Gly Thr Lys Glu
        115

<210> SEQ ID NO 55

<400> SEQUENCE: 55

000

<210> SEQ ID NO 56

<400> SEQUENCE: 56

000

<210> SEQ ID NO 57
<211> LENGTH: 46
<212> TYPE: DNA
<213> ORGANISM: Artificial Sequence
<220> FEATURE:
<223> OTHER INFORMATION: primer 5'-BsmBI-Aichi68-NP for amplification

<400> SEQUENCE: 57
catgatcgtc tcagggagca aaagcagggt agataatcac tcacag                46

<210> SEQ ID NO 58
<211> LENGTH: 43
<212> TYPE: DNA
<213> ORGANISM: Artificial Sequence
<220> FEATURE:
<223> OTHER INFORMATION: primer 3'-BsmBI-Aichi68-NP for amplification

<400> SEQUENCE: 58
catgatcgtc tcgtattagt agaaacaagg gtatttttct tta                   43
```